United States Patent [19]

Chaco et al.

[11] Patent Number: 5,822,544
[45] Date of Patent: Oct. 13, 1998

[54] PATIENT CARE AND COMMUNICATION SYSTEM

[75] Inventors: John Chaco, Seymour; Israel Hersh, Fairfield; Dmitry Orlovsky, Danbury; Joe Vincens, Prospect, all of Conn.

[73] Assignee: Executone Information Systems, Inc., Milford, Conn.

[21] Appl. No.: 426,490

[22] Filed: Apr. 20, 1995

Related U.S. Application Data

[63] Continuation of Ser. No. 33,287, Mar. 16, 1993, abandoned, which is a continuation-in-part of Ser. No. 924,101, Aug. 3, 1992, Pat. No. 5,465,082, which is a continuation-in-part of Ser. No. 559,196, Jul. 27, 1990, Pat. No. 5,291,399.

[51] Int. Cl.$^6$ ...................................................... G08B 5/22
[52] U.S. Cl. ................ 395/202; 340/825.36; 340/825.49
[58] Field of Search ..................................... 235/375, 377, 235/378, 382, 385; 340/525, 568, 573, 825.06, 825.07, 825.08, 825.36, 825.44, 825.45, 825.49; 364/401 M, 403; 370/85.4, 94.1, 94.2, 60, 85.7, 85.9, 85.14, 85.15, 96

[56] References Cited

U.S. PATENT DOCUMENTS

| | | |
|---|---|---|
| 3,439,320 | 4/1969 | Ward . |
| 3,478,344 | 11/1969 | Schwetzgebel et al. . |
| 3,604,900 | 9/1971 | Kalt . |
| 3,617,637 | 11/1971 | Gorman, II ................................ 348/16 |
| 3,665,461 | 5/1972 | Gnägi et al. ............................. 340/509 |
| 3,678,491 | 7/1972 | Day ......................................... 340/654 |
| 3,696,384 | 10/1972 | Lester . |
| 3,714,573 | 1/1973 | Gressman . |

(List continued on next page.)

FOREIGN PATENT DOCUMENTS

| | | |
|---|---|---|
| 0505627 | 9/1992 | European Pat. Off. . |
| 0505627A2 | 9/1992 | European Pat. Off. . |
| 2190525 | 11/1987 | United Kingdom . |
| 2193359 | 2/1988 | United Kingdom . |
| 2230365 | 10/1990 | United Kingdom . |
| 9105311 | 4/1991 | WIPO . |
| WO9105311 | 4/1991 | WIPO . |

OTHER PUBLICATIONS

*Microsoft Press Computer Dictionary, 2nd edition:* copyright 1994; p. 160.

Franchi et al, Multimedia Perspectives for Next Generation PAC Systems, Session 2B: Pictural Archival and Communications Systems, pp. 156, 157, 159, 161, 163, 165, 167 and 169, 1992.

Matsunobu & Wong, "Kapiolani Women's and Children's Medical Center," *Computers in Health Care,* Jun. 1986, pp. 20–26.

Ooi, Lim & Lau, "Low Cost RF Identification and Locating System," *IEEE Transactions on Consumer Electronics,* vol. 35, No. 4, Nov. 1989, pp. 831–839.

(List continued on next page.)

*Primary Examiner*—Gail O. Hayes
*Assistant Examiner*—Stephen R. Tkacs
*Attorney, Agent, or Firm*—Dilworth & Barrese

[57] ABSTRACT

A patient care and communication system which utilizes a central processing system and a plurality of remote stations electrically connected to the central processing system to facilitate audio, visual and data communications. The central processing system facilitates the audio, visual and data communications between the plurality of remote stations, and includes a system for determining which of the plurality of remote stations are transmitting the audio, visual and data communications and which of the plurality of remote stations are to receive the audio, visual and data communications. The central processing system also includes a system which establishes a communication link between the transmitting stations and the receiving stations. The remote stations include a processing system which also facilitates the audio, visual and data communications and a display for displaying the visual communications.

8 Claims, 48 Drawing Sheets

U.S. PATENT DOCUMENTS

| | | |
|---|---|---|
| 3,739,329 | 6/1973 | Lester . |
| 3,767,859 | 10/1973 | Doering et al. .......................... 379/106 |
| 3,816,662 | 6/1974 | Shaver et al. .............................. 348/16 |
| 3,872,440 | 3/1975 | Benz et al. .............................. 455/33.1 |
| 3,925,762 | 12/1975 | Heitlinger et al. .................. 340/870.09 |
| 3,946,159 | 3/1976 | Fay ............................................. 348/8 |
| 3,971,916 | 7/1976 | Moreno . |
| 4,001,550 | 1/1977 | Schatz . |
| 4,023,013 | 5/1977 | Khker . |
| 4,052,567 | 10/1977 | MacKay . |
| 4,126,768 | 11/1978 | Grenzow . |
| 4,153,898 | 5/1979 | Larime ................................. 340/397.1 |
| 4,216,462 | 8/1980 | McGrath et al. .................. 364/413.03 |
| 4,225,953 | 9/1980 | Simon et al. . |
| 4,237,344 | 12/1980 | Moore ...................................... 379/38 |
| 4,275,385 | 6/1981 | White ................................ 340/825.49 |
| 4,491,947 | 1/1985 | Frank ..................................... 370/94.2 |
| 4,532,419 | 7/1985 | Takeda . |
| 4,536,646 | 8/1985 | Adams et al. ........................... 235/377 |
| 4,553,267 | 11/1985 | Crimmins . |
| 4,648,123 | 3/1987 | Schrock .............................. 455/67.11 |
| 4,649,385 | 3/1987 | Aires et al. . |
| 4,650,981 | 3/1987 | Foletta . |
| 4,672,182 | 6/1987 | Hirokawa . |
| 4,677,657 | 6/1987 | Nagata et al. . |
| 4,680,785 | 7/1987 | Akiyama et al. ......................... 379/57 |
| 4,680,790 | 7/1987 | Packard et al. . |
| 4,692,604 | 9/1987 | Billings . |
| 4,725,694 | 2/1988 | Auer et al. . |
| 4,748,668 | 5/1988 | Shamir et al. . |
| 4,757,553 | 7/1988 | Crimmins . |
| 4,780,601 | 10/1988 | Vermesse . |
| 4,795,890 | 1/1989 | Goldman . |
| 4,795,897 | 1/1989 | Chalendard . |
| 4,798,322 | 1/1989 | Berstein et al. . |
| 4,810,864 | 3/1989 | Takahaski . |
| 4,813,879 | 3/1989 | Thenaisie et al. . |
| 4,825,052 | 4/1989 | Chemin et al. . |
| 4,835,372 | 5/1989 | Gombrich et al. ...................... 235/375 |
| 4,841,133 | 6/1989 | Gercekci et al. . |
| 4,849,615 | 7/1989 | Mollet . |
| 4,853,692 | 8/1989 | Wolk et al. . |
| 4,864,110 | 9/1989 | Guillou . |
| 4,864,115 | 9/1989 | Imran et al. . |
| 4,874,935 | 10/1989 | Younger . |
| 4,882,473 | 11/1989 | Bergeron et al. . |
| 4,893,001 | 1/1990 | Ohkubo et al. . |
| 4,893,330 | 1/1990 | Franco . |
| 4,899,334 | 2/1990 | Shimizu ................................... 370/60 |
| 4,899,373 | 2/1990 | Lee et al. . |
| 4,905,231 | 2/1990 | Leung et al. ........................... 370/94.1 |
| 4,906,853 | 3/1990 | Linwood et al. . |
| 4,916,441 | 4/1990 | Gombrich .............................. 345/169 |
| 4,940,963 | 7/1990 | Gutman et al. ......................... 340/313 |
| 4,955,000 | 9/1990 | Nastrom . |
| 4,955,019 | 9/1990 | Mizuhara et al. ..................... 370/85.7 |
| 4,967,195 | 10/1990 | Shipley .............................. 340/825.52 |
| 4,977,619 | 12/1990 | Crimmins . |
| 4,984,994 | 1/1991 | Yamamoto . |
| 5,017,794 | 5/1991 | Linwood et al. . |
| 5,027,314 | 6/1991 | Linwood et al. . |
| 5,038,800 | 8/1991 | Oba ......................................... 128/696 |
| 5,077,666 | 12/1991 | Brimm et al. ..................... 364/413.02 |
| 5,119,104 | 6/1992 | Heller . |
| 5,121,234 | 6/1992 | Ozeki et al. .............................. 359/50 |
| 5,127,003 | 6/1992 | Doll, Jr. et al. ..................... 370/110.1 |
| 5,130,793 | 7/1992 | Bordry et al. .............................. 348/6 |
| 5,157,737 | 10/1992 | Sklarew . |
| 5,164,985 | 11/1992 | Nysen et al. . |
| 5,173,883 | 12/1992 | Lie et al. . |
| 5,231,273 | 7/1993 | Cayuell et al. . |
| 5,237,609 | 8/1993 | Kmura . |
| 5,291,399 | 3/1994 | Chaco ............................... 364/413.02 |

OTHER PUBLICATIONS

Davies & Wakerly, "Synchronization and Matching in Redundant Systems" *IEEE Transactions on Computers*, vol. C–27, No. 6, Jun. 1978, pp. 531–539.

Infra–Com®.

R.C. Livermore, "Health Service Applications in England and Wales," *International Conference and Workshop on Smart card Applications and Technologies*, 1988, p. 5–eoa.

Brown, Valbona & Kitasanono, "A New Patient Record System Using the Laser–Card" *Optical Information Systems*, vol. 8, No. 4, Jul.–Aug., 1988, pp. 156–161.

D. Artusi, "The Technology of Smart Cards and Their Applications," *Electro/86 and Mini/Micro Northeast Conference*, 1986, pp. 1–8.

Futura & Futura II, Specifications Notice.

M. Siedband, "Data card system for filmless radiography", *Medical Imaging*, vol. 727, part 2, pp. 831–833, 1987.

R.G. Stevens, "Experiments with Computer Card Medication Records in Britain", *International Conference and Workshop on Smard card Applications and Technologies*, p. 12–eoa; 1988.

G.B. Latamore, "Smart Cards Get Smarter," *High Technology Business*, pp. 35–37, Sep. 1987.

B. Millar, "A credit card away from better healthcare," *The Health Service Journal*, vol. 99, No. 5141, Mar. 9, 1989, p. 289.

G. Moore, "The hospital connection" *Computer Systems Europe*, pp. 73–76, May 1989.

T. Kuroiwa, The application of the I.C. card in the area of medical health, *Proceeding the Ninth Annual Conference of the IEEE Engineering in Medicine and Biology Society*, vol. 4, pp. 2124–2125, 1987.

M. Oikawa, "Marketing activities in Finland," vol. 1, No. 2, pp. 102–103, 1989.

M.U. Shaffer, J.C. Rios, "Semi–automated heart station," *Proceeding of the 26th Annual Conference on Engineering in Medicine and Biology*, p. 40, 1973.

J. Green, "Niche market growth for cards," *Communications International*, vol. 15, No. 8, p. 16, Aug. 1988.

Franchi, Imperato and Prampolini, "Multimedia Perspectives for Next Generation PAC Systems," *Proceedings of Computer Based Medical Systems*, IEEE Press, pp. 156–169, 1992.

Executone Infostar/ILS Brochure, 1993.

PCT Search Report.

PATIENT STATION MAIN LOOP

CALL NURSE STATION

STORE DATA IN DESIGNATED MEMORY AREA

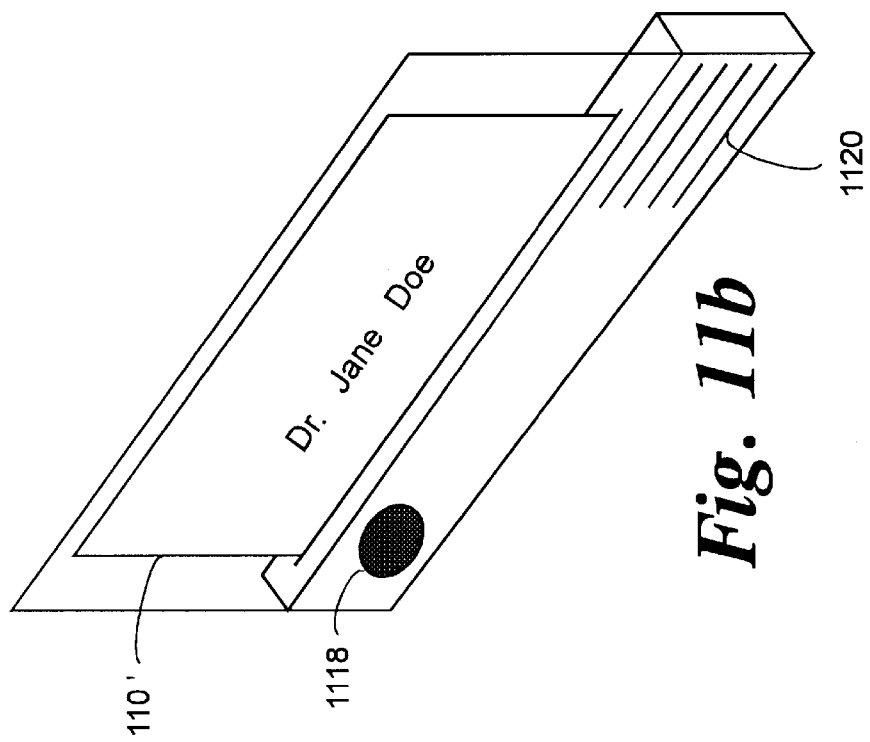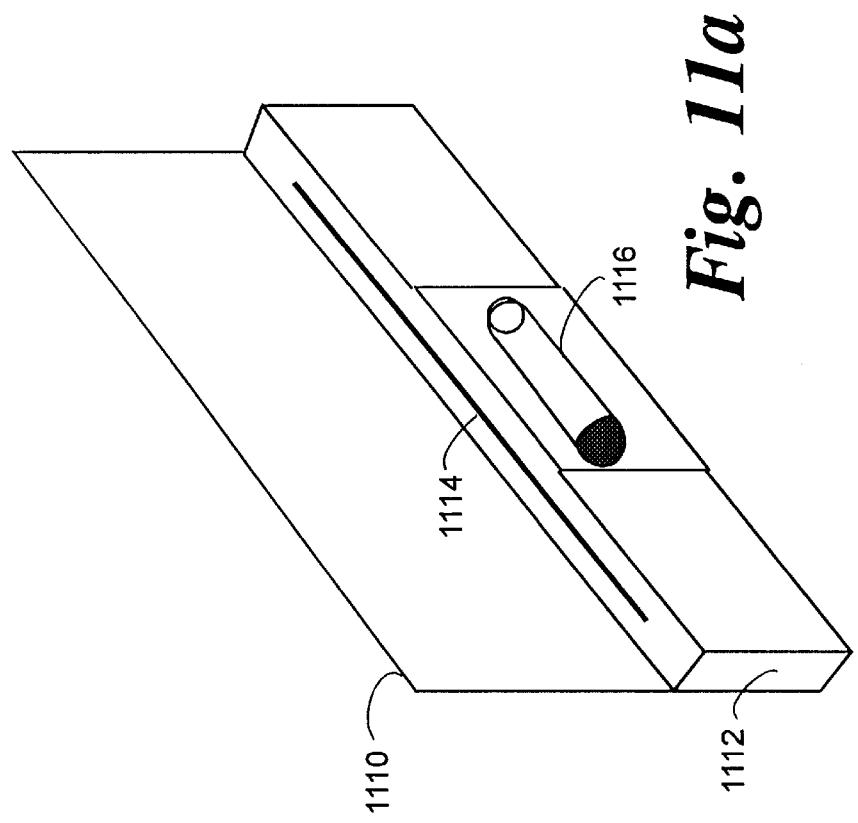

BADGE TRANSMITTER PROCESS

STATIONARY TRANSCEIVER PROCESS

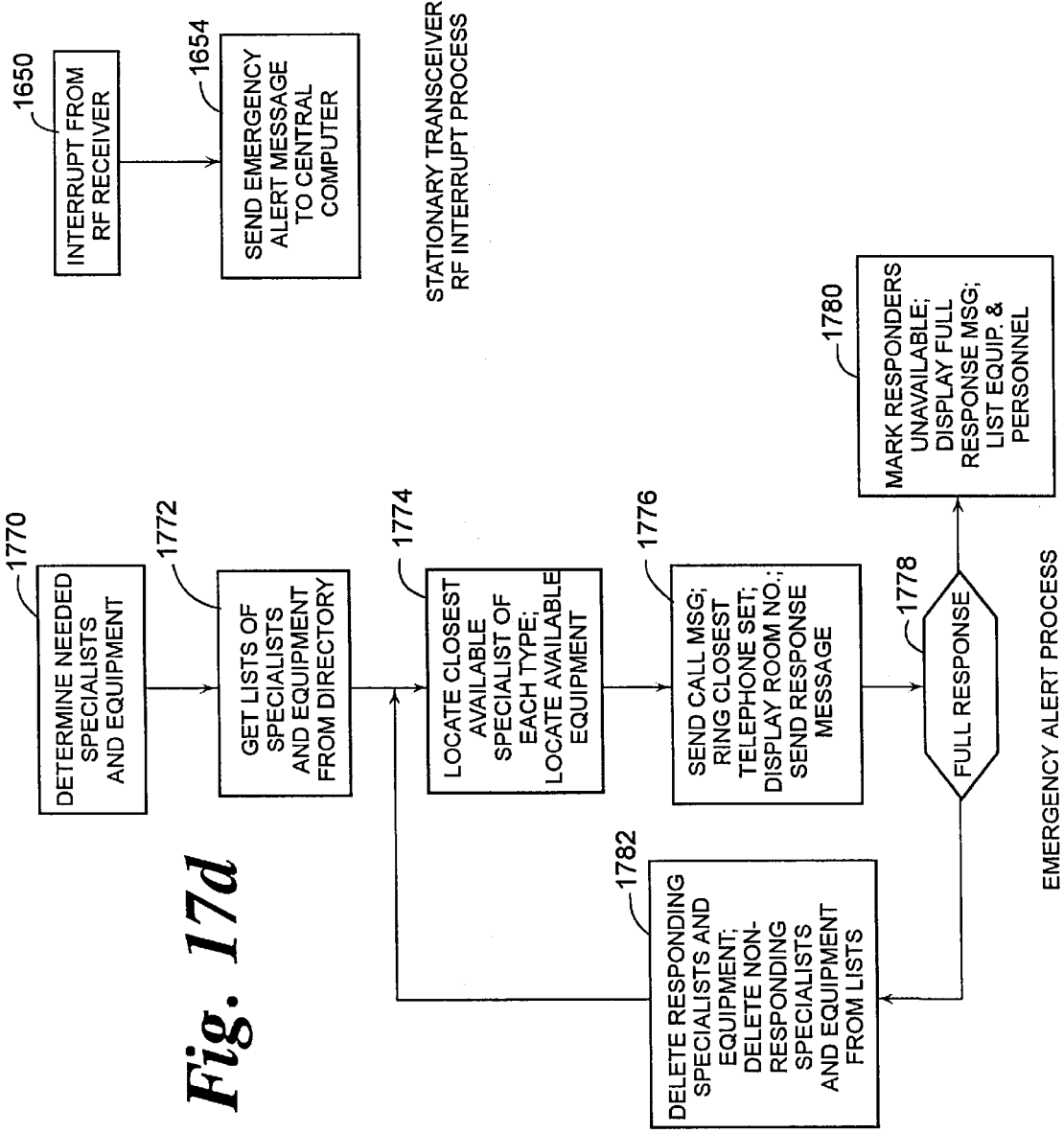

LOCATOR PROCESS

DRUG MONITOR SYSTEM - DRUG LOCKER

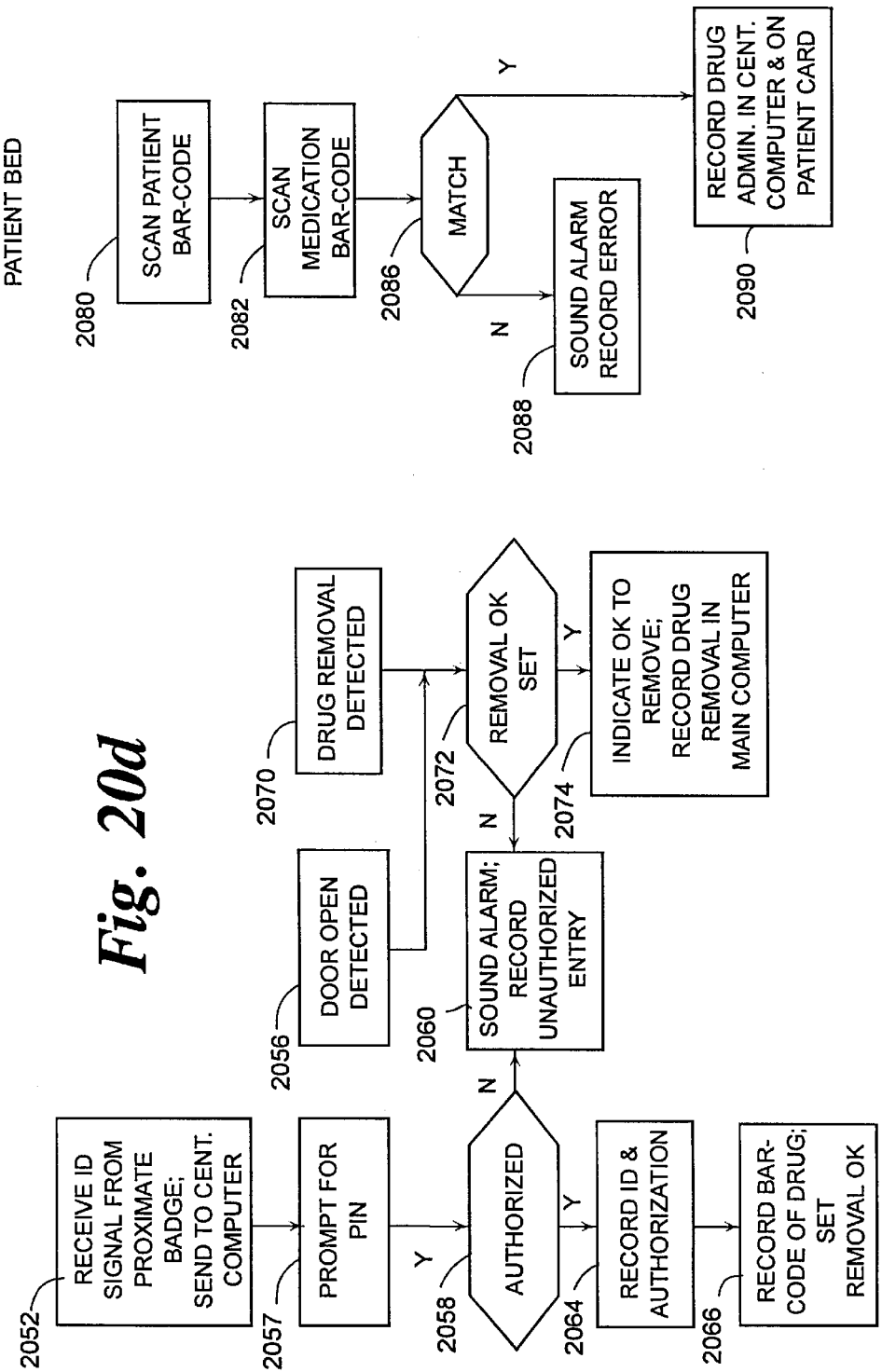

Call Indications at Nurse Control Stations

| Call Priority Level | Arrow Flash Rate in Pulses Per Minute (PPM) | Incoming Call Display Room-Bed Displayed on NCS Display 3272 | Call Level Displayed on NCS Display 3272 | Tone Signaling in Pulses Per Minute (PPM) |
|---|---|---|---|---|
| 1 Smoke Detector Call | 120 | yes-no | SMOKE DETECTOR | 120 |
| 2 Code Blue Call | 120 | yes-yes | CODE BLUE | 120 |
| 3 Staff Assist Call | 60 | yes-no | STAFF ASSIST | 60 |
| 4 Emergency Call | 60 | yes-no | EMERGENCY | 60 |
| 5 Patient Priority | 60 | yes-yes | PAT PRIORITY | 60 |
| 6 Personal Attention | steady | yes-yes | PERSONAL ATTEN | 1 @ 4PPM |
| 7 Overtime Call | 30 | yes-yes | OVERTIME | 2 @ 4PPM |
| 8 Cord Removal Call | 30 | yes-no | CORD REMOVAL | 2 @ 4PPM |
| 9 Patient Call | steady | yes-yes | PATIENT CALL | 1 @ 4PPM |
| 10 Staff Call | steady | yes-n/a | STAFF CALL | 1 @ 4PPM |
| 11 Auxiliary Device Call | 30 | yes-no | AUX DEV 1 CALL | 2 @ 4PPM |
| 12 Auxiliary Device Call | 30 | yes-no | AUX DEV 2 CALL | 2 @ 4PPM |

*Fig. 41*

Call Indications at Patient Stations

| Call Priority Level | Visual Indications | | | Tone Signaling in Pulses Per Minute (PPM) | Zone Indicator Assembly Group Indicator Color/Rate (PPM) |
|---|---|---|---|---|---|
| | Station Call Placement LED Indicator on Patient Stations (not shown) in PPM | Bed Call Placement LED Indicator on Patient Stations (not shown) in PPM | | | |
| 1 Smoke Detector Call | 120 | no | | 120 | Red/120 |
| 2 Code Blue Call | 120 | 120 | | no | Blue/120 |
| 3 Staff Assist Call | 60 | no | | no | White/60 |
| 4 Emergency Call | no | no | | no | White/60 |
| 5 Patient Priority | 60 | 60 | | single tone burst | White/60 |
| 6 Personal Attention | steady | steady | | single tone burst | White/steady |
| 7 Overtime Call | 30 | 30 | | no | Grn.-Amb./60-30 |
| 8 Cord Removal Call | 30 | no | | no | White/30 |
| 9 Patient Call | steady | steady | | single tone burst | White/steady |
| 10 Staff Call | n/a | n/a | | n/a | White/steady |
| 11 Auxiliary Device Call | 30 | no | | no | White/30 |
| 12 Auxiliary Device Call | 30 | no | | no | White/30 |

Fig. 42

Call Indications at Staff Stations

| Call Priority Level | Visual Indications | | | Tone Signaling Pulses Per Minute (PPM) | Zone Indicator Assembly (3022) Group Indicator Color/Rate (PPM) |
|---|---|---|---|---|---|
| | Incoming Call LED Indicator on Staff Station (not shown) (PPM) | Room-Bed Displayed on Staff Station Display 2422 | Call Level Displayed on Staff Station Display 2422 | | |
| 1 Smoke Detector Call | 120 | yes-no | SMOKE DETECTOR | 120 | Red/120 |
| 2 Code Blue Call | 120 | yes-yes | CODE BLUE | 120 | Blue/120 |
| 3 Staff Assist Call | 60 | yes-no | STAFF ASSIST | 60 | White/60 |
| 4 Emergency Call | 60 | yes-no | EMERGENCY | 60 | White/60 |
| 5 Patient Priority | 60 | yes-yes | PAT PRIORITY | 60 | White/60 |
| 6 Personal Attention | steady | yes-yes | PERSONAL ATTEN | 1 @ 4PPM | White/steady |
| 7 Overtime Call | 30 | yes-yes | OVERTIME | 2 @ 4PPM | Grn.-Amb./60-30 |
| 8 Cord Removal Call | 30 | yes-no | CORD REMOVAL | 2 @ 4PPM | White/30 |
| 9 Patient Call | steady | yes-yes | PATIENT CALL | 1 @ 4PPM | White/steady |
| 10 Staff Call | steady | yes-n/a | STAFF CALL | 1 @ 4PPM | White/steady |
| 11 Auxiliary Device Call | 30 | yes-no | AUX DEV 1 CALL | 2 @ 4PPM | White/30 |
| 12 Auxiliary Device Call | 30 | yes-no | AUX DEV 2 CALL | 2 @ 4PPM | White/30 |

*Fig. 43*

PATIENT CARE AND COMMUNICATION SYSTEM

CROSS REFERENCE TO RELATED APPLICATIONS

This is a continuation of application Ser. No. 08/033,287 filed on Mar. 16, 1993, now abandoned, which is a continuation-in-part of application Ser. No. 07/924,101 filed on Aug. 3, 1992, now U.S. Pat. No. 5,465,082, which is a continuation-in-part of application Ser. No. 07/559,196 filed on Jul. 27, 1990, now U.S. Pat. No. 5,291,399.

BACKGROUND OF THE INVENTION

1. Field of the Invention

The present invention relates to a patient care and communication system, more particularly, a system capable of performing tasks such as monitoring medical equipment in patient rooms and maintaining patient medical data; facilitating staff-to-staff or staff-to-patient voice, visual and data communications; and tracking the location of staff members to provide maximum patient care.

2. Description of the Related Art

In hospital or other health care environments, the nursing staff as well as other staff members are required to maintain and update patient information, provide patient care, and assist physicians in the treatment of patients. Often, these tasks have to be performed even though there are personnel shortages. Further, as medical technology continues to develop to provide treatment for a greater number of medical conditions, the volume of information that is maintained for each patient continues to grow rapidly. As a result, stress on the nursing staff has increased and information overload is fast approaching.

To more fully understand the above problem relating to health care, consider the types of data which are maintained for an individual patient. Typically, the staff members need to know the patient's name and address as well as any special dietary, environmental or physical space requirements of the patient. The attending physician or nursing staff may want to know the patient's condition, medical history and recent vital sign data. If the patient has had any diagnostic tests such as x-rays or ultrasound images made at the hospital, or at any other hospital, the attending physician may want to compare these test results with the results of newer tests to see how the patient's condition has progressed. In addition, if any medication has been prescribed, the physician or nursing staff may want to know the identity of the medication, when the last dose was taken and how the patient has complied with the dosage schedule.

Current systems utilized to manage such information includes the manual writing and processing of the information. Electronic systems utilized to process and store the information involve multiple computers, each configured to process portions of the vast amount of information. To obtain all the information in one place the information stored in each computer system must be manually combined. Furthermore, such electronic systems do not provide visual displays of text at stations provided in the patient's room, at the nurse control station or at stations provided in areas of the health care facility frequently occupied by the health care personnel.

In addition to processing the above information, the nursing staff attending to a number of patient's rooms may want to have some indication of each patient's condition at nursing stations which are far removed from the patient's bed. For example, if the patient has been admitted for a heart condition, it would be helpful if any recent vital signs that may indicate the onset of a heart attack could be displayed at the nurses station when the patient presses a call button.

Another problem faced by care givers and by hospital administrators is determining the location of key personnel and equipment. In an emergency or during periods of personnel shortages, the ability to quickly locate an attending physician or other staff member to provide maximum patient care is desirable. Moreover, when special equipment is required to treat an emergency condition or when a ward of a hospital is experiencing personnel shortages, it is desirable that the equipment be quickly located to reduce the time spent to locate the equipment.

One type of system utilized to locate personnel within a hospital or other health care facility relies on audio paging systems, sign-in and sign-out sheets and broadcast paging systems. In a given situation, the audio paging system would be tried first. This system may not be effective if the person to be located is in an area where the paging system is not functioning properly or has been turned down, or if the person has left the hospital. After an unsuccessful audio page, the sign-in and sign-out sheets may be checked. If, however, the person to be located forgot to use the sign-in sheet or sign-out sheet, critical time may be lost in a second attempt to use the audio paging system. In addition, a search of the sign-in and sign-out sheets may require more time than is available in an emergency situation.

When the person to be located is outside of the hospital, broadcast paging systems are often the best way to convey an important message. These systems require the individual trying to locate the person to call the paging service, leave a message, wait for the paging service to send the message to the individual's pocket pager and then wait for the person being paged to call the paging service, receive the message and respond.

Another type of currently used locator system utilizes either radio frequency signals or infra-red signals to communicate the position of a mobile individual or object to a network of receivers. Once such system, the InfraCom locating and signaling system available from United Identification Systems Corp. is designed for use in a hospital environment. Using this system, a network of infra-red transceivers located throughout a hospital can both transmit data to and receive data using a battery operated badge worn by hospital personnel or attached to the equipment to be located. This badge transmits a programmed identification signal to the network allowing the position of the badge to be indicated on a floor plan of the hospital.

Another exemplary system, the TELOC PLUS personnel locator system available from Teloc, Inc., also uses two-way infra-red signaling to communicate the position of a battery powered badge in a distributed sensor network. In addition, the Teloc system may be coupled to a private branch exchange (PBX) to allow telephone calls from an individual to be routed to the telephone that is closest to the badge or to direct an intercom message to that telephone, thus providing an alternative to an audio paging system. Each of these systems is limited in the data that may be conveyed between the stationary transceiver network and the transceiver on the badge. In the described systems, only identification information lend an indication that switches, which are located on the badge, have been activated may be transmitted from the badge. Furthermore, if the transceiver on the badge fails or is damaged, a blank badge must be programmed to take its place. This program operation may be time consuming, leaving the individual or the piece of equipment invisible to the locating system for that period of time.

However, none of the above described patient information processing systems integrate a staff locating system with a system which facilitates audio, visual and data communications between staff members and patients and which maintains patient data. Accordingly, a need exists for a patient care and communication system capable of performing tasks such as monitoring medical equipment in patient rooms and maintaining patient medical data, facilitating voice, visual and data communications between staff members and the patients, as well as a system for tracking staff members to provide maximum patient care.

SUMMARY OF THE INVENTION

The present invention provides a patient care and communication system which comprises central processing means for facilitating audio, visual and data communications and a plurality of remote stations electrically connected to the central processing means. The remote stations include processing means for facilitating the audio, visual and data communications and display means for displaying the visual communications.

The central processing means of the present invention facilitates the audio, visual and data communications between the plurality of remote stations, and includes means for determining which of the plurality of remote stations are transmitting the audio, visual and data communications and which of the plurality of remote stations are to receive said audio, visual and data communications, and means for establishing a communication link between the transmitting stations and the receiving stations.

Preferably, the plurality of remote stations includes control stations, patient stations and staff stations and the central processing means includes means for directing said audio, visual and data signals transmitted to said control stations to a predetermined number of said patient stations and a predetermined number of said staff stations.

The present invention also includes a patient care and communication system where the plurality of remote stations are configured and adapted for association in a group network such that predefined audio, visual and data signal communications are transmitted to each station in the group. Zone controller means are provided to interface the central processing means to the transmitting and receiving stations.

In the preferred embodiment, the central processing means also includes means for activating audio communication between control stations, and a predetermined number of the patient stations and a predetermined number of the staff stations, means for facilitating activation of a code blue function from control stations means for activating audio communications between the control stations and a predetermined number of the patient stations to facilitate audio monitoring of patient rooms from the control stations, and means for prioritizing visual and data communications to said control stations so as to organize the response of staff members.

Each of the plurality of remote stations includes means for performing diagnostic tests on peripheral equipment connected thereto. The diagnostic tests include performing wire continuity checks and using comparators to verify that indicator lamps are operational.

The patient stations of the system of the present invention, include patient control means electrically connected thereto. The patient control means, preferably, including means for verifying the continuity of conductors connected between the patient stations and the patient control means and means for controlling environmental facilities within a patient's room.

The system of the present invention also relates to a method of providing patient care and communication between patient rooms and nurse stations in a health care facility. The method includes the step of connecting a plurality of remote stations to a central processor so as to facilitate audio, visual and data communications therebetween, positioning at least one of said plurality of remote stations in each patient room located within the health care facility, positioning at least one of said plurality of remote stations in each nurse station of said health care facility, attending said remote station in each nurse station to receive said audio, visual and data signals from said central processor and responding to said audio, visual and data signals.

Preferably, the plurality of remote stations include processing means for facilitating the audio, visual and data communications and display means for displaying the visual communications. The central processor includes means for determining which of the plurality of remote stations are transmitting the audio, visual and data communications and which of the plurality of remote stations are to receive the audio, visual and data communications, and means for establishing a communication link between the transmitting stations and the receiving stations.

BRIEF DESCRIPTION OF THE DRAWINGS

The preferred embodiments of the invention are described hereinbelow with reference to the drawings wherein:

FIGS. 5 through 10 are flow-chart diagrams which illustrate the operation of the patient station shown in FIG. 2;

FIGS. 11a and 11b are perspective drawings of a portable transceiver unit suitable for use with the present invention;

FIGS. 16a and 16b are flow-chart diagrams which illustrate the operation of the transmitter receiver unit shown in FIG. 15;

FIGS. 17c and 17d are flow-chart diagrams which illustrate the use of the system as a personnel and equipment locator and for handling an emergency alert condition;

FIG. 20b is a block diagram of a drug locker monitoring system suitable for use with the drug locker shown in FIG. 20a;

FIG. 20d and 20e are flow-chart diagrams which illustrate the operation of a drug auditing system using the drug locker monitoring system shown in FIG. 20b and the patient station in FIG. 4;

FIG. 21b is a flow-chart diagram which illustrates the operation of a student-advance electronic funds transfer system which may be implemented on the student information system shown in FIG. 21a;

FIGS. 41, 42 and 43 are tables which illustrate various call indications and associated tones generated by the stations in response to a particular call condition;

DETAILED DESCRIPTION OF THE PREFERRED EMBODIMENTS

Generally, the patient care and communication system of the present invention includes a communication network that provides routine and emergency signaling to health care facility staff members and provides high fidelity voice communication and data transmission between staff members in the health care facility and/or between patients and the staff members.

The exemplary embodiments of the automatic staff locator system of the patient care and communication system of the present invention described below, use a memory card as a personal database. As used herein, a memory card is a device approximately the same size and shape as an ordinary credit card which includes a non-volatile programmable memory. In the card used in the embodiments described below, two types of memory are used: an electronically erasable read only memory (EEROM) located internal to the card and a magnetic stripe located on the surface of the card. It is contemplated, however, that other forms of internal memory, such as a ferro-electric RAM or a CMOS memory with an integral battery, may be used. It is also contemplated that the functions described below may be implemented with other types of external memory, such as laser card technologies which either augment or replace the card memory.

Figure 13:
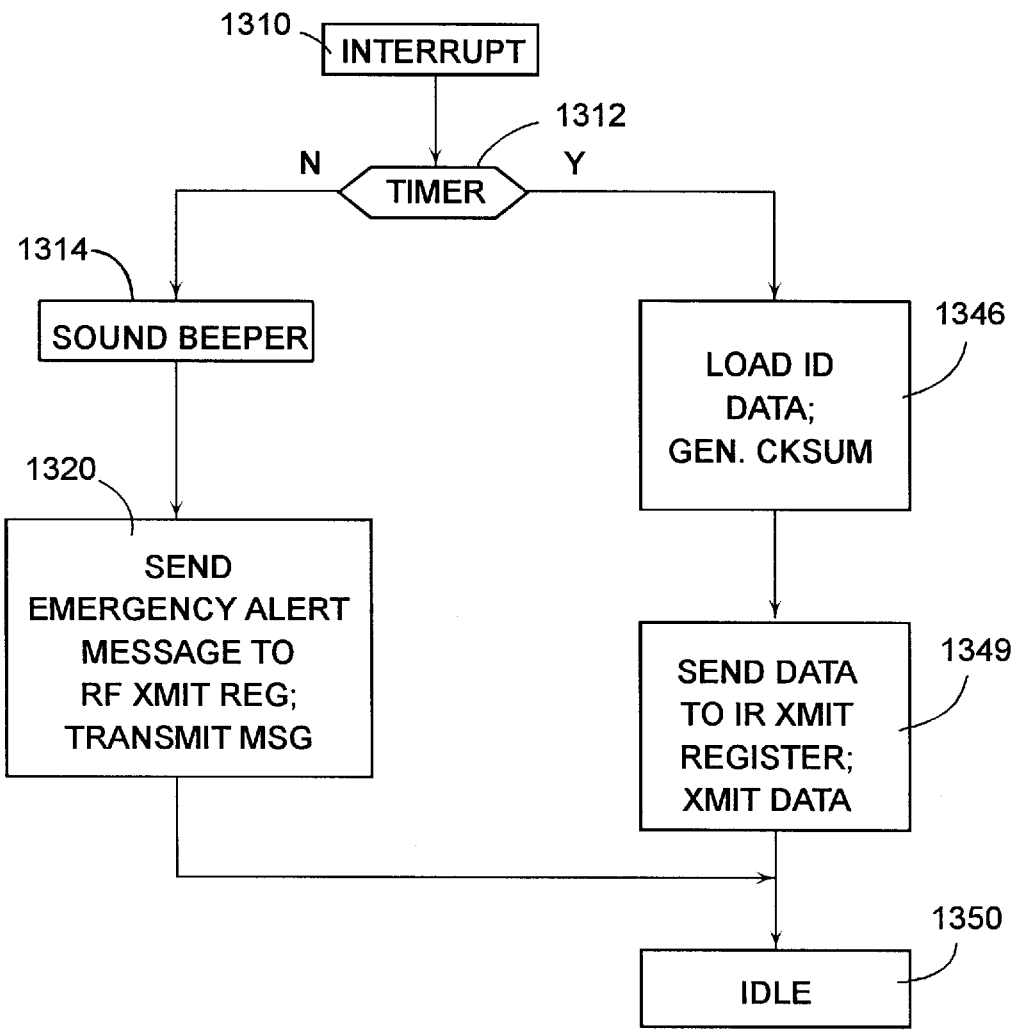
FIG. 13 is a flow-chart diagram which illustrates the operation of the portable transceiver unit shown in FIG. 12.
Figure 22:
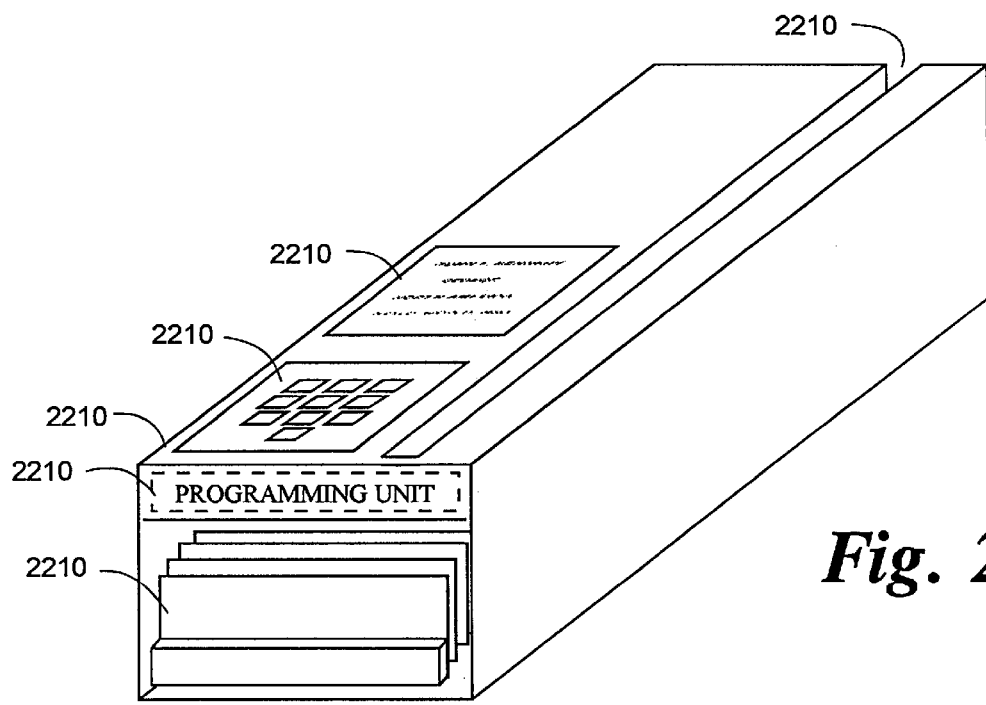
FIG. 22 is a perspective drawing of an exemplary base unit suitable for use with the portable transceiver units shown in FIGS. 11a and 11b.

A first embodiment of the staff locator system described below uses the memory card to augment features that may be provided by a transmitter, which may appear as an identification badge. FIGS. 11a and 11b show typical transmitters which are removably coupled to the memory card. A memory card contains, for example, the name of the medical staff worker who is to wear the badge, the individual's authorization code, and other information. In this embodiment, the identification badge/transmitter is unable to transmit the information contained by the memory card unless it is effectively mated with a memory card by a base unit, as shown in FIG. 22. In FIG. 13 the sequence of how the identification badge transmitter transmits an identification signal is detailed. Using these badges, a ubiquitous network and a central computer, medical staff can quickly and easily be located.

Another embodiment described below involves the use of the memory card to again be coupled with an identification badge transmitter to continually transmit an identification signal. A fixed receiver, responsive to the identification signal, is installed near a secured area. This fixed receiver has means for receiving the ID information and automatically determining the identity of any individual within a predetermined distance and determining whether that individual is authorized, as shown in the sequence of steps of FIG. 20d. This system automatically records the identity of the person removing the drugs and the drugs that are removed. In addition, the system records when the drugs are administered and the identities of the patients to whom they are given.

Figure 1A:
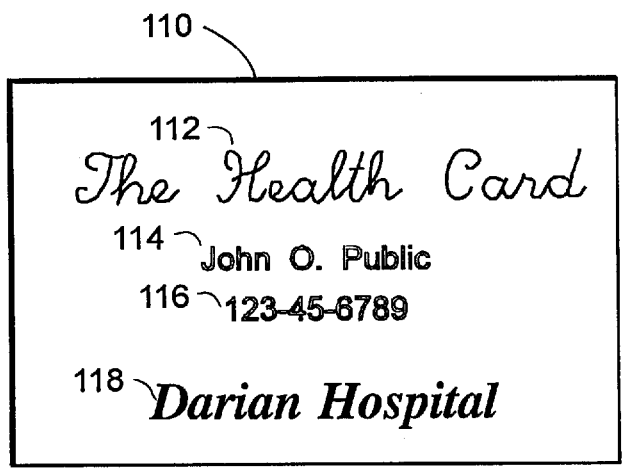
FIGS. 1a and 1b are respective front plan and back plan drawings of a personal database suitable for use in the present invention.
Figure 1B:
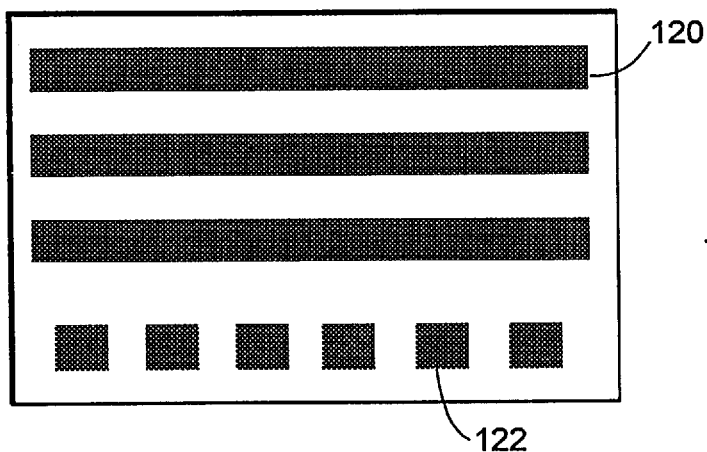

The memory card 110 used with these exemplary embodiments of the invention is illustrated in FIG. 1a and 1b. As shown in FIG. 1a, the card 110 is approximately the same size and has the same physical characteristics as an ordinary credit card. The front of the card may include a printed logo, 112, which identifies the provider of the card, identifying information such as the person's name, 114 and ID number 116, as well as a legend, 118, identifying the hospital that issued the card.

The back of the card may include auxiliary, external data storage 120 and electrical contacts 122 for interfacing with the internal circuitry of the card. The auxiliary data storage 120 may include magnetic stripes, as shown in FIG. 1b, or a medium compatible with a laser card device. The electrical contacts 122 may be in the form of external or internal ohmic contacts, or electromagnetic contacts, such as are disclosed in U.S. Pat. No. 4,798,322 to Bernstein et al. CARD READER/WRITER STATION FOR USE WITH A PERSONAL MEMORY CARD USING DIFFERENTIAL DATA TRANSFER.

An exemplary memory card, which uses ohmic contacts and does not have any auxiliary data storage is the memory card component of the PC3™ system available from PC3 Inc. This exemplary memory card includes 16,384 (16k) bytes of EEROM. The exact format of the data on the card is unimportant for this description of the invention since it would change with the application.

A second exemplary memory card uses only the auxiliary data storage and has no ohmic contacts or internal data storage. This card may be any of a number of commercially available cards which include a magnetic stripe.

The memory card is a portable database of information. For purposes of this description, the card has two embodiments, although others are possible. First, the card is a database containing only identifying information about a hospital employee—a staff worker. In this embodiment, the card will hereinafter be called a "staff card." Second, the card is a database containing identifying and other information about a patient at the hospital. In this embodiment, the card will be called a "patient card."

A patient card should include information such as the patient's name, address and telephone number, her age and blood group, an indication of any chronic condition from which she suffers and any allergies that she may have. In addition it should indicate the name and address of her personal physician, the date of her most recent tetanus shot, and the identity and dosage schedule of any prescribed medicine. For most patients, all of this information may be recorded in 2k bytes of, storage. For cards having internal memory, this data may be stored on the card itself. For cards having only external memory, this data may be stored in a database which is indexed using information stored on the card. This data base may be located in a computer near the patient's bed or in a centrally located main computer. In this configuration, the patient card, like the staff card, only includes identification information, which may be used to access the remaining patient information from the local or main computer.

As shown in FIG. 1b, it is contemplated that the card may also include auxiliary storage such as a laser recording medium. This storage may be used to hold digitally compressed radiographic images or other data that cannot feasibly be stored in the card memory.

Figure 1D:
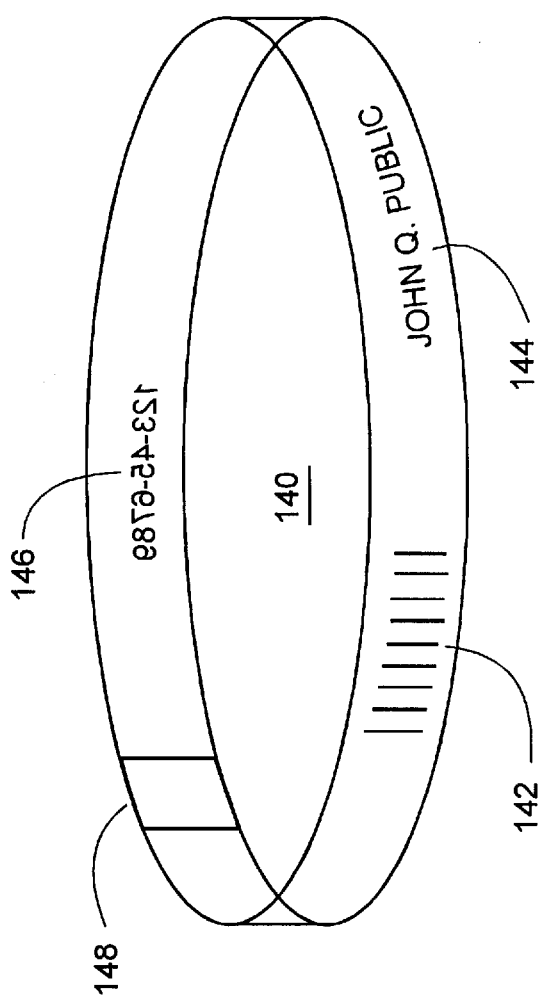
FIG. 1d is a perspective drawing of a patient wrist band.

One useful piece of information that may be stored in the card is a bar-code ID number. This number is stored onto the card from a bracelet that is attached to the patient so that it is difficult to remove. An exemplary bracelet of this type is shown in FIG. 1d. The bracelet 140 also includes the patient's name, 144, and ID number 146. The bracelet is configured to be closed, using a clamp 148, around the wrist or ankle of the patient so that it cannot be slipped over the patient's hand or foot, respectively. The use of the bar-code information is described below in reference to FIGS. 9 and 20e.

Figure 1C:
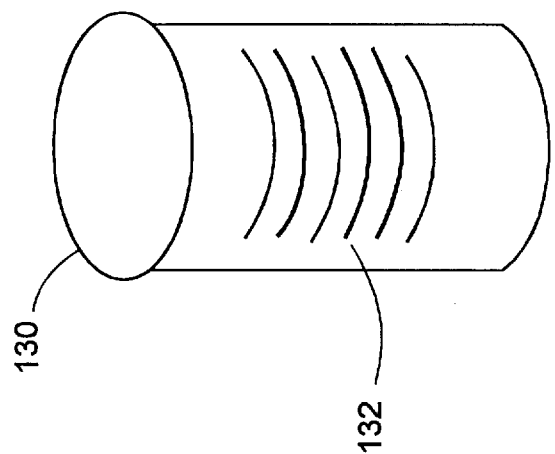
FIG. 1c is a perspective drawing of a medicine container.

Another component of the system is a bar-code 132 that is placed on medication containers 130, as shown in FIG. 1c. This bar-code is used, as described below in reference to FIGS. 9 and 20e to identify medicines to the central computer to ensure that the proper medicine is being administered to the patient and to audit the use of controlled substances in the hospital.

FIGS. 11a and 11b illustrate a mobile interface suitable for use with a staff card. This interface includes both an infra-red (IR) transmitter and a radio frequency transmitter which can transmit data to a one of a group of stationary receivers or transceivers located at various places in the hospital. Transmitters and receivers suitable for use with the present invention are available from Wilton Industries of Connecticut.

The database interface shown in FIGS. 11a and 11b is a card holder 1111 which, when enabled by a base unit, converts a staff card 110' into an identification badge. The interface includes a clear plastic front piece, 1110, which protects the memory card 110' and through which information printed on the front of the card may be seen. The front piece 1110 is attached to a holder 1112 which includes all of the electronic components of the database interface. The base includes a fastener 1116, shown in the exemplary embodiment as a safety pin, which is used to-attach the card holder to an article of clothing, such as the sleeve or pocket of a nurse's uniform.

The memory card 110' is inserted into a slot 1114 in the holder 1112 to make physical contact with the holder 1112. If a memory card 110' having internal memory is used, it may also make electrical contact with the holder 1112. The holder 1112 includes a push-button switch 1118 through which the person wearing the badge may signal a response to the stationary system or activate an emergency transmission mode.

When disabled, card holder 1111 cannot cooperate with staff card 1110 to form an entity capable of transmitting-an identification signal. A base unit, shown in FIG. 22, enables card holder 1111 by reading data from staff card 1110 and programming it to card holder 1111. This permits card holder 1111 to cooperate with staff card 1110 to form an entity capable of transmitting identification information.

As shown in FIG. 22a base unit 2210 has a slot 2214, through which staff card 110' may be passed. Transducers located along slot 2214 read data from staff card 110' and writes it into memory in the card holder 1111 by means of an programming unit 2212. Unit 2212 is located in the base unit 2210 and is electrically coupled to card holder 1111 which will be next removed from the base unit 2210.

The base unit may be rectangular in shape and may contain one or many card holders 1111. However, only one card holder at a time is programmed with the information from a staff card 110. After card holder 1111 is programmed with the data from the staff card 110', an individual may easily remove it from base unit 2210 and couple it to the card 110' by inserting the card into the slot 1114, shown in FIG. 11. In the exemplary embodiment of the invention, if the card 110' is not inserted within 45 seconds of when the holder 1111 is removed from the base unit, the card holder will become inactive and will, instead, emit a periodic tone pulse to indicate that the card holder is inactive.

As shown in FIG. 22, the base unit may also include a key pad 2218 and screen 2220. The screen provides instructions for the user and the keypad adds security to the system by requesting a personal identification number (PIN) before programming the card holder 1111.

Prior to inserting a staff card into slot 2214, screen 2220 reads: "Slide card through slot," or a similar message. After sliding staff card 110 through slot 2214, screen 2220 may prompt for a PIN. In response to this message, the individual enters his or her personal identification number. Only if the entered personal identification number matches the personal identification number stored on staff card 110 and, optionally, in the central computer, will base unit 2210 impart the data from the staff card to card holder 1111 and activate the holder.

If the entered PIN does not match the PIN read from the staff card, an alarm may be sounded and the information from the card may not be programmed onto the card holder. In this way, the likelihood that an unauthorized person could use a stolen staff card is decreased and the security of the apparatus is increased. To prevent unnecessary alarms, it may be desirable to sound the alarm only after the individual has entered an incorrect wrong PIN a number of times in succession. Alternatively, instead of sounding an alarm, the base unit may be designed to automatically transfer the card from the programming slot 2214 to a secure holding area (not shown) when the individual has failed to provide a correct PIN after a number of attempts.

When the programmed staff card holder 1111 is has been mated to the staff card 110', the result is an entity capable of continually transmitting an identification signal. This signal is transmitted to receiver or transceiver units located in fixed locations each open area or room of the hospital. These units are electronically coupled to a central computer to form a network. Using this system, medical staff can quickly and easily be located, as described below with reference to FIG. 17c.

The exemplary card holder 1111 includes an internal switch (not shown) which is activated when the memory card 210 is inserted. Responsive to this switch, the card holder will remain enabled for up to 9 hours after the card is inserted. The holder will be disabled, however, if the card is removed and, so, the switch is deactivated for a period of at least 45 seconds. Whenever the card holder 1111 is disabled, for the reasons described above or because its internal battery is failing, it emits a periodic tone pulse through the speaker 1120, shown in FIG. 11b, to alert the wearer that a new card holder must be obtained.

Figure 4:
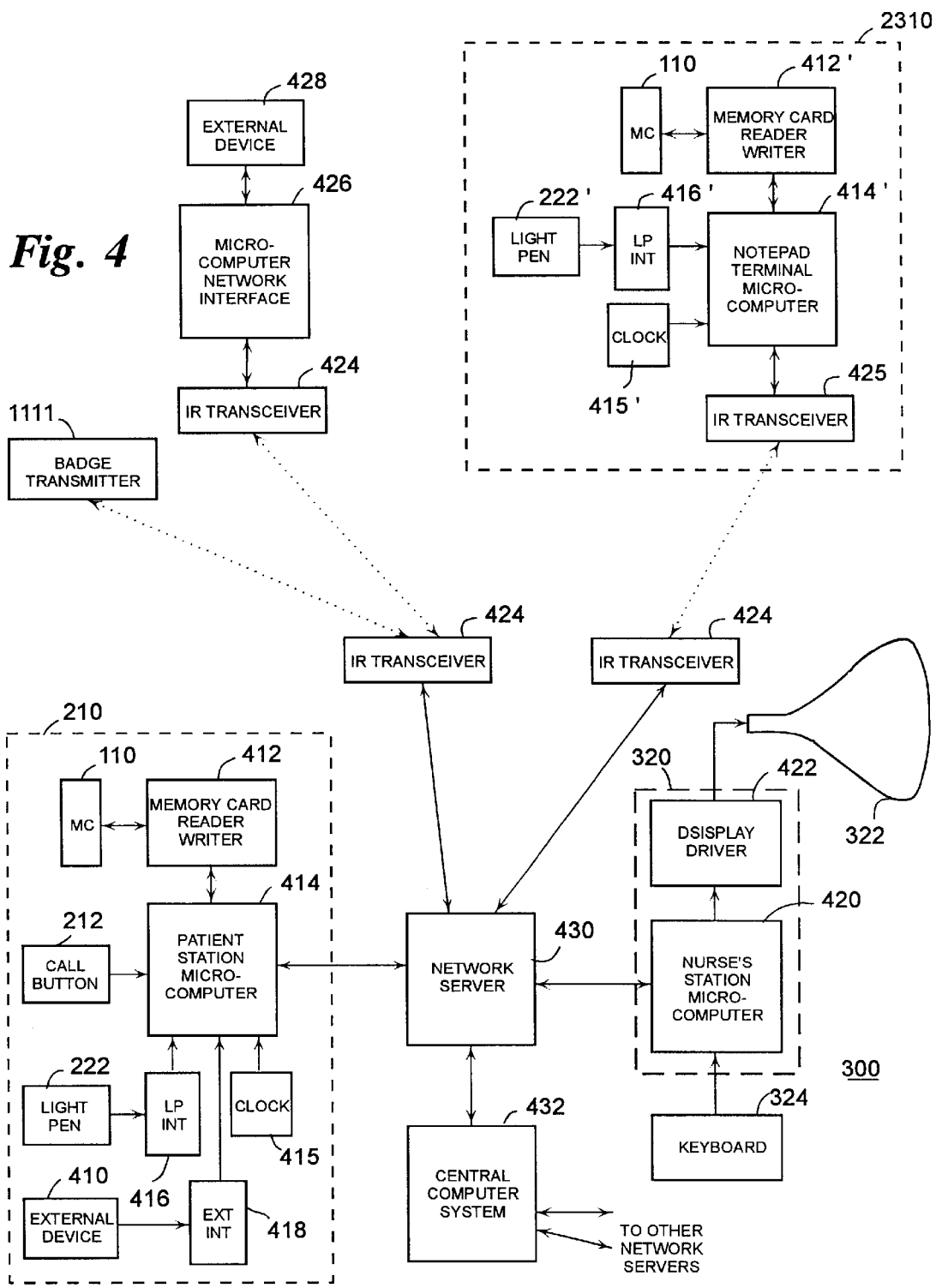
FIG. 4 is a block diagram showing the functional connectivity of the patient station and central nurse station shown in FIGS. 2 and 3.

As the enabled identification badge continually transmits its identification signal, it can be particularly useful as a locating device. For use as a locating device, the identification badge is linked by some means to a central computer. As shown in FIG. 4, identification badge transmitter 1111 sends signals to a fixed receiver or transceiver 424 which is in communication with a central computer 432 through a network server 430. This configuration is described in more detail below. For this aspect of the invention, however, it is only important to realize that identification badges 1111 are in communication with the central computer 432.

Figure 2:
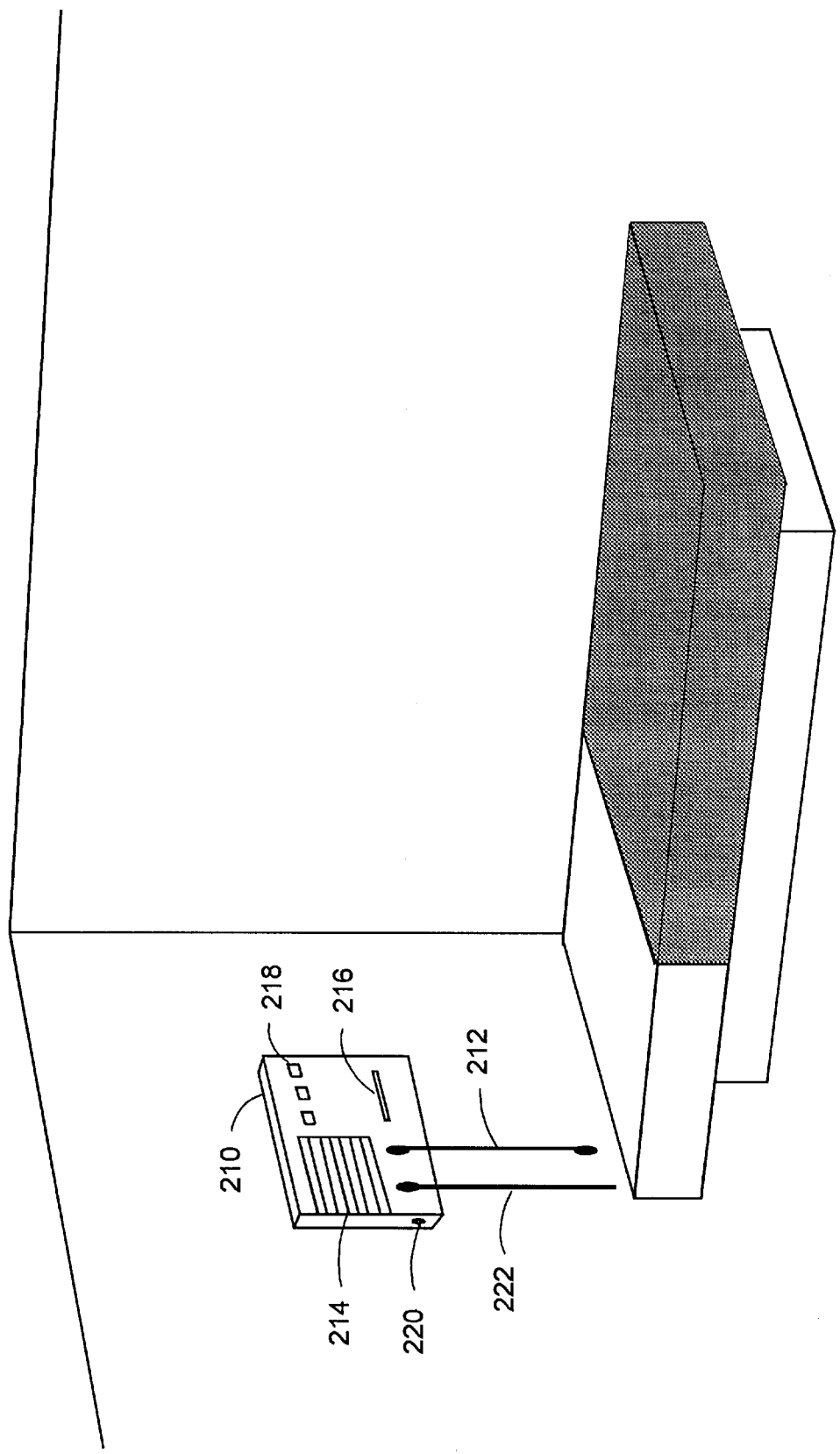
FIG. 2 is a perspective drawing of a portion of a patient room which includes a patient station suitable for use in the present invention.

An exemplary configuration for the patient's patient station is shown in FIG. 2. The exemplary patient station 210 includes a slot 216 into which the memory card 110, preferably a patient card, may be inserted and a squeeze bulb 212, which, when squeezed, alerts the duty nurse at the central nurse station that the person in the bed needs assistance. In addition, the patient station may include a speaker 214 through which the duty nurse may both talk to and listen to the patient, push button switches 218, one of which may be used to cancel a call, a light pen 222 for reading the bar-codes such as those on the wrist band and on the medication, one or more external data inputs 220 which may be used to supply vital sign data to the central nurse station.

Figure 3:
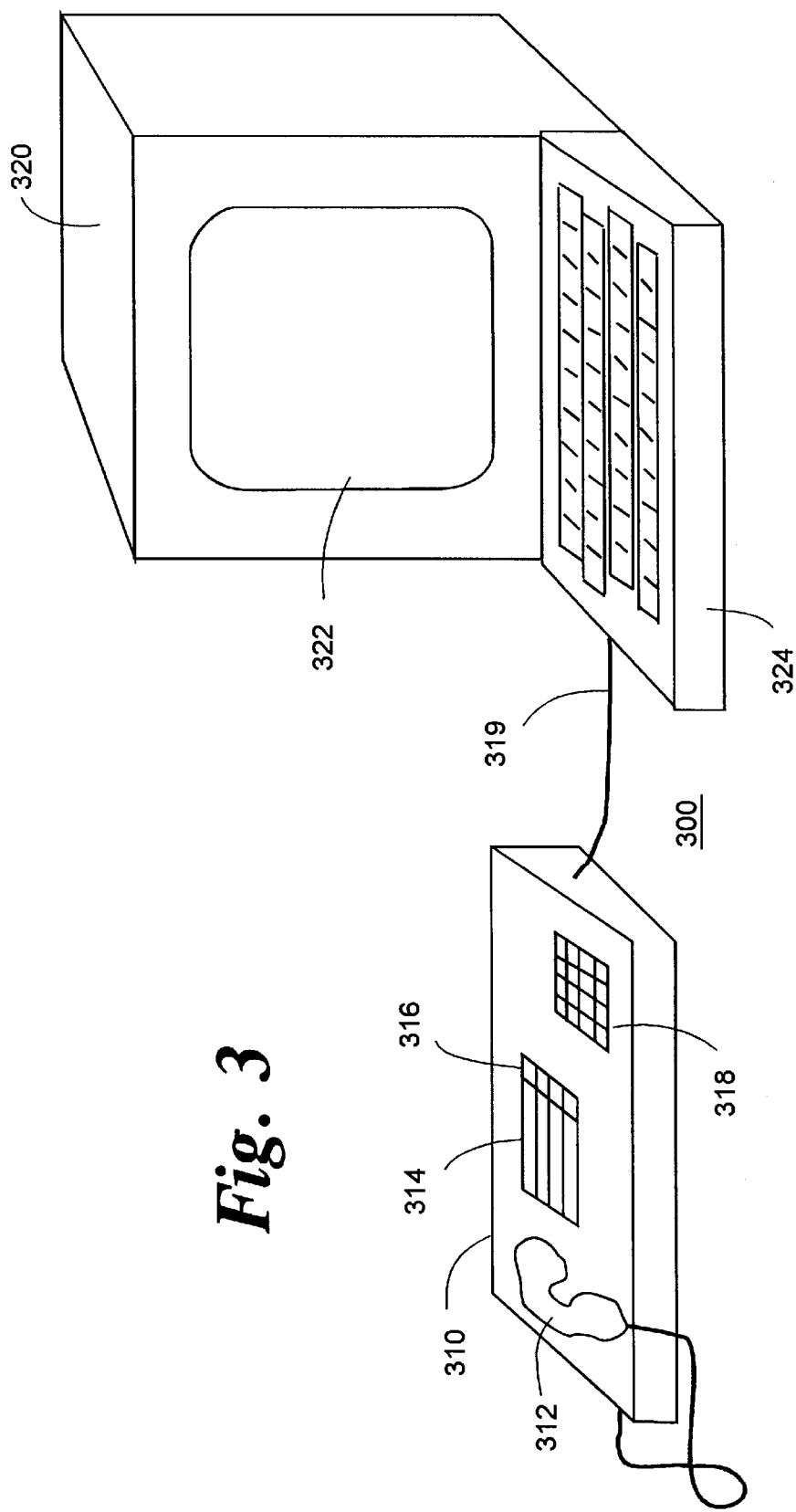
FIG. 3 is a perspective drawing of a central nurse station suitable for use with the present invention.

An exemplary central nurse station 300 is illustrated in FIG. 3. The central component of the nurse station is a microcomputer terminal 320. This may be, for example, a conventional IBM compatible personal computer.

Data indicating, for example, which patients have called and their relevant vital signs may be displayed on a video screen 322 of the microcomputer 320. Patient data, such as prescribed medication or dietary menu choices, may be entered into the central computer using the keyboard 324 of the microcomputer terminal 320. As set forth below, this data may also be stored locally at the patient station or, depending on the type of memory card used, stored in the patient's memory card.

Figure 23:
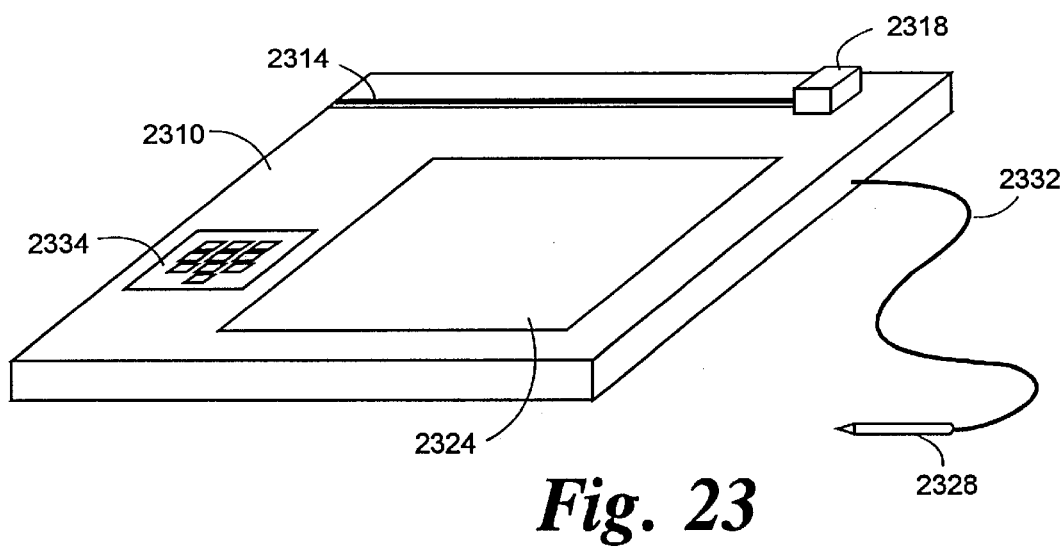
FIG. 23 is a perspective drawing of a portable nurse station suitable for use with the network shown in FIGS. 4 and 14.

An exemplary nurse notepad terminal is illustrated in FIG. 23. Nurse notepad 2710 includes an internal microcomputer (not shown) and an IR transceiver (not shown). Referring to FIG. 4, the notepad terminal is capable of communicating with computer 432 via the fixed transceivers located in each room of and the network servers 430 located in each floor or in each wing of each floor of the hospital.

The notepad terminal 2310 includes a slot 2314 for accepting and reading a patient card 110. As patient card 110 is slid along slot 2314, the identification and other information is read from the card and stored in the nurse notepad terminal. Clasp 2318 is a temporary holder for patient card 110. Patient card 110 is kept falling out or being confused with another by clasp 2318. Also, clasp 2318 is configured to display the individual's name 114 on the card to an operator while the card is engaged by notepad 2310.

As shown, notepad terminal 2310 includes a light-pen input device 2328. A user, such as a caregiver uses the terminal by touching the light-pen to various icons located on screen 2324. The pen 2328 is connected to the notepad by a cord 2332. The icons may include, for example, various instructions, such as obtain blood pressure, obtain time of next medication, etc. Touching icons and selecting items from menus causes the notepad unit to generate messages for the central computer 432, shown in FIG. 4, to a patient station and/or to a central nurse station. These messages are received for and sent to the network via the fixed transceivers 424 via the internal IR transceivers 425 of the notepad terminal 2710.

In one embodiment, the nurse may enters various information regarding the patient using notepad 2710. After passing patient card 110 through slot 2714, a nurse may then input such information as age, weight, smoking habits, blood pressure, cholesterol, etc. This information is then communicated to central computer 432 by being transmitted from transceiver 425 to one of the fixed transceivers 424 located in each room of the hospital and from the fixed transceivers through the network to the network server 430 and central computer 432. The fixed transceivers 424, network servers 430 and central computer 432 are linked in a hierarchical network. In the exemplary embodiment of the invention, this network operates according to a token-bus protocol such that each level controls a token which is used for communication with devices at lower levels.

Although FIG. 23 shows a light pen for communicating with the notepad terminal, it is contemplated that other means such as a keypad 2334 or a voice recognition system (not shown) could be used to enter information into the notepad terminal.

FIG. 4 is a block diagram which illustrates the functional interconnection of the various items illustrated in FIGS. 1*a*, 1*b*, 2, 3, and 23. As shown in FIG. 4, the patient station 210 includes a memory card reader/writer, 412, into which the memory card 110 may be inserted. The reader/writer 412, which may be, for example, the PC3™ memory card reader/writer available from PC3 Inc. is coupled to a patient station microcomputer 414 by a two-way data link.

The microcomputer 414 used in the exemplary embodiment of the invention uses an 80C50 microcontroller, manufactured by Intel Corp. This device includes a read only memory (ROM) program storage and random access memory (RAM) for temporary data storage. This internal memory may be augmented with external memory (not shown) The nurse call button 212 is coupled to a serial data input port of the microcomputer 414. The light pen 222 is coupled to the microcomputer 414 through a light pen interface circuit 416. A light pen interface circuit suitable for use in the patient station 210 is the PC E-Z-Reader™ 300/5G111 model available from PC E-Z-Reader Inc.

One or more external devices, such as an electrocardiogram, blood pressure monitor or respiration monitor may be coupled to the microcomputer 414 through separate external interface circuits 418. The type of external interface circuit used depends on the type of device which is to be monitored. If the device includes a standard data interface, such as an RS232 port or an IEEE 488 port, the external interface 418 may be one of the serial interface ports to the microcomputer 414. If, however, the external device 410 can only provide an analog output signal, the external interface circuit 418 may include apparatus such as an analog-to-digital converter (ADC) (not shown) to develop digital samples representing the analog waveform.

In the exemplary embodiment of the invention, digital samples of the data to be monitored are stored in a circular buffer implemented in the memory of the microcontroller 414 or in the memory card 110 itself. The number of bytes in the buffer may be fixed at, for example; 1024 and byte address may be generated using a modulo 1024 counter. Thus, new data is continually overwriting old data. In this configuration, each circular buffer holds samples representing a fixed time interval. If, for example, the buffer is limited to 1024 bytes and one-byte samples are added to the buffer at a rate of 16 per second, the stored samples represent a period of approximately one minute.

Three items of information are maintained in the fixed data portion of each circular buffer: the type of data in the buffer, the starting address of the buffer and the address of the oldest sample in the buffer. The exact format of these data items depends on the number of different types of data that may be recorded and the size of the circular buffers.

In addition to the circuitry shown in FIG. 4, it is contemplated that the patient station microcomputer 414 may be coupled to a keyboard (not shown) and to a video display monitor (not shown) so that data on the patient may be viewed from and entered into both the central computer system 432 and the memory card 110 from the patient's bedside.

Figure 14:
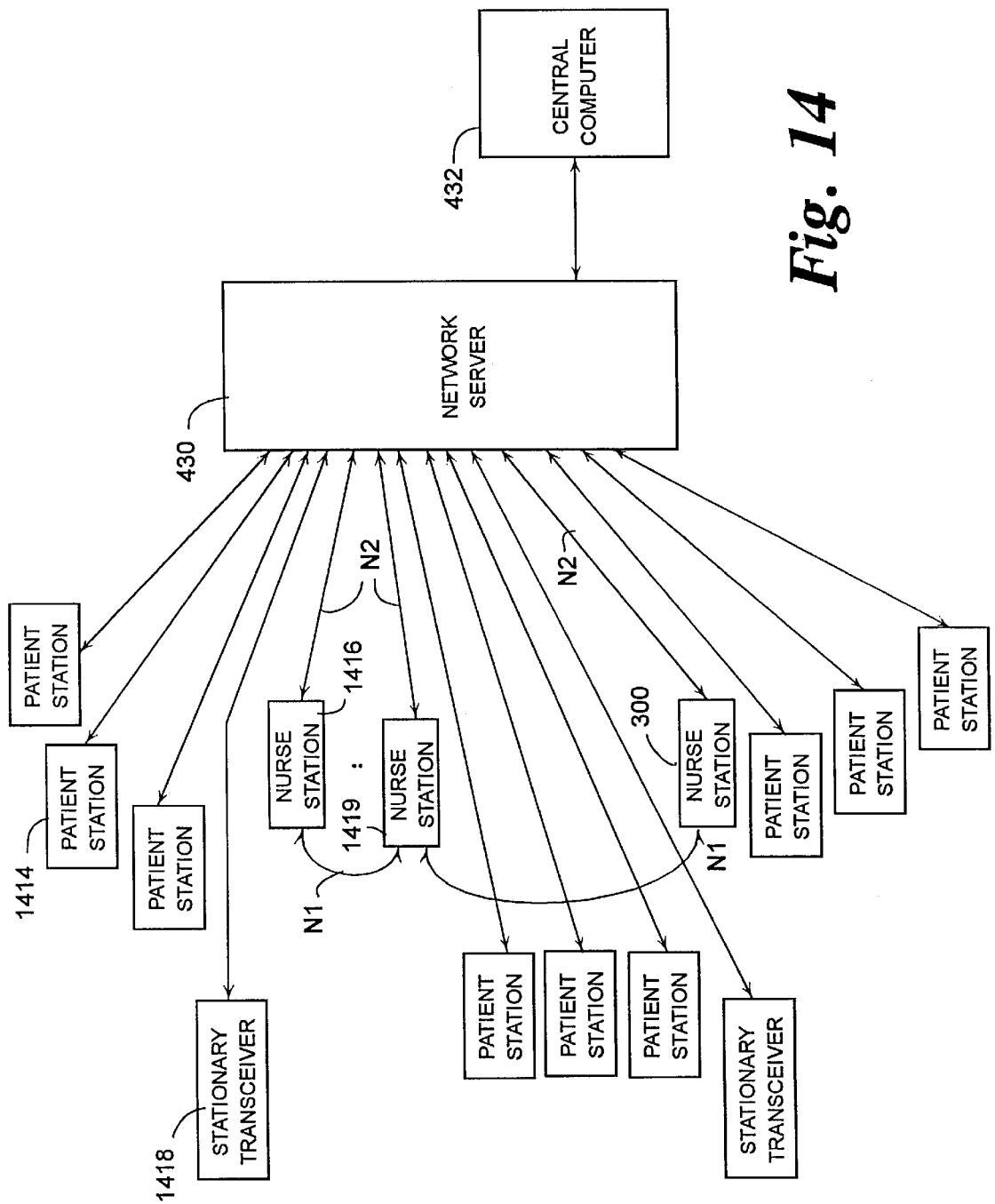
FIG. 14 is a block diagram showing an exemplary data and voice communication network suitable for use with the present invention.

The patient station microcomputer 414 is coupled to the central nurse station microcomputer 420 via a network server 430. The nurse and patient stations may be connected in a star configuration, as shown in FIG. 4, and/or in a ring configuration as shown in FIG. 14, described below. Alternatively, the patient station and the central nurse station 300 may be coupled through the telephone set in the patient's room. For this type of coupling, the network interface ports in each of the microcomputers 414 and 420 are configured to time-division multiplex data with voice communication when the telephone is in use. Multiple patient stations (not shown) may be coupled to the microcomputer 420 of the nurse station 300 via the network interconnection.

The network server 430 used to couple the patient station 210 to the central nurse station 300 may be a complex commercially available network interface such as that produced by Novell, Inc.

Portable nurse unit 2310, as shown in FIG. 23 and FIG. 4 is capable of transmitting data to a transceiver 424. There are actually a plurality of transceivers 424 throughout a hospital. In the exemplary embodiment of the invention, these are infrared transceivers capable of both transmitting and receiving infrared signals. Such infrared transceivers are desirably located in every open area of the hospital is because a partition or wall can easily block an infrared signal. In general, one transceiver per room may be sufficient; however, if a room is partitioned, then it may be desirable to place one transceiver 424 in each open area of the room to easily receive the infrared transmission from external devices or nurse notepad terminals.

Transceiver 424 is in electrical communication with server 430, as shown in FIG. 4. All of servers 430 are connected, for example, in a star configuration and linked to central computing system 432.

Similarly, patient station microcomputer 414 and nurse station microcomputer 420 are linked to server 430. The patient station microcomputer 414 could either be linked by a cable or could be linked via infrared transceivers 452 and 456 in the same way that portable nurse unit 2310 is linked via transceivers 425 and 424.

The IR transceivers 424 also provide network connections for stand-alone external devices which may be used to send data on patient vital signs to the computer network and for the staff badge transmitters 1111, described above.

Figure 5:
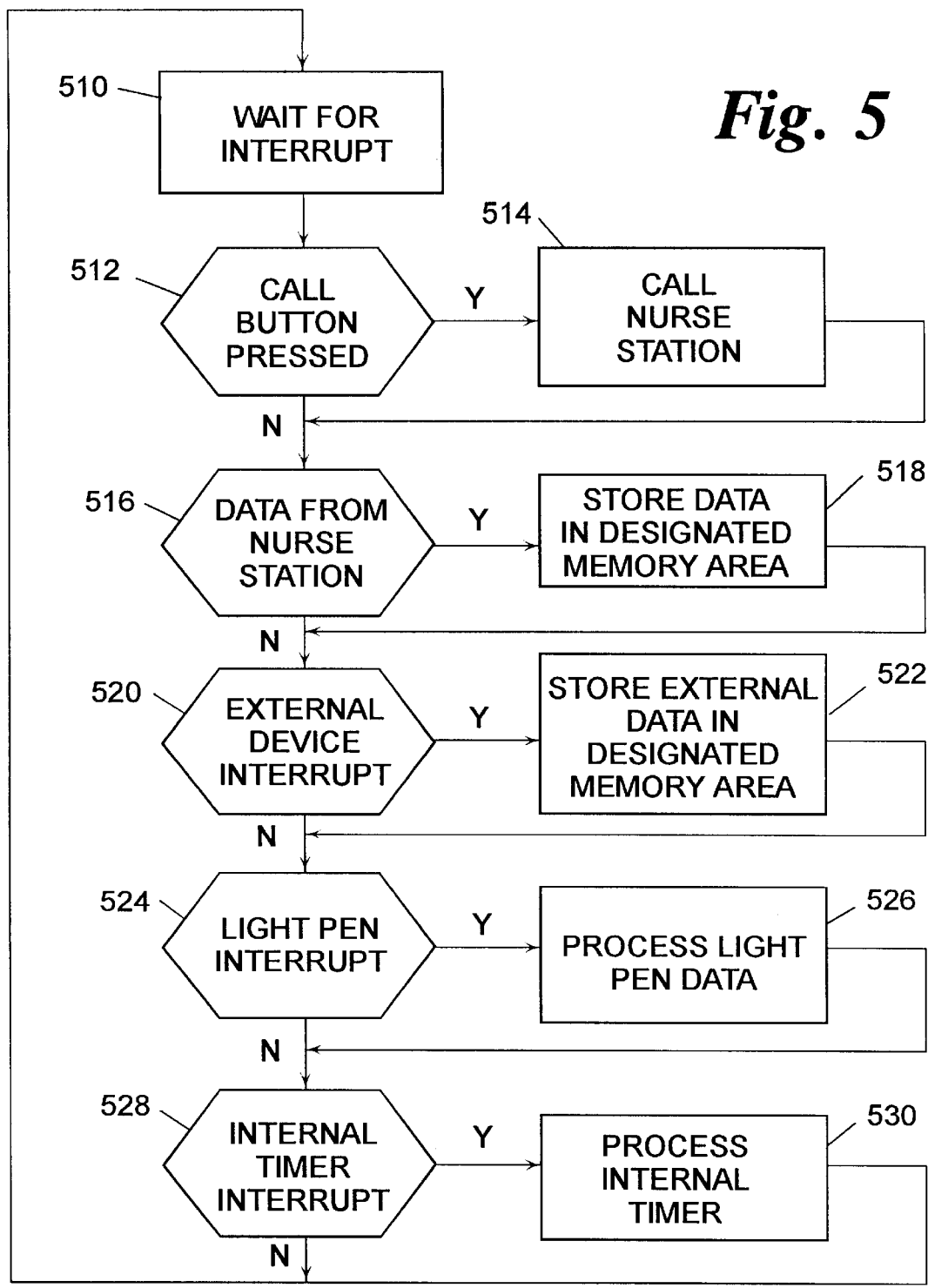

FIG. 5 is a flow-chart diagram which illustrates the main loop of the program that controls the patient station 210. At step 510, the microcomputer 414 in the patient station 210 is in an idle state waiting for an interrupt. In this state, the microcomputer 414 may be used for other purposes, such as to provide the patient with information or entertainment. Alternatively, the,microcomputer 414 may be programmed with diagnostic aids for use by the caregivers in monitoring the patient's condition.

When an interrupt occurs, the computer 414 enters an interrupt routine which checks for the occurrence of each possible type of interrupt, processes the interrupts which have been provided to the routine and returns the microcomputer 414 to its idle state.

At step 512, the interrupt routine determines if the interrupt was generated by the patient squeezing the bulb 212 or by pressing the nurse call button. If so, the step 514 is executed which performs the call nurse station function and control is transferred to step 516. The steps which implement the call nurse station function are described below with reference to FIG. 6.

After the nurse call interrupt is processed at step 514 or if the interrupt was not a nurse call at step 512, the interrupt routine, at step 516, determines if the interrupt was caused by data being provided to the microcomputer 414 from the central nurse station 300. If so, step 516 invokes step 518 to store the data provided from the nurse station 300 into the local memory of the patient station or, if appropriate, into the memory card 110 itself. Step 518 and then transfers control to step 520. The steps which implement the step 518 are described below in reference to FIG. 7.

If, at step 516, it is determined that the interrupt was not caused by the receipt of data from the nurse station 300, control is transferred to step 520. Step 520 determines if the interrupt was generated by an external device, coupled to the external device input port 220 (shown in FIG. 2). As set forth above, one or more external devices may be coupled to the patient station 210 to store a vital sign data in its local memory or on the memory card 110. The interrupt detected at step 520 would occur when one of these external devices is ready to provide a sample to the patient station 210.

If step 520 determines that the interrupt is from an external device, step 522 is executed to store the external data onto the card and then control is passed to step 524. The process represented by step 522 is described below with reference to FIG. 8.

If, at step 520, it is determined that the interrupt was not generated by an external device, control is transferred to step 524. Step 524 is executed to determine if the interrupt was generated by the light pen 222. As set forth above, the light pen 222 is provided to read bar-coded information from patient wrist bands, containers of prescription medicine, food trays, diagnostic images and other material that is desirably associated with a particular patient. The light pen 222 may be operated, for example, by pressing a button on the pen while the pen is dragged across the bar code and then releasing the button. The light pen interrupt would be generated when the button is released. If a light pen interrupt is detected at step 524, the interrupt routine invokes step 526 to process the light pen interrupt and then transfers control to step 528. The steps performed in carrying out step 526 are described below with reference to FIG. 9.

If, at step 524, it is determined that the interrupt was not generated by the light pen 222, control is transferred to step 528. Step 528 determines if the interrupt was caused by the internal timer of the microcomputer 414. If so, step 528 invokes a step 530 to process the internal timer interrupt. This step acts as an alarm clock to ensure that medication is administered on time and to ensure that any data which needs to be monitored at timed intervals is handled properly. When the internal timer has been processed, step 530 transfers control to step 510 to wait for the next interrupt. Control is also transferred to step 510 from step 528 if it is determined that no internal timer interrupt needs to be serviced.

In this description of the exemplary embodiments of the invention, reference is made to storing data into the card. If either of the memory cards 110 and 110' has limited or external memory or has internal memory which can undergo only a limited number of storage operations, it may be desirable to assign a buffer area in any of the microcomputers or microcontrollers coupled to the data card which acts as the card memory while the card is coupled to the device. In this instance a write operation to memory locations on the card would only be made when the card is removed from the device. At this time, the contents of the buffer may be transferred to the memory card as a block or separate write operations may be performed for those locations that have been changed while the card has been attached to the device.

Figure 6:
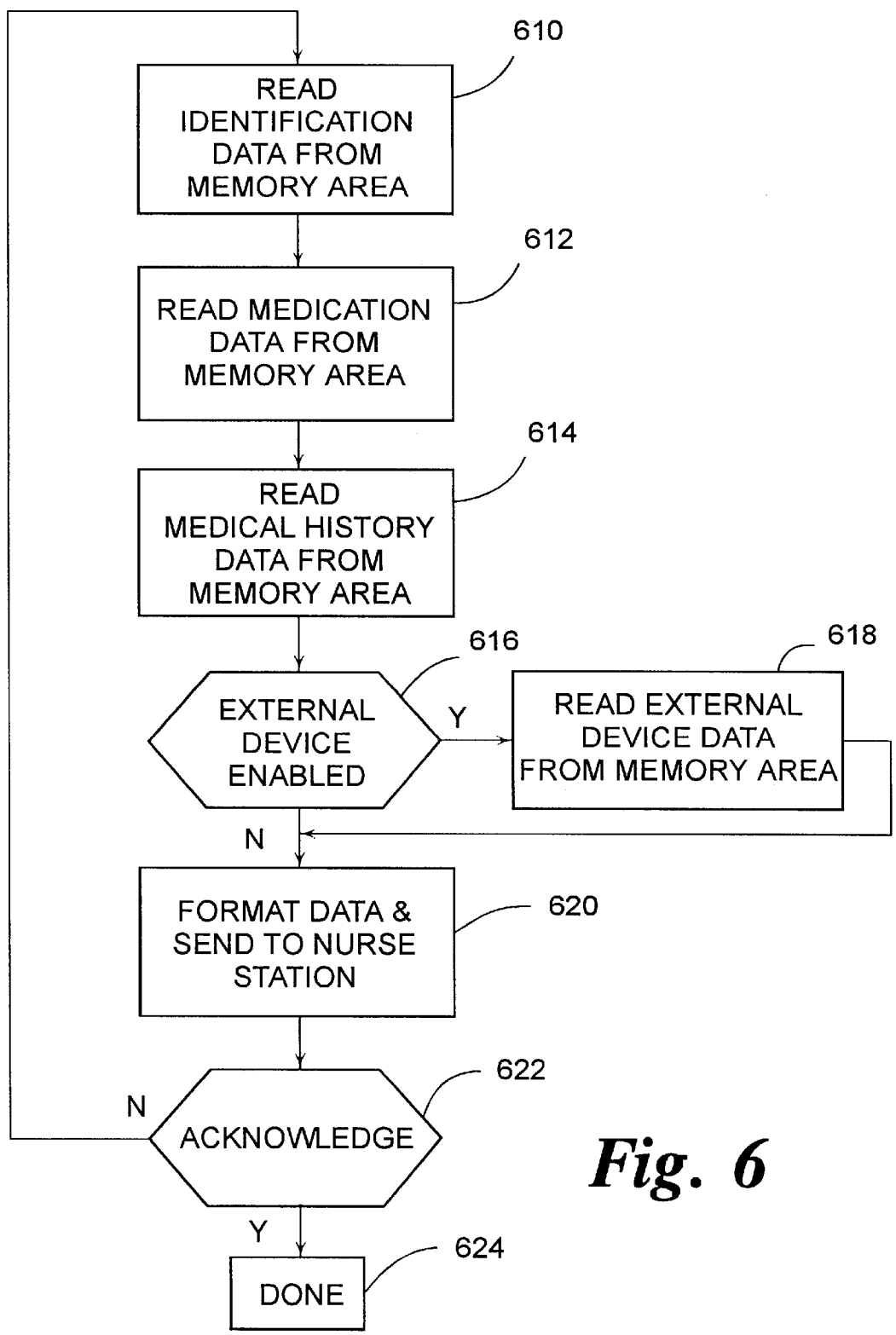

FIG. 6 is a flow-chart diagram showing details of the processing steps performed by the processor 414 in response to a nurse call interrupt. Steps 610, 612 and 614 read fixed data from the patient station 210 as shown in FIG. 2. This data is stored in the local memory of the computer 414. At step 616, the microcomputer 414 determines if an external device is coupled to the external device input port 220, if the patient station 210 has been enabled to receive data from the device and if the device has written any data to the patient station memory. If all of these conditions are met, step 616 transfers control to step 618. The microcomputer 414, at step 618, determines the location of the data to be read and the address of the oldest sample.

After step 618, or if one of the conditions fails at step 616, control is transferred to step 620. This step formats the data that is to be transferred to the nurse station 300 and transmits it to the nurse station via the network server 430.

At step 622, the microcomputer 414 waits for an acknowledge (ACK) response from the microcomputer 420. If a negative acknowledge (NAK) is received or if there is no response after a predetermined time-out period, the computer 414 transfers control back to step 610 and the process of extracting, formatting and transmitting the data is repeated. If the ACK is received at step 622, the call nurse station process terminates at step 624. The nurse call message remains active at the nurse station 300 until it is cleared by pressing the CLEAR button 218 of the patient station 210, as shown in FIG. 2.

Figure 7:
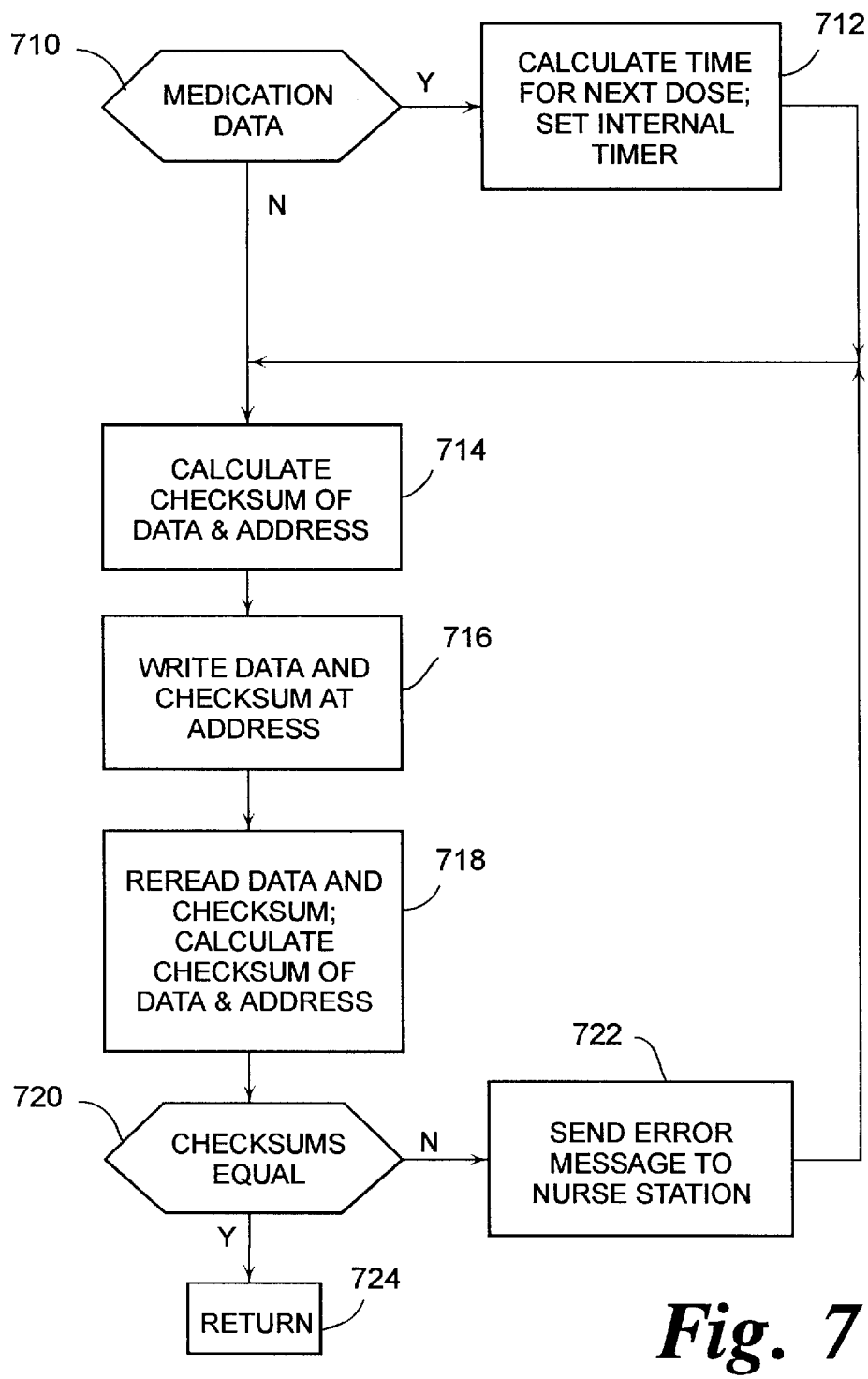

FIG. 7 illustrates the program flow of the process which stores data onto the memory card or into the memory card buffer area of the microcomputer 414. This process is step 518 of FIG. 5. The first step in the process, step 710, determines if the data being entered is medication data. If so, at step 712, the process calculates the time for the next dose and sets the interval timer.

After step 712 or if the data is not medication data at step 710, the process executes step 714, which calculates a checksum of the data and the address at which the data is to be stored. At step 716, the data and the checksum are then supplied to the memory card buffer area or to the memory card reader/writer 412. The data is provided with the starting address on the card of the first storage location to be used to hold the data. Step 716 also conditions the reader/writer 412 to write the data onto the card.

At step 718, the microcomputer 414 conditions to read the data that was just written to the card or to the card buffer area and calculates a checksum for the data and address value. Step 720 compares the checksum calculated for the original data to the checksum calculated for the retrieved data. If the checksums are not equal, the microcomputer, at step 722, sends an error message to the nurse station microcomputer 420 and transfers control to step 714 to retry the data storage operation. If, at step 720, the checksums are found to be equal, the data storage process terminates at step 724.

Figure 8:
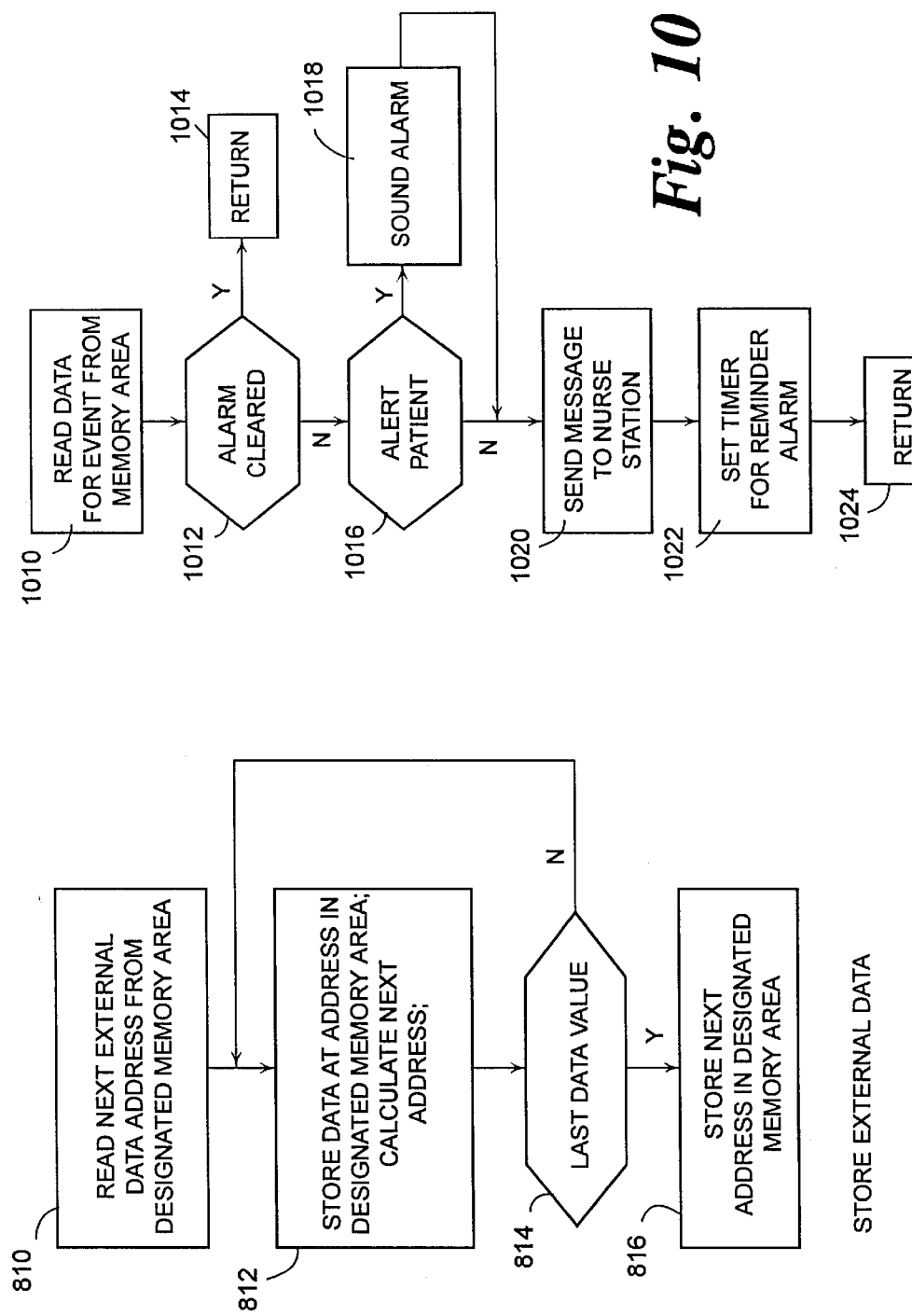

FIG. 8 is a flow-chart diagram of the process 522 of FIG. 5, which stores data from external devices into the local memory of the patient station microcomputer 414. The first step in the process, 810, reads the next data address into which data is to be written from the card buffer area in the microcomputer 414. This address is the same as the address of the oldest data item. Step 812, stores one byte of data into this address and calculates the next address. As set forth above, the address calculation uses the length of the buffer as a modulus so that the buffer appears to be a circular buffer. For example, if a buffer length of 1024 is selected and the base address of the data in the local memory of the microcomputer 414 is at BASEADR, the address calculation to obtain the next address, NXADR from the current address, CURADR may be calculated using the equation (1).

$$NXADR=BASEADR+(CURADR-BASEADR+1) modulo 1024 \quad (1)$$

At step 814, the microcomputer 414 determines if the data item just stored was the last data item to be processed. If so, step 816 is executed in which the microcomputer 414 stores the calculated next address value in the memory card buffer area as the address of the oldest data item. Step 816 then ends the external data storage process. Otherwise, step 814 transfers control to step 812 to write the next data item onto the designated card buffer area.

In the same way that external data is stored from patient station microcomputer 414, data can be stored from portable nurse unit 2310. Such data could be entered from an external device with a transceiver 411. This information is communicated to the portable nurse unit then sent by transceivers 425 and 424 to server 430. The information could either be stored at server 430 or server 430 could be configured to send a signal back through transceivers 424 and 425 to the portable nurse unit 2310 instructing the nurse unit to impart the information onto the memory card which is loaded onto the portable nurse unit.

Figure 9:
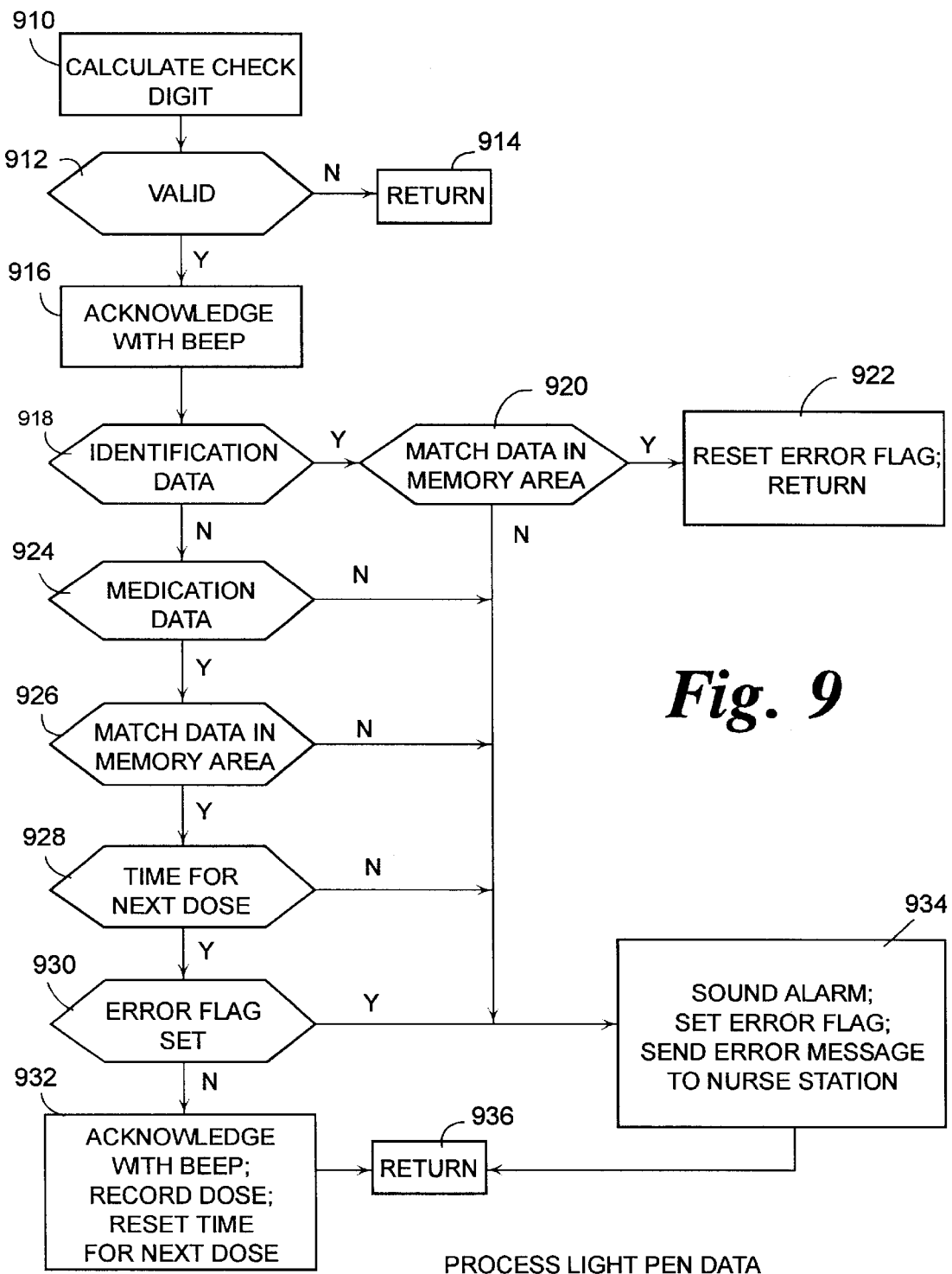

FIG. 9 illustrates the steps performed by the microcomputer 414 in processing data from the light pen 222 of FIG. 2. In the exemplary embodiment of the invention, the light pen data is provided to the microcomputer 414 via the light pen interface 416, shown in FIG. 4. This interface translates the alternating light and dark patterns sensed by the light pen 222 into a sequence of digits. Conventional bar-coded data includes a check digit, such as a cyclic redundancy code (CRC) digit, as the last digit of the data. This digit may be calculated by applying a predetermined formula to the other bar-coded digits.

In the exemplary embodiment of the invention, bar-codes are used to ensure that medications, radiographic images, food trays and other material are provided to the proper patient. As an example of how the bar-codes may be used for this function, consider the administration of prescribed medication. Before giving the medication to the patient, the nurse first scans the patient arm band. The patient station compares the scanned data to the identification data retrieved from the card. If these two codes do not match then either the patient is in the wrong bed or the wrong memory card is inserted in the patient station 210.

If the codes do match, the nurse then scans the bar-code on the medication container. The patient station 210 compares the scanned data to medication data in the memory card buffer area. If a match is found, the station 210 determines when the next dose of the medicine is to be administered. If the next dose is past due or if it is due in the near future, the patient station 210 records a the time at which the medication was given. If the medication is not found in the card buffer area or if it is not yet due, the station 210 sounds an alarm, for example a distinctive series of pulse tones, and sends an appropriate error message to the nurse station 300. If, as set forth above, the patient station 210 is equipped with a display device, the error message may also be displayed on the patient station display.

For radiographic images, food trays and other material that is simply to be delivered to the patient's bed, a bar-code identifying the patient is scanned from the image, tray or other material. The scanned data is then compared to the identifying data on the card. If the data is correct, the scan is acknowledged with a beep. Otherwise the alarm is sounded and an error message is sent to the nurse station 300 indicating that material has been delivered to the wrong patient.

The first step in FIG. 9, step 910, calculates the check digit using all but the last digit of the code supplied by the light pen interface 416. Step 912 then compares the calculated check digit to the last digit of the scanned code. If the digits do not match, step 914 is executed which returns control to the main loop program shown in FIG. 5.

If, however, the check digit is found to be valid at step 912, step 916 is executed which acknowledges the receipt of the code by conditioning the patient station 210 to emit a beep from its speaker 214. At step 918, the microcomputer 414 determines if the code provided by the light pen interface 416 is identification data. If so, step 920 is executed to determine if the supplied code matches the code stored on the card buffer area. As set forth above, this code was entered into the buffer area from the card. The data on the card was entered by scanning the patient's arm band during admission processing. If the scanned identification code matches the stored code at step 920, step 922 is executed which resets the error flag and returns control to the main program loop.

Otherwise, step 934 is executed. This step sounds an alarm through the speaker 214 of the patient station 210, sets the error flag and sends an error message to the central nurse station 300 indicating that the scanned identification data does not match the stored data.

If, at step 918, the scanned data is not identification data, step 924 is executed. Step 924 determines if the scanned data is medication data. If so, 926 is executed, otherwise, an error has occurred and control is transferred to step 934. This step operates in the same manner as set forth above, except that the error message indicates that the scanned data was neither identification data nor medication data.

Step 926 determines if the scanned medication matches any of the medication data stored in the memory card buffer area. If a match is found, step 928 is executed, otherwise an error has occurred and step 934 is executed with an error message indicating that the medication has not been prescribed for the patient.

In step 928, the microcomputer 414 compares the current time, as derived from its internal time of day clock, to the stored time for the next dose of the medication. This time value is stored in the card buffer area as a part of a multi-value record for the medication information. Each prescribed medication is entered in the buffer area as a separate medication record. If the next-dose time has passed or if it is in the near future, for example, 15 minutes from the present, step 930 is executed. Otherwise, an error has occurred and step 934 is executed with an error message indicating that the medication is being provided at the wrong time.

Step 930 checks the error flag. This flag is set in step 934 if any error occurs and is reset in step 922 when the scanned identification data is found to match the patient. The test in 930 ensures that erroneous identification data is not ignored. If the error flag is set at step 930, then an error that occurred during a previous attempt to administer medication has not been cleared. In this instance, step 934 is executed with an error message indicating that a previous error has not been cleared.

If, at step 930, the error flag is reset, step 932 is executed. This step conditions the patient station 210 to emit an acknowledging beep, disables any internal timer interrupt that may be set for this medication dose, records the current time in the medication record to indicate that the medication has been administered and calculates the time for the next dose. The next-dose time is also stored in the medication record on the memory card buffer area of the microcomputer 414 and an internal timer interrupt is set for this next dose time. After step 932 and after step 934, the process which reads the light pen data is complete and control is returned to the main loop program at step 936.

In the same way as shown in FIG. 9, portable reader 2310, as shown in FIG. 23 and at FIG. 4, can be used in place of the combination of light pen and patient station microcomputer to determine when the next dose of a prescription drug is due. Portable reader 2310 has a slot, 2314, for accepting and scanning and reading the information from a patient memory card. It also can read a bar code on a patient's wrist or a medication bottle using a light pen 2328. Portable reader 2310 also is capable of transmitting input of this information to a fixed transceiver such as transceiver 424 as shown in FIG. 4. This information is then sent to server 430 via transceiver 425. The portable reader 2310 operates in the same manner as the patient station as illustrated by FIG. 9.

FIG. 10 illustrates the program flow of step 530 of FIG. 5, which processes the internal timer interrupts from the microcomputer 414 of the patient station. In the exemplary embodiment of the invention, the timed event, for example, the next-dose time in a medication record, is stored in the card buffer area at a known location. Step 1010 reads the event data from the buffer area, using the address that was stored with the timer interrupt request. Step 1012 compares the stored time to the current time and checks an alarm cleared flag to determine if the alarm is no longer necessary. If step 1012 determines that the alarm has been cleared, control is returned, at step 1014, to the main program loop of FIG. 5.

If the alarm has not been cleared at step 1012, step 1016 is executed to determine if the patient is to be alerted or if only the nurse station 300 is to be alerted. If the patient is to be alerted, step 1018 is executed which conditions the patient station 210 to emit an audible alarm through the speaker 214. Whether or not the patient is to be alerted, step 1020 is executed to send an alarm message to the nurse station 300. In the exemplary embodiment of the invention, the text of the alarm message is determined from a code stored with the timer interrupt data on the memory card 110. This code is used to index a table of alarm messages stored in read-only memory (ROM) (not shown) in the patient station microcomputer 414.

After step 1020, the microcomputer 414 executes step 1022 to set a reminder alarm for a predetermined time, for example, five minutes after the initial alarm. This reminder alarm is handled in the same manner as any other internal timer interrupt. Any outstanding reminder alarms may be cleared by pressing the CLEAR button 218 on the patient station 210.

The discussion above has centered on the use of the invention for patients in a hospital. Since a hospital patient spends a large percentage of time in his bed, the interface between the personal database and the hospital computer system can be a fixture in the patient's room. For reasons set forth below, it is desirable to extend the use of the invention to caregivers at the hospital. Caregivers, however, are more mobile and would not be adequately served by an immobile interface.

Figure 12:
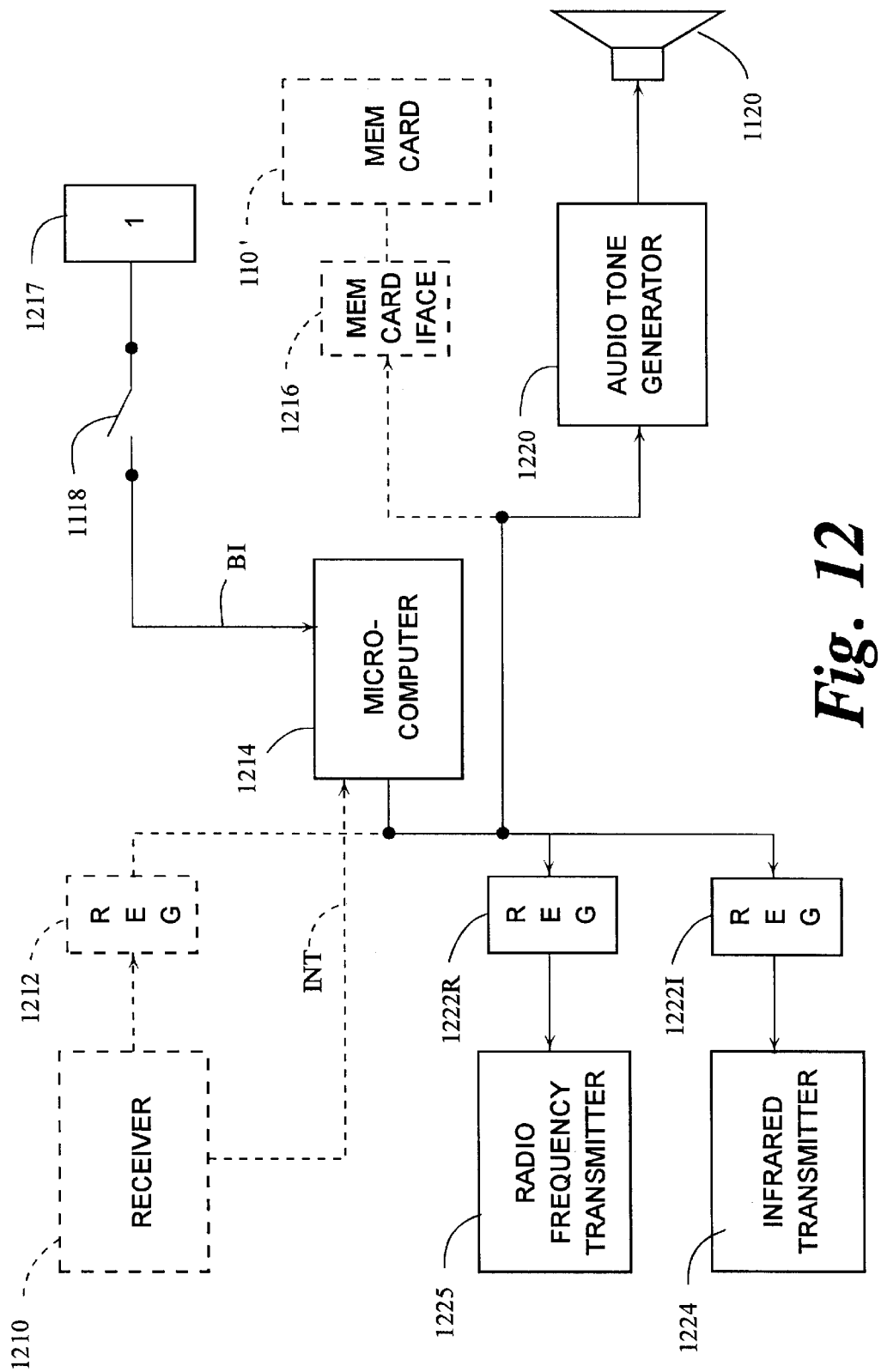
FIG. 12 is a block diagram showing the functional connectivity of the portable transceiver shown in FIGS. 11a and 11b.

FIG. 12 is a block diagram that illustrates the functional structure of the electronic circuitry in the base 1112 of the badge-holder database interface. For the sake of simplicity, the power supply has been omitted from FIG. 12. In the exemplary embodiment, power is provided by a standard replaceable lithium battery (not shown). The microcomputer 1214 may be any one of a number of commercially available microcontrollers, such as the 80C49 manufactured by Intel Corporation, coupled to ROM program storage (not shown) and RAM data storage (not shown).

The badge transmitter includes an infrared transmitter 1224, a radio frequency transmitter 1225 and an audio tone generator 1220. Badges which are able to both send and receive data and to store data into a programmable memory card also include an infrared receiver 1210 and a memory card interface 1216.

In a badge transceiver of this type, the functions performed by the microcomputer 1214 may include providing an address to a memory card interface 1216 to store data into or read data from the memory card 110, conditioning an audio tone generator 1220 to produce an audio signal from the speaker 1120, or storing a value into one of the registers 1222I and 1222R and then conditioning the appropriate transmitter 1224 or 1225 to broadcast the data value to the network of fixed infrared and RF transceivers.

Alternatively, when the badge transmitter is a simple transponder which emits an identification code at predetermined intervals as programmed by the base unit, the microcomputer 1214 may be eliminated and replaced by a programmable timer and/or simple logic circuitry to perform the limited functions of the transponding badge.

Also included in the badge circuitry is the push-button switch 1118, through which a source of logic-one value, 1217, may be momentarily coupled to an interrupt line, BI, of the microcomputer 1214. In response to this interrupt, the microcomputer 1214 sends identifying information, read from the memory card 110' and either an emergency alert message or an acknowledge message using both the infrared transmitter 1224 and the radio frequency transmitter 1225. The operation of the circuitry shown in FIG. 12 in the hospital environment is described below with reference to FIGS. 13–16.

In the exemplary embodiment, the badge holder includes two transmitters, an infrared transmitter 1224 which is used primarily to send identification data and a radio-frequency device, operating at frequencies of approximately 300 MHz. Radio frequency transmitters suitable for use in the badge holder are available from Dallas Semiconductor Inc. It is contemplated that other transmitter components may be used, for example, the infrared transmitter of the PLS-4000 personnel locating system available from TELOC, Inc.

FIG. 13 is a flow-chart diagram which illustrates the operation of the badge transmitter shown in FIGS. 11 and 12. The badge transmitter is activated by an interrupt at step 1310. The interrupt may be from the push-button switch 1118 or from an internal timer (not shown) which is set by the base unit 2210, shown in FIG. 22, to periodically transmit the identification information. If, at step 1312, it is determined that the interrupt was generated by the switch 1118, the microcomputer 1214, at step 1314, conditions the audio generator 1220 to provide a pulse tone signal to the speaker 1120. This tone serves as audio feedback letting the wearer know that the badge circuitry has sensed the closing of the switch 1118.

When the button 1118 is pushed, the wearer is assumed to be signalling an emergency alert. In this instance step 1320 is executed which conditions the microcomputer 1214 to send an emergency alert message to the transmit registers 1222I and 1222R and to transmit the message through both the IR transmitter 1224 and the RF transmitter 1225. In order to reduce the number of accidental emergency alert messages, it may be desirable to program the microcomputer 1214 to require that the switch 1118 be pressed in a pattern, for example, three times within a 10 second interval to signal an emergency alert. After the message is transmitted in step 1320, control is transferred to step 1310 to await the next interrupt. If the host computer is waiting for an acknowledgement from the badge wearer, this message is interpreted as an acknowledgement. Alternatively it may be desirable to have another code, for example, pressing the switch once or twice to indicate an acknowledgement.

If, at step 1312, the interrupt is a timer interrupt, a signal which includes a synchronization component and an identification component is transmitted in a discrete time interval, for example 45 microseconds, at a preset time interval having a maximum length of, for example 3 seconds. As set forth above, this time interval is assigned by the base unit 2210 when the badge holder 1111 is programmed.

At step 1346, the identification data and a check sum are generated by the microcomputer 1214 and, at step 1349, are loaded into the IR transmission register 1222I. Also at step 1349, the IR transmitter 1224 is activated to transmit the data. At step 1350, the badge transmitter returns to an idle state to await the next interrupt.

The timer, which is programmed by the base unit 2210, repeatedly interrupts the badge unit at a fixed time interval which is different for each badge unit. Since an individual transmission occupies only 45 microseconds out of a: three-second interval, as many as 65,536 ($2^{16}$) such intervals may be defined. This continual transmission of relatively short identification signals permits a relatively large number of entities within one communication network while keeping the likelihood of conflicts caused by overlapping message transmissions low.

As set forth above, the badge transmitter is used, in this embodiment of the invention may be used as a data link between the personal database implemented in the memory card 110' and the central computer system. The portable nurse station 2310 and external devices, such as device 428 of FIG. 4 may also be coupled to the central computer via a wireless data link. The other part of this data link is the network of stationary transmitters located at fixed positions around the hospital. FIG. 14 is a block diagram showing the data link between the network of stationary transceivers, the nurse stations, the patient stations and the central computer system 432.

As shown in FIG. 14, the stationary transceivers 1402 and 1404; the nurse stations 1406, 1408 and 1410; and the patient stations 1412 through 1428 are all coupled to the network server 430 via a star-type network N2. In addition, the nurse stations 1406, 1408 and 1410 are coupled together by a ring network N1. In the event of a failure of the central computer 432 or network server 430, data communications among the central nurse stations would occur through the network N1.

In the exemplary embodiment of the invention, each of the stationary transceivers 1402 and 1404 is responsive to commands from the central computer 432, transmitted via the network server 430, to receive identification data from (and optionally transmit data to) the various badge transceivers, to receive telemetry data from external devices such as the device 428 of FIG. 4 and to receive data from and transmit data to the portable nurse stations such as the station 2310 of FIG. 4. Each stationary transceiver includes circuitry which automatically performs all of the steps needed to ensure that the command from the main computer is carried out and that the data was delivered without corruption.

Figure 15:
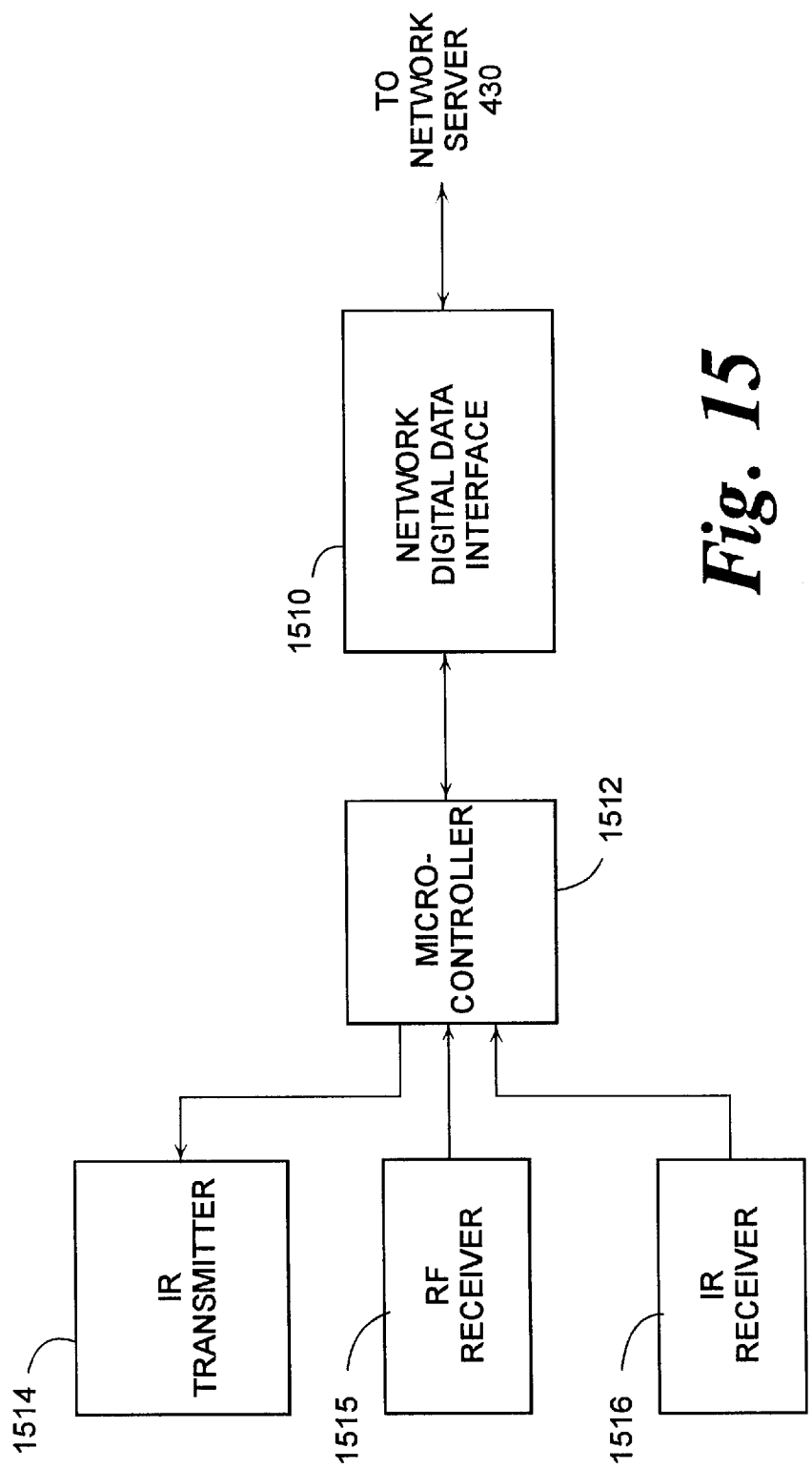
FIG. 15 is a block diagram showing details of the transmitter-receiver units shown in FIG. 14.

FIG. 15 is a block diagram showing the functional structure of a stationary transceiver. In addition to an infrared transmitter 1514, an infrared receiver 1516 and an RF receiver 1515, the transceiver includes a microcontroller 1512 and a digital data interface 1510 through which the transceiver is coupled to the server 430. The network digital data interface 1510 provides a digital data connection to the server 430. The type of unit used depends on the network connectivity available to the server.

The stationary transceiver shown in FIG. 15 includes a microcontroller 1512. This unit includes a simple microprocessor (not shown), a ROM program store (not shown) and a small RAM (not shown) for holding data and temporary results. The microcontroller 1512 is programmed to implement a low-level portion of a hierarchical token bus protocol.

Figure 16A:
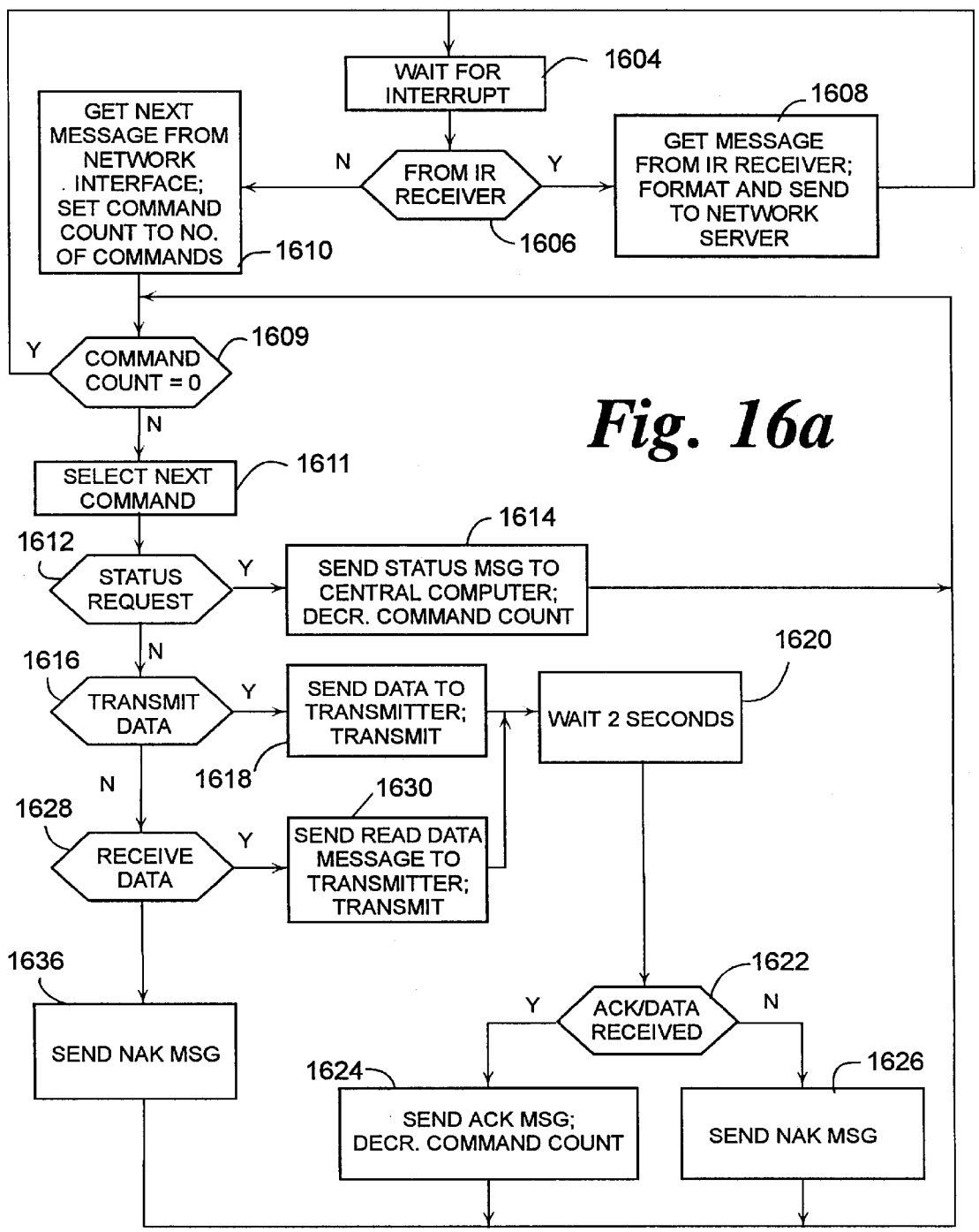

FIG. 16a is a flow-chart diagram which illustrates the process steps performed by the program that controls the microcontroller 1512. As set forth above, the stationary transceivers 1418, 1422 and 1428 are programmed to carry out commands provided by the central computer system. These commands include: a status request command for which the stationary transceiver sends an indication of its status to the main computer, a transmit data command for which the stationary transceiver transmits data provided with the command, and a receive data command for which the stationary transceiver expects to receive data from a portable nurse station, external monitoring device or, optionally, a badge transceiver. Multiple commands may be issued at a single time.

At step 1604 of the stationary transceiver process, as shown in FIG. 16a, the transceiver waits for an interrupt. When an interrupt occurs, it may be from the infrared or RF receiver or it may be from the central computer 432 via the network server 430. Interrupts from the infrared or RF receivers may occur at any time. As set forth above, these interrupts may signal the receipt of an identification message sent by a transponder badge or an emergency alter message caused by pressing the emergency alert button on the badge. If, at step 1606, the message is from the IR or RF receiver, step 1608 is executed to format the message and send it to the network server 430. After step 1608, control is returned to step 1604 to await the next interrupt.

Alternatively, if, at step 1606, a message from the network interface is detected, step 1610 is executed. At step 1610, the command message is received from the central computer 432 via the data communications network N2 and the network interface 1510 and the number of commands in the message is stored in a memory location COMMAND COUNT. This memory location serves as a pointer to the commands in the message.

Step 1609 determines if any commands in the message have not been executed. If unexecuted commands exist, then at step 1611, the next command is selected from the message. At step 1612, the microcontroller 1512 determines if this command is a status request command. If so, step 1614 is executed. This step sends a status message to the central computer 432 and decrements COMMAND COUNT so that it points to the next command. The status message may include, for example, information identifying the stationary transceiver and its location, and the numbers of ACK and NAK messages both sent and received by the stationary transceiver. The relative numbers of ACK and NAK messages provide an indication of the condition of the stationary transceiver. After step 1614 control is transferred to step 1609 to extract the next command from the received message.

If, at step 1614, the selected command is not a status request, then step 1616 is executed. This step determines if the command is a transmit data command. If so, at step 1618, the data to be transmitted is sent to the infrared transmitter 1514 and the transmitter is conditioned to broadcast the data. At step 1620, the microcontroller 1512 waits two seconds for an ACK message from the receiving transceiver (e.g. The transceiver of a portable nurse station 2310 or external device 428, shown in FIG. 4) indicating that the message has been received.

If, at step 1622, an ACK is received during the two second interval, the microcontroller 1512, at step, 1624, sends an ACK message to the central computer 432, decrements the COMMAND COUNT to point to the next command and transfers control to step 1609 to retrieve the next command from the message. Otherwise, at step 1626, the microcontroller 1512 sends a NAK message to the central computer and branches to step 1609 to retry the current command. In this embodiment of the invention, the central computer 432 is programmed to allow a fixed number of retries (consecutive NAK messages) and then to retransmit the command message to the stationary transceiver.

At step 1616, if the selected command is not a transmit data command, step 1628 is executed to determine if it is a receive data command. If so, the microcontroller 1512 sends a read data message to the transmitter 1514 and conditions the transmitter to broadcast the message. Step 1630 then transfers control to step 1620, described above.

Steps 1620, 1622, 1624 and 1626 operate in the same manner for the receive data message as for the transmit data message except that step 1624 sends the data to the central computer 432 via the network server 430 and an ACK message to the other transceivers, while step 1626 sends NAK messages to both the other transceivers and the central computer 432. The microcontroller 1512 does not check for parity errors or checksum errors in the received data. These checks are performed at the central computer when it receives the data.

If, at step 1628, the command is not a receive data command, then it is an unknown command. In this instance, the microcontroller 1512 sends a NAK message to the central computer 432, decrements the command count and then branches to step 1609 to get the next command.

The process illustrated in FIG. 16a runs on the microcontroller 1512 in a continuous loop. This process is continually interrupted by a signal received from one of the badge transmitters which continually transmit their identification signals. Emergency alert messages or response messages generated by pressing the button 1118 on the badge transmitter 1111, shown in FIG. 11, occur only occasionally and should not be able to be confused with any other data messages. Thus, the microcontroller 1512 includes an unmaskable interrupt which is caused when the RF receiver receives a message. In this instance, at step 1650 of FIG. 16b, the interrupt is sensed and in response to this interrupt, at step 1656, the identification information from the badge and the location of the fixed transceiver which received the information are sent to the central computer 432.

Figure 17B:
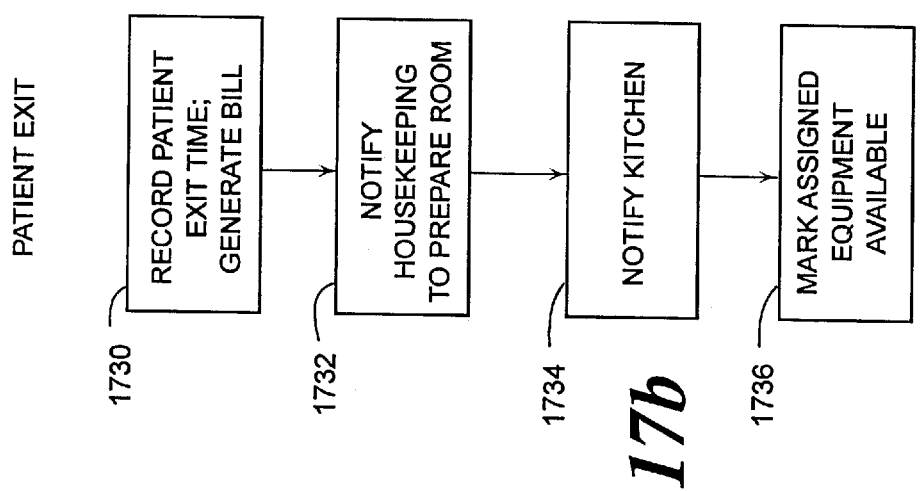
FIGS. 17a and 17b are flow-chart diagrams which illustrate the handling of patient entry and patient exit using a hospital monitoring system that includes an embodiment of the present invention.
Figure 17A:
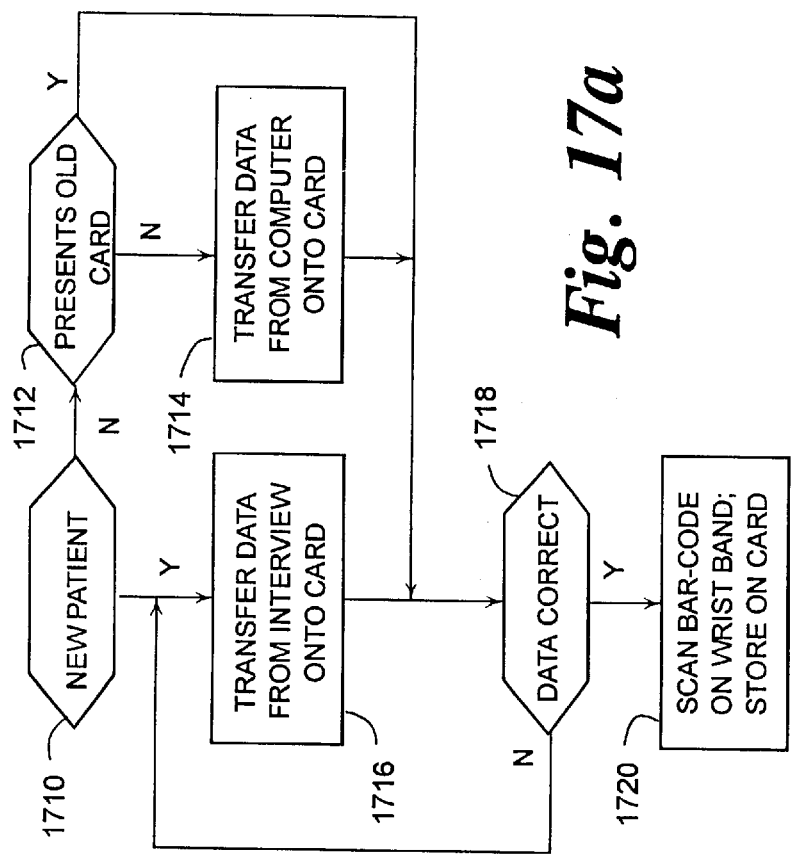

The discussion of FIGS. 1–16b above has described various components of a distributed processing network in which information on individuals and important equipment is stored on a personal database that is kept in close proximity to the individual or equipment. FIGS. 17a through 17d illustrate four exemplary functions that may be performed using this network. FIGS. 17a and 17b describe steps performed when the patient enters and leaves the hospital, FIG. 17c describes a process for locating equipment and personnel, and FIG. 17d describes a process for automating the assembly of teams of specialists to handle an emergency situation such as a "code blue."

At step 1710 of FIG. 17a, when a patient enters the hospital he may already have been issued a memory card 110. If so, at step 1712, he may have the card in his possession, in which case he presents it, or he may not have the card. If he does not have the card, step 1714 is executed which transfers an image of the card data as of the time the patient left the hospital, onto a new card. This stored data may be maintained in auxiliary data storage, such as a cartridge tape, coupled to the central computer 432. If, at step 1710, the patient has not been assigned a card, he is interviewed and, at 1716, the data from the interview is formatted and stored on a memory card. At step 1718, data on the card is printed so that the patient may examine and correct it. If any corrections are needed, step 1718 branches to step 1716 to enter the corrections.

After step 1718, when the patient has a card and the data on the card is correct, step 1720 is executed. In this step, an identifying wrist band, such as the band 140 described above in reference to FIG. 1d, is physically attached to the patient and the bar-code on the band is read and stored in the memory card.

When the patient is taken to his room, the card is inserted into the patient station 210 as set forth above in reference to FIG. 2 and the identification and other data is read from the card and stored locally in the card buffer area of the patient station, 210. If the card is removed, the data in this buffer is automatically invalidated and must be read from the card again. Accordingly, if the memory card 110 is a magnetic stripe card, data in the buffer is desirably written onto the card before it is removed. This may be accomplished, for example, by requiring a button on the patient station to be pressed before the card may be removed. This button invokes a routine in the patient station microcomputer 414 which transfers the contents of the card buffer onto the card and then signals, for example, by causing a light to blink, that the card may be removed.

When the patient's food trays are prepared in the hospital kitchen, the central computer 432 is first checked to determine if the patient is still in his room (i.e. if his card is still engaged) and if his diet has been changed. This information is obtained directly from the patient station 210. When the tray is prepared, a sticker containing the patient's bar-code identification information and room number is attached to the tray. When the orderly delivers the tray, he scans the bar-code on the patient's wrist and the bar-code on the tray using the light pen at the patient station located near the patient's bed. If the bar-codes match, the patient station 210 emits an acknowledging beep and notifies the central computer that the tray has been delivered. If the bar-codes do not match, the patient station 210 emits an alarm tone. In this instance, the orderly may take the tray to the closest nurse station to determine what type of error occurred and how it may be corrected. Alternatively, this check could be performed by the orderly using a portable nurse station 2310 shown in FIGS. 4 and 23. The same procedure could be used to deliver radiographic images or medical test results to a patient's bedside.

Alternatively, if the patient card 110 has only limited memory storage capability, it may contain only the patient identification data and the data from the interview could be stored directly in central computer 432. In operation, when patient memory card is linked to a portable nurse unit or a patient station, this identification data is read from the card and transmitted via an infrared transmitter or other network link to a central nurse station and then to the server 430 and central computer 432. From this identification data, the already entered data could be downloaded temporarily to the sending unit and only maintained while memory card is coupled to the unit. Upon removal of the patient memory card from the particular unit being used, the downloaded patient information is desirably invalidated.

In FIG. 17b, when a patient leaves the hospital, he presents his card at the administration desk and the card is coupled to the central computer 432 which, at step 1730, records the exit time and generates billing information. At steps 1732 and 1734, the central computer notifies housekeeping and the hospital kitchen to prepare the bed for the next patient and to make no more food trays for the patient. Step 1736 checks for any equipment that was assigned to the patient and marks the equipment as being available in a central database.

Figure 17C:
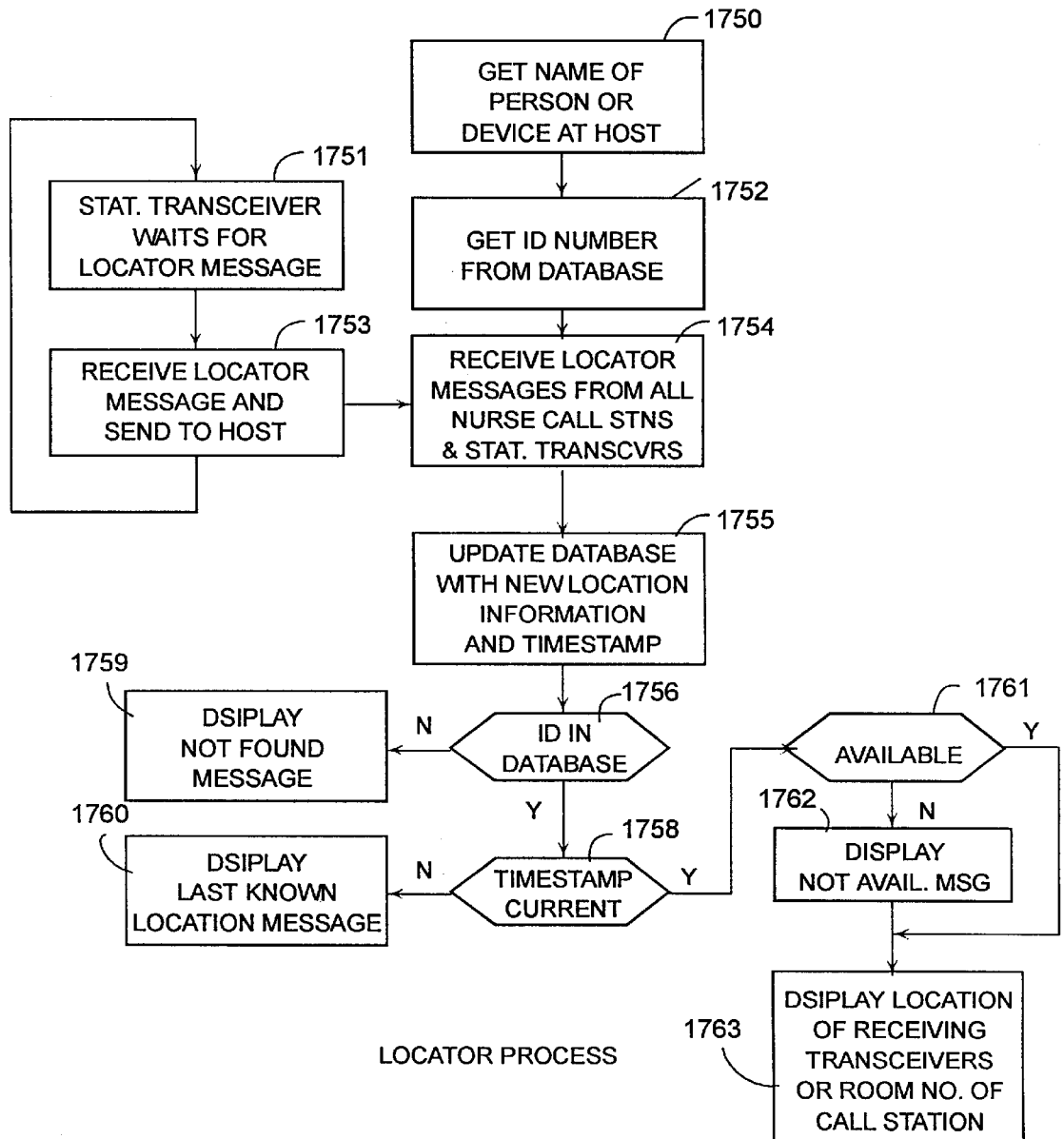

FIG. 17c illustrates how the memory cards 110 and 110' may be used in an automatic locator system. This is an automatic system because the identification badge continually transmits an identification signal and the central computer is continually monitoring these signals to update the location of the badge. Thus, this locator system does not require the computer to process a particular request before it locates an individual.

Referring to FIG. 17c, at step 1750 a user identifies the person or piece of equipment to be located to the central computer 432. At step 1752, the central computer searches the database for the entered name and finds the corresponding ID number.

As a continuing process, each of the stationary transceivers waits, at step 1751, to receive a locator message. When a person wearing a staff badge enters a room, the fixed transceiver in the room receives the transmitted ID number in a locator message and, at step 1753, sends the received ID number together with an address for the remote transceiver to the central computer 432. Patient identifiers and room numbers are sent to the central computer only when they are changed. That is to say when a patient card is either inserted into or removed from a patient station.

At step 1754, the central computer periodically receives messages from all of the fixed transceivers and from any of the patient stations which may have changed. At step 1755 it updates the entries in the data base to reflect the new location for each received ID number. Each location entry overwrites a previous entry and is marked with a timestamp. The two most recent locations are kept for each individual in the database. Using the two entries and their timestamps, the locator system can provide not only the location of the individual but his or her direction of travel as well.

At step 1756, the central computer determines if the ID number corresponding to the requested person or piece of equipment is in the database. If it is not, the central computer displays a message on the user's display terminal indicating that the requested entity is not present in the hospital.

If the ID number is in the database, the central computer, at step 1758 determines if the location entry is current. If not, that is to say it the timestamp is more than, for example, five minutes old, the central computer, at step 1760, displays a message indicating that the requested entity has not been located recently and indicates its last known location and direction of travel.

If the ID number of the requested entity is in the database with a current timestamp then the central computer, at step 1761, checks the database entry for the entity to determine if it is available. A piece of equipment may be marked as not available if it is currently being used. A person may be marked as unavailable if he or she is engaged in an important assignment, such as responding to a "code-blue," alert. If the requested entity is not available, the central computer displays a message to that effect as step 1762. It the entity is available, a message is displayed, at step 1763, indicating the current location of the entity.

The emergency alert process illustrated in FIG. 17d builds upon the locator process shown in FIG. 17c to produce a process that attempts to automatically assemble a team of specialists and equipment to respond to an emergency situation. In the first step in the process, step 1770, the central computer 432 determines the types of specialists and equipment that are needed. This information may be entered from a nurse station based on the condition of a patient. The condition may be sent to the nurse station with a patient initiated nurse call request, as set forth above, or it may be sent automatically when the patient station senses an alarm condition, such as an irregular heart beat, from data provided by external equipment.

It is contemplated that the nurse station would display a menu of, for example, five types of emergency situation, each requiring a different mix of personnel and equipment. One of these situations would be indicated to the central computer 432. This indication would provide the central computer with the types of specialists and equipment needed and an indication of which nurse station initiated the call.

Alternatively, an emergency alert may be generated by a caregiver pressing the switch 1118 on her badge transceiver. In this instance, a set of specialists and equipment would be assembled that could handle any situation.

At 1772, the computer 432 searches its personnel and equipment database to obtain a list of identifiers for each specialty type and for each type of equipment. At step 1774, the computer 432 uses the locator process shown in FIG. 17b to determine the location and availability of each individual and piece of equipment on each list. At step 1776, The computer conditions the PBX to ring the telephone set that is closest to the selected entities with a distinctive ring.

In response the distinctive ring someone near the telephone would answer it and either listen for the emergency message or see the message on the telephone's LCD display. If the requested individual has received the message, he may press the switch 1118 to indicate that he has responded. When this response is sensed, the computer 432 will add the person to the assembled team.

Otherwise, the requested person would be notified that he is needed by the individual who answers the phone. The requested person would acknowledge receiving the summons by pressing the button 1118 on his badge. If a piece of equipment is being requested, the individual who answers the phone may press the response button-on the badge attached to the requested piece of equipment and send it to the requested location.

At step 1778, the central computer waits for a fixed amount of time, for example 30 seconds, to determine if all of the selected individuals and equipment have responded. If so, the responders are marked as unavailable and a full response message is displayed at the initiating nurse station 300 or at the nurse station closest to the individual who initiated the emergency alarm condition. This message includes a list of all of the equipment and personnel that have responded.

If, at step 1778, the central computer determines that some needed specialists or equipment have not responded, both the responding and non-responding entities are deleted from the lists. These lists are then passed to step 1774, described above, to locate the next closest specialists and equipment.

The processes outlined above illustrate a few applications of a distributed processing system which may be coupled to multiple personal databases. All of these applications are in a hospital environment. A system of this type has significant medical and non-medical uses outside of a hospital environment.

Figure 18:
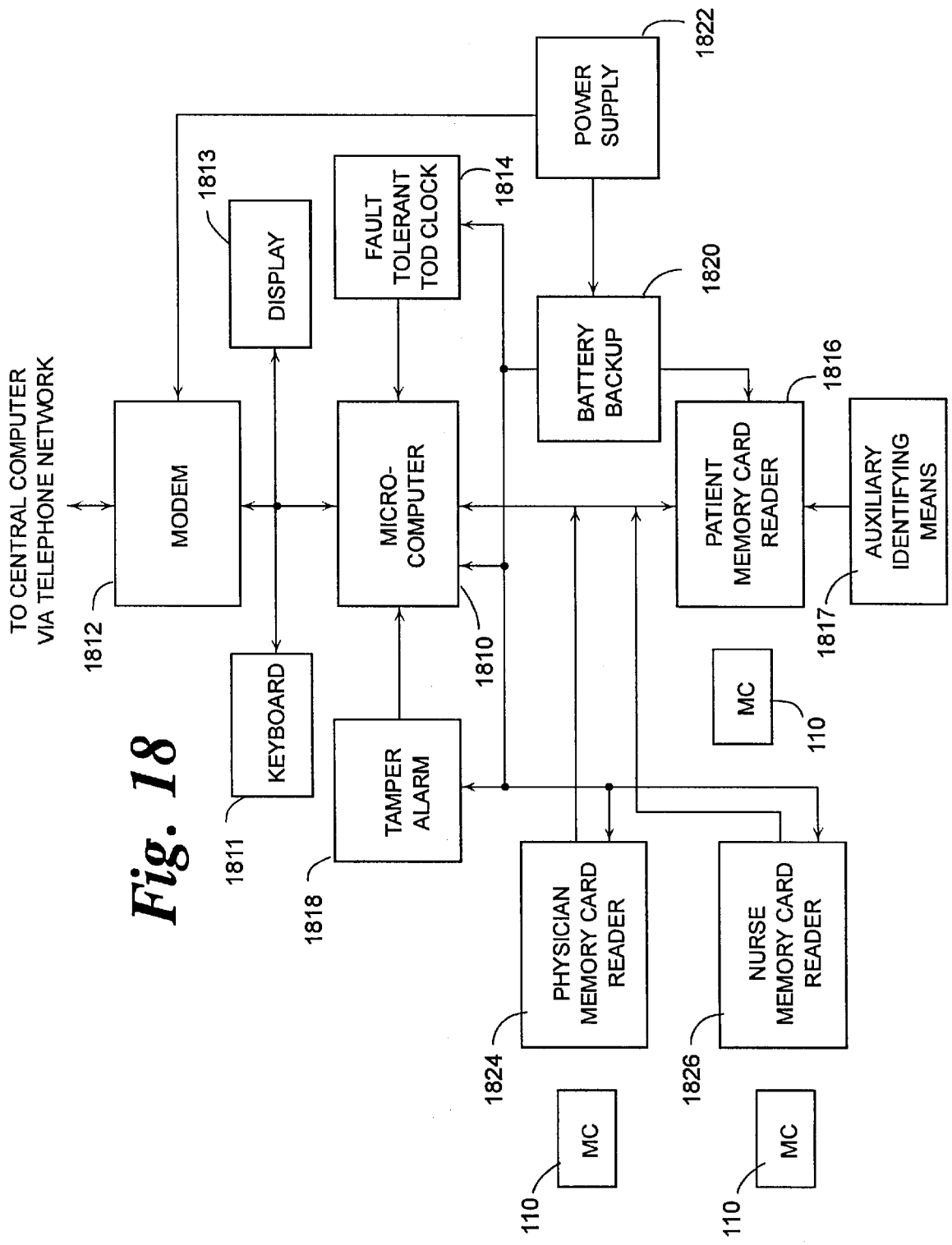
FIG. 18 is a block diagram of a system which monitors physician services and which includes an embodiment of the present invention.

FIG. 18 is a block diagram of a secure billing system for physicians and other professionals whose charges are based on the amount of time spent with a patient or client. To simplify the description, it is assumed that the system is located in a physician's office and is used for billing Medicare for services provided by the physician.

In general terms, the system operates as follows. Each physician would be provided with one system. When the physician is attending to each patient, that patient's card is inserted into the system. Also, the card of a third party, for example, an attending nurse, is inserted to the system. The system records identifying information from the cards and is provided, either by the doctor or by other office personnel with a diagnosis for the individual. The reason for the third party card is to reduce the possibility of fraud, and to provide an identifiable corroborating witness.

At the end of the day, the system automatically dials up a central computer and transfer the day's billing information. This information is then processed to determine the amount due to the physician. This type of system would speed the processing of Medicare bills by eliminating much of the paper work. In addition, it is advantageous because it is more difficult to generate fraudulent bills using a system of this type.

As shown in FIG. 18, an exemplary system of this type includes a microcomputer 1810 which is coupled to a modem 1812 through which data may be communicated to the central database. In addition, the microcomputer 1810 is coupled to a keyboard 1811 and display device 1813 which may be used to enter data, such as a diagnosis or prescription information into the computer system. These components exist in many commercially available personal computer systems, for example, those that are compatible with the IBM Personal Computer.

In addition to these basic computer components, the system shown in FIG. 18 includes a fault tolerant time of day (TOD) clock 1814, a tamper alarm system 1818, a patient memory card reader 1816, two staff memory card readers 1824 and 1826, and a power supply 1822 with a battery backup 1820. The system may also include auxiliary identifying means 1817, such as a commercially available fingerprint reader which can compare a person's fingerprint against data describing the fingerprint which is stored on the memory card 110.

The fault tolerant TOD clock 1814, tamper alarm system 1818 and battery backup 1820 ensure that the data provided by the billing system is accurate. The fault tolerant clock may be, for example, of the type described in a paper by D. Davies. et al. entitled "Synchronization and Matching in Redundant Systems", IEEE Trans. on Computers, June, 1978, pp 531–539, which is hereby incorporated by reference. The nature of the tamper alarm system would depend on the construction of the overall billing unit. At a minimum, the tamper alarm would detect: any attempt to open the case enclosing the unit and the insertion of an object other than a data card into the data card reader. Any detected tampering would condition the system to both sound an audible alarm and record the tampering event. Optionally, the tamper alarm system could also disable the device. Any recorded tampering events are sent to the central database with the billing information.

The power supply 1822 and battery backup 1820 provide power to the tamper alarm 1818, microcomputer 1810, fault tolerant clock 1814, patient card reader 1816 and staff memory card readers 1824 and 1826 even when no power is applied to the billing unit. The power supply and battery backup may be any of a number of commercially available components. The exact type of components used would depend on the power requirements of the system and on the types of interruption that may be expected.

Figure 19:
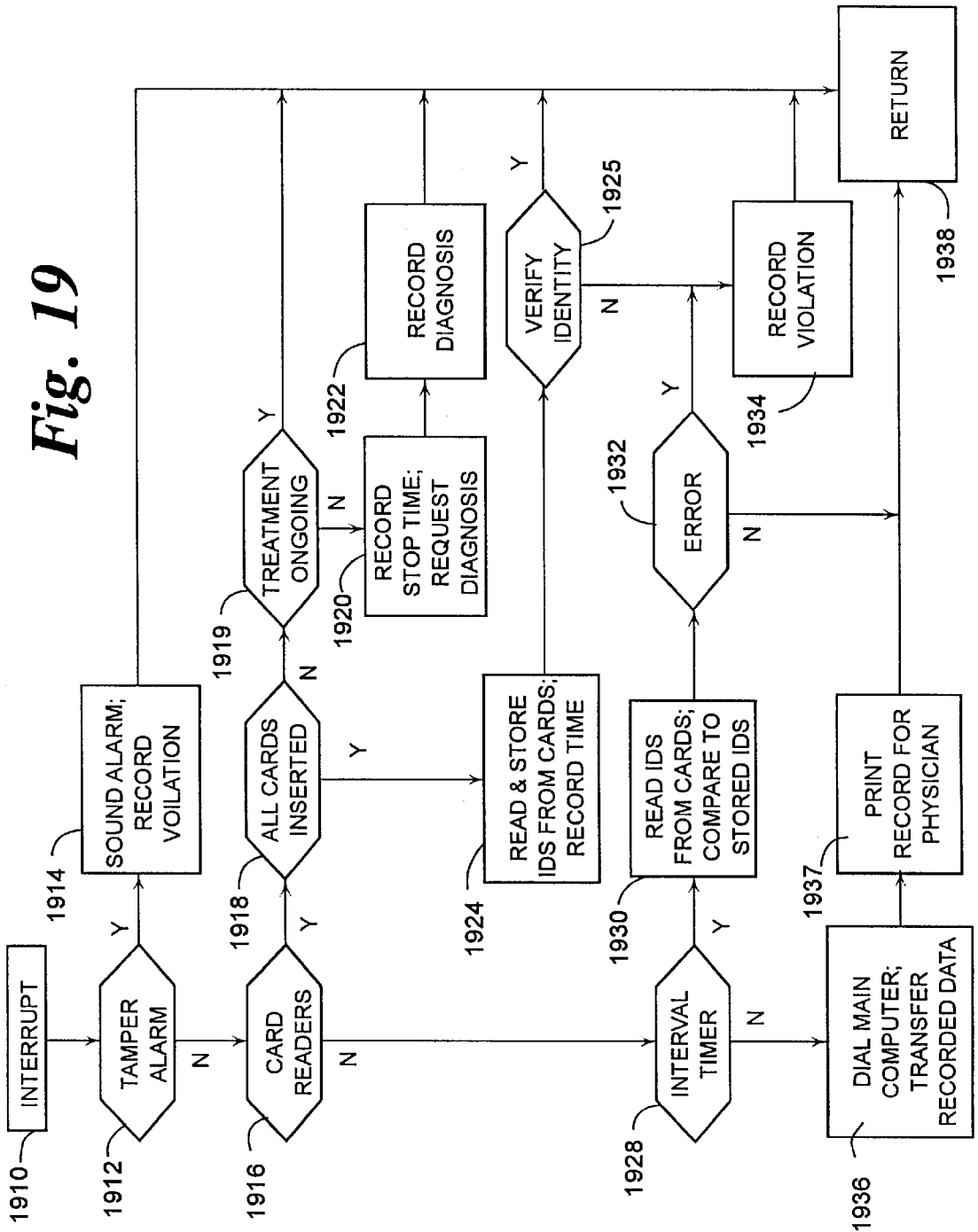
FIG. 19 is a flow-chart diagram which illustrates the operation of the monitoring system shown in FIG. 18.

FIG. 19 is a flow-chart diagram which illustrates the program that controls the billing system shown in FIG. 18. This program is desirably stored on ROM located securely within the case of the unit. The process shown in FIG. 19 operates in the background of other processing performed on the microcomputer 1810. Thus, the entire unit may be sold as a general purpose computer system for word processing or general billing, while the automatic billing function runs in a background mode.

In this configuration, care must be taken to ensure that no program which can interfere with the automatic billing operations is allowed to run on the system.

The first step in the program, step 1910, receives an interrupt. The interrupt may be from the tamper alarm 1818, patient memory card reader 1816, staff memory card reader 1830, or fault-tolerant TOD clock 1814. If, at step 1912, the interrupt is from the tamper alarm, step 1914 is executed which sounds the audible alarm and records the tampering event. After recording the tampering event, the process, at step 1938, returns control to the program that was running when the interrupt occurred.

If, at step 1916, the interrupt is caused by any of the memory card readers 1816, 1824 or 1826, step 1918 is executed to determine if all cards are inserted. If all cards are present, then a card has just been inserted, step 1924 is executed to read the identifying information from all of the cards and store this information and the current time for later transmission to the central database. Optionally, after step 1924 has been executed, step 1925 may be invoked to verify the identity of the patient and thy attending physician. In the exemplary embodiment, this identification is accomplished by comparing fingerprint information stored on the cards with the actual fingerprint of the patient and the physician. If the identity is verified, control is transferred to step 1938, described above. Otherwise, a violation is recorded at step 1934 and control is returned to the foreground program at step 1938.

If, at step 1918, the patient card reader interrupt occurs when less than all of the cards are inserted, step 1919 is executed to determine if a treatment is currently in progress. If so, then one of the patient card, physician card or nurse card was removed to cause the interrupt. In this instance, step 1920 is executed to terminate the treatment, record the stop time and request a diagnosis for the patient. Either the physician or other office personnel enters the diagnosis which is recorded at step 1922. After step 1922, control is transferred to step 1938, described above. If, at step 1919, a treatment was not in progress and at least one card is missing, control is returned to the foreground program via step 1938 to await the insertion of the remaining card or cards.

In the exemplary embodiment of the invention, if the interrupt is not caused by the tamper alarm or one of the card readers, then it must be caused by the clock circuit 1814. At step 1928, the process determines if the clock interrupt is from the interval timer. If so, step 1930 is executed to read the identification information from each of the cards and compare it to the stored identification for each individual. If any difference is detected at step 1932, a violation is recorded at step 1934. After step 1934 or if no error is detected at step 1932, control is transferred to step 1938.

If the clock interrupt is not an interval timer interrupt then it is an indication that it is time to transfer the accumulated billing data to the main computer. In this instance, step 1936 is executed. This step dials the main computer and transfers the recorded data along with data identifying the physician. In addition, the computer, at step 1937, may condition a printer (not shown) to print out a record of the data transferred for the physician's records. After step 1937, control is transferred to step 1938 to return control to the program running at the time the interrupt occurred.

The system described above in reference to FIGS. 1–16 may be used in a hospital environment to monitor the usage of controlled substances such as prescription drugs. FIGS. 20*a* through 20*e* illustrate an exemplary system for auditing drugs which are stored in a drug locker. The invention does not significantly impede the access of individuals to the drug locker, unlike if using normal physical security measures such as a locker from heavy gauge steel and placing a lock on the door.

Figure 20A:
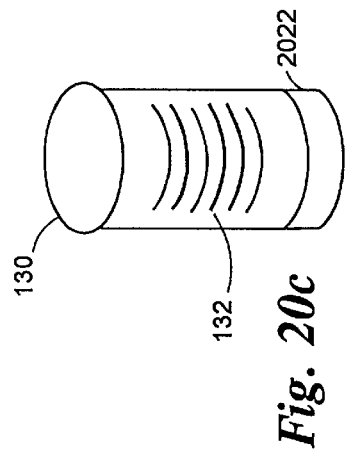
FIG. 20a is a cut away top plan view of a drug locker which includes an embodiment of the present invention.

FIG. 20*a* is a cut-away top plan view of a drug locker 2010 in accordance with this embodiment of the invention. As shown, the drug locker is a physically secure cabinet, having a door 2011 that may be locked by lock 2012 and containing several medicine containers 130. A stationary transceiver 2014 of the type described above with reference to FIG. 15 is positioned close to the drug locker. This stationary transceiver, however, is coupled to receive signals from a keyboard unit 2015. In addition, inside the locker a bar-code reader 2016 is positioned next to the door 2011 and a removal detector 2018 is concealed in the floor of the locker, positioned so that any containers removed from the locker must be passed over the detector 2018.

Figure 20C:
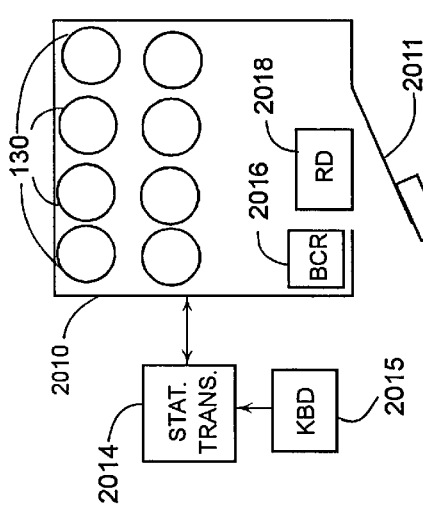
FIG. 20c is a perspective drawing of a medication container which may be used with the drug locker monitoring system shown in FIG. 20b.

The detector 2018 may be a resonance detector of the type commonly found in libraries and retail stores which detects an induced resonant signal in a passive reactive component 2022 attached to the bottom of each medicine container 130, as shown in FIG. 20*c*.

Figure 20B:
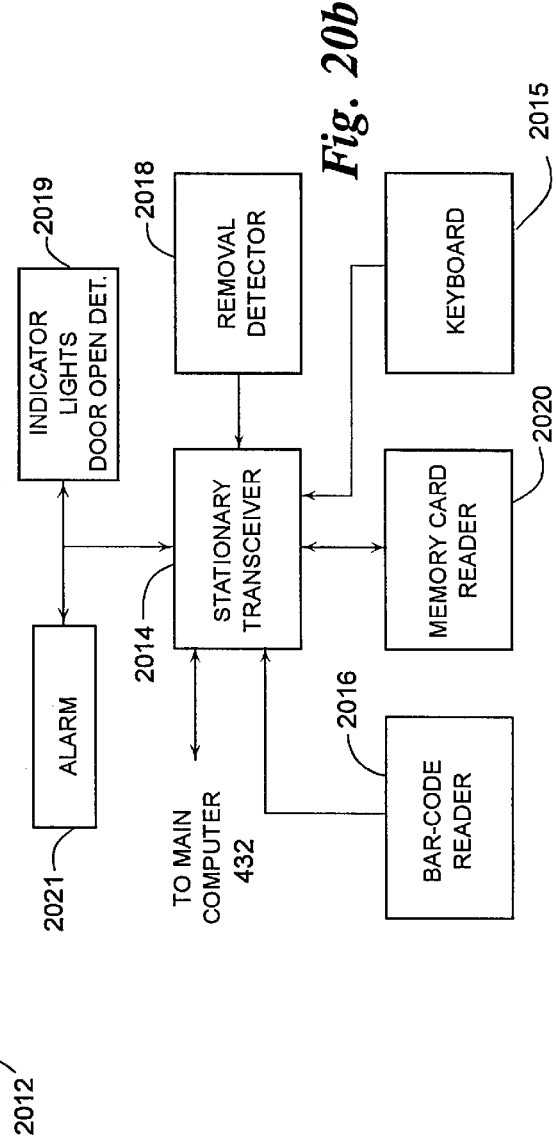

FIG. 20*b* is a functional block diagram of the drug monitoring system used in the drug locker. In addition to the components shown in FIG. 20*a*, the system shown in FIG. 20*b* includes an audible alarm 2021, indicator lights and a door open detector 2019. All of the system elements 2016 through 2021 are configured to be controlled by the microcontroller 1512 of the stationary transceiver, as shown in FIG. 15. The stationary transceiver is, in turn, in communication with and controlled by server 430 and central computer 432.

FIG. 20*d* is a flow-chart diagram which illustrates the portion of the drug audit process that utilizes the circuitry shown in FIG. 20*b*. At step 2050, whenever a badge transmitter normally worn by a hospital staff member is within a preset distance, for example, one meter of fixed transceiver 2014, the transceiver receives the identification signal from the badge at step 2052. Next, at step 2057, the keyboard and display unit 2015 prompts for a personal identification number (PIN) stored in the central computer 432 as being associated with this badge. This PIN may be the same number as is used to obtain the badge from the base unit or, for enhanced security it may be a different number.

At step 2058, the transceiver sends a request to the central computer 432 to compare the identification signal and PIN with a predetermined list of authorized personnel. Alternatively, this compare operation may be performed using the microcontroller 1512 of the stationary transceiver 2014 using an authorized list that is either stored locally, at the server 430 or at central computer 432.

If, at step 2054, the ID signal is not found on the list, access to the drug locker is denied at step 2060 and the unauthorized attempted access will be recorded on central computer 432.

If at step 2058, the identification signal is found on the list and the PIN is proper, access is granted by fixed transceiver 2014 sending a signal to release lock 2012 on door 2011.

If the individual is authorized to access the locker, step 2064 records the identifying information and the authorization information on the central computer 432. As each medicine container is removed from the locker, it is scanned by the bar-code reader. When the bar-code information has been scanned, the process changes a value in a memory location to indicate that the container may be removed.

The actual use of the prescription medicines may also be monitored from the information provided to the central computer 432. This information indicates the individuals who had access to the drug locker, the time they removed and returned the medicines, the patients to whom the medicines were administered, the prescribed doses and, optionally, the amount of medicine that was removed and the amount that was returned. This entire auditing process could take place without significantly impeding access to the drug locker.

FIG. 20*e* illustrates the process of monitoring the distribution of medicine that is obtained in step 20*d*. The steps in this process are executed as the medicine is given to the patients. At step 2080, the nurse scans the patient bar-code on the wrist band 140 using either the patient station bar-code reader or the portable nurse station bar-code reader. Next, at step 2082, the bar-code on the medication is scanned. At step 2086, either the patient station computer 414 or the central computer 432, both shown in FIG. 4, compares the medication information with stored prescription information for the patient. If a match is found, then, at step 2090, the prescribed dosage of the medicine is recorded in the central computer 432 as having been distributed and the administration of the medication is recorded in the patient's record in the central computer, patient station computer and, optionally, on the patient's memory card.

Figure 21B:
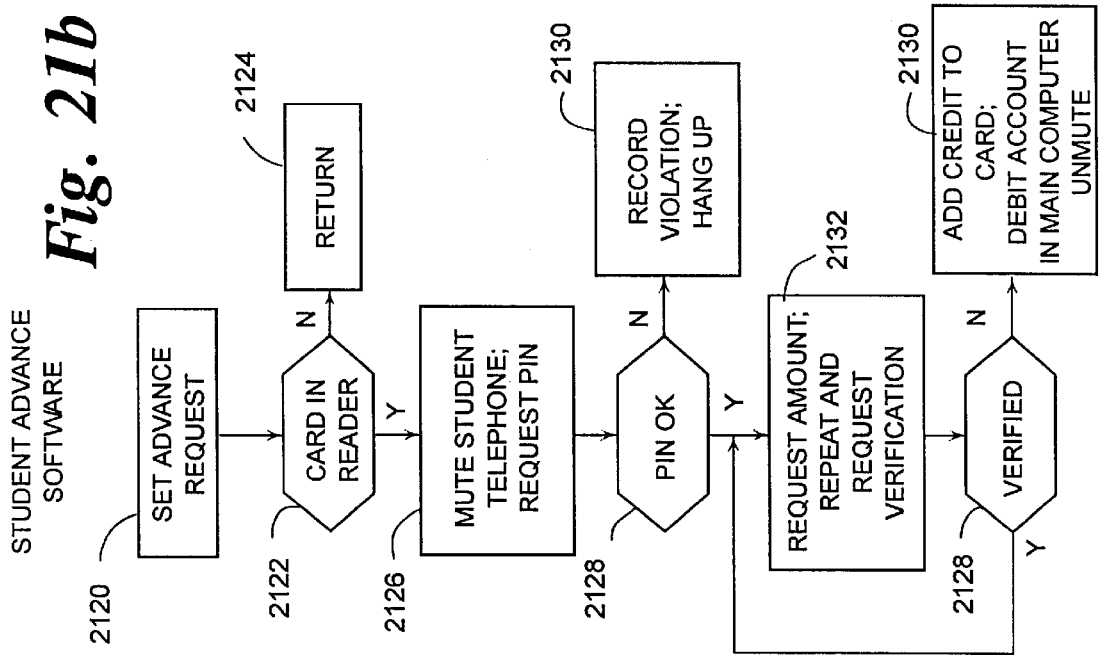
Figure 21A:
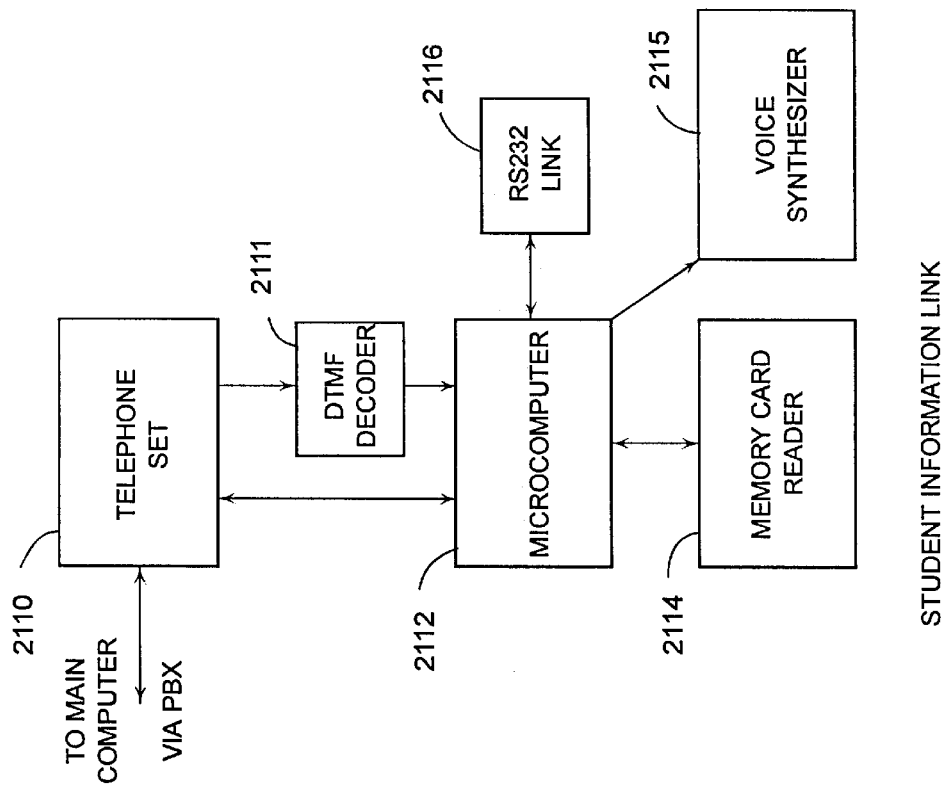
FIG. 21a is a block diagram of a student information system which includes an embodiment of the present invention.

All of the applications described above relate in some manner to the health care field. It is contemplated, however, that significant applications for the invention exist in areas other than health care. FIGS. 21*a* and 21*b* relate to an application of the invention which establishes a student information link in through a special telephone set in the student's dormitory room.

As shown in FIG. 21*a*, the telephone set 2110 is coupled to a dual-tone multifrequency (DTMF) decoder 2111, microcomputer 2112, a memory card reader/writer 2114, a voice synthesizer and a digital data port, such as an RS232 link 2116. A data link between a central computer (not shown) or network server (not shown), the memory card reader/writer 2114 and the RS232 link 2116 is established through the telephone set 2110 which is coupled to a PBX (not shown).

In this configuration, the memory card may be used as a standard identification card for directly billing telephone calls or to allow access to student records, assignment information, or a student bulletin board, via a personal computer coupled to the RS232 port.

In addition, the memory card may be used for a novel form of electronic funds transfer (EFT) as illustrated in FIG. 21b. The following scenario illustrates how this system may be used. The student and the parent are in a discussion and the student requests funds from his parents. At step 2120, the parent enters an initial code by depressing a particular sequence of buttons on the telephone. At step 2122, the microcomputer 2122 determines if the card is in the reader. If it is not, a distinctive tone or a voice message from the synthesizer 2115 is emitted and the telephone conversation continues normally.

If, however, at step 2122, the card is in the reader 2114, step 2126 is executed in which the student telephone is muted and the voice synthesizer 2115 is used to prompt the parent for a personal identification number (PIN). At step 2128, if the PIN is correct, the voice synthesizer requests the parent to enter an amount to enter on the debit card, repeats the request using the voice synthesizer and requests verification from the parent. If, at step 2134, the parent verifies the amount entered at step 2132, step 2136 is executed in which the amount is added as a credit to the debit card and a debit entry is made on a bill to be sent to the parents. If the amount is not verified at step 2134, control is transferred to step 2132 for the parent to reenter the amount or to cancel the transaction.

If the PIN is not correct at step 2128, step 2130 is executed in which the microcomputer 2112 records a violation on the central computer 432 and either unmutes the student telephone allowing the conversation to resume, or disconnects the telephone.

In this embodiment of the invention, the credit on the card may be used only at specified locations on campus, for example, at the book store. As the funds are spent, a record is made of the purchases and this record is sent to the parent along with the debit entry on the next account statement.

It is also contemplated that a locator and emergency alert system such as described above in reference to FIGS. 11 through 17 may be used in a corrections environment to determine the location of prison guards and trustees and to allow a prison guard to signal an emergency alert. This locator system may also be used as an automatic key station. For this use of the system, a network of the same type as the network N2 shown in FIG. 14 may be set up inside of a factory or office building. In this network, each of the stationary transmitters is programmed to continually receive identification messages transmitted by the badges. As a guard, wearing a badge transmitter passes the transceivers, the identity information is transmitted from the card and stored in a central computer as passing through the transceiver. This system has advantages over the traditional key station system since the guard need not carry the bulky clock device and since the location of the stationary transceivers may be concealed making it more difficult for the guard to defeat the system by taking a different route.

System Configurations and Communications

Figure 24:
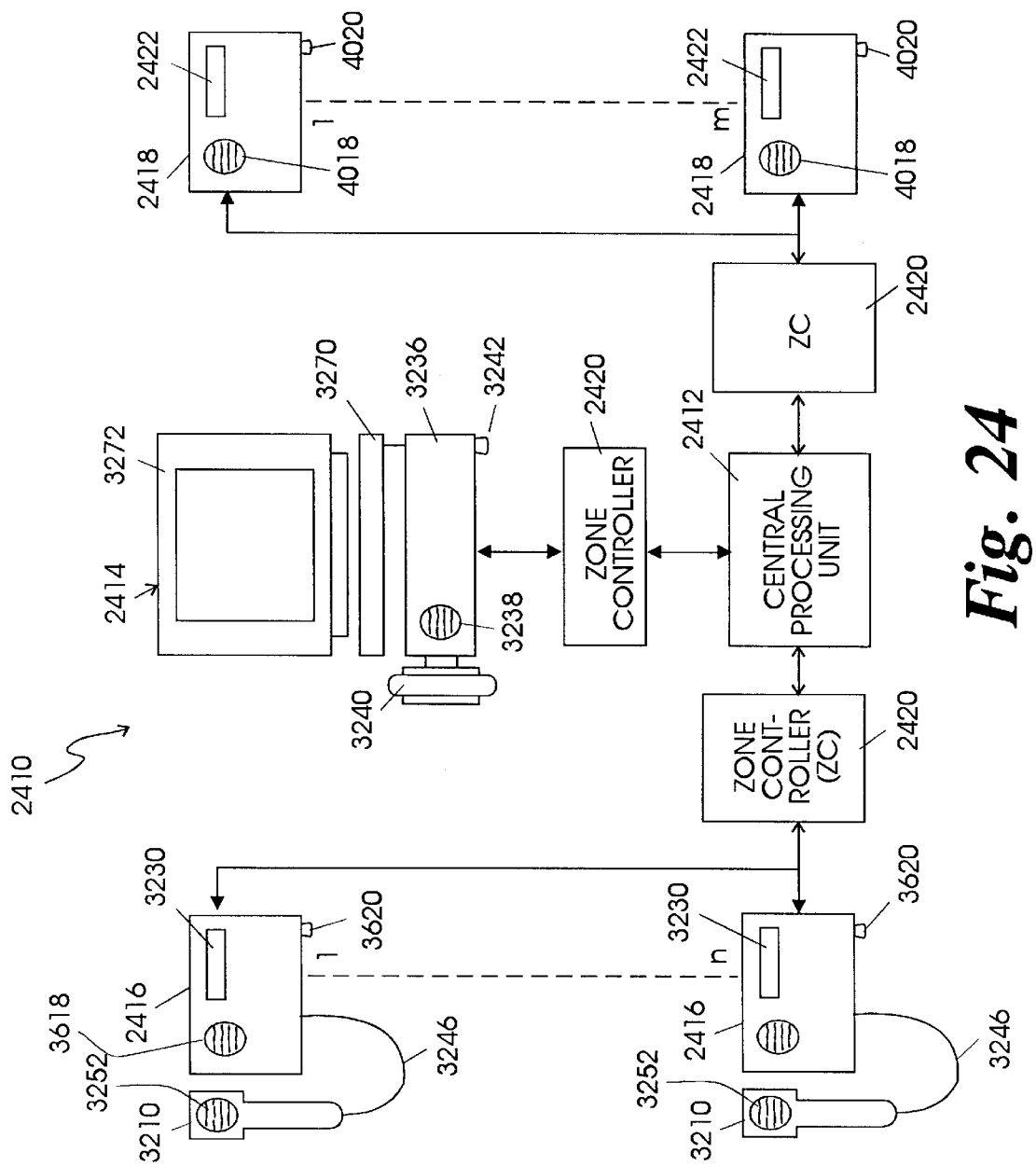
FIG. 24 is an illustration of the components of one embodiment of the patient care and communication system configuration of the present invention.

FIG. 24 is an illustration of the major components of the patient care and communication system according to the present invention, which includes central processor unit (CPU) 2412, nurse control stations 2414, patient stations 2416, staff stations 2418 and zone controllers 2420. Generally, the nurse control stations 2414 are installed at nurse stations located in various areas of the hospital or health care facility and provide a communication link to patients in their rooms. The patient stations 2416 are installed in patient rooms and can be configured to correspond to one patient or to multiple patients. The patient stations 2416 include patient station display 3230, speaker 3618, microphone 3620 and patient control unit 3210, all of which will be described in more detail below.

The staff stations 2418 are preferably installed in locations frequently occupied by other staff members in the hospital, such as staff locker rooms. Staff stations 2418 include staff station display 2422, speaker 4018 and microphone 4020, all of which will also be described in more detail below. The zone controllers 2420 include shared-RAM (S-RAM) memory 2512 (shown in FIG. 25) which is utilized as a buffer memory for data received from either CPU 2412 or from any of the above noted stations, hence the term shared-RAM.

As will be described in more detail below, the various types of stations which are positioned at different locations within the hospital interact with the aid of the CPU 2412 to perform numerous operations to reduce the information overload currently plaguing hospital staff members. Examples of the operations involving CPU 2412 include a call priority operation which prioritizes incoming calls (or messages) to nurse control station 2414 based upon the type of message received, so that staff members respond to the highest priority calls first. For example, if the incoming message relates to a fault in a smoke alarm secured in the patient's room, that message will be given the highest priority. Another operational example is a nurse follow operation which allows staff members to selectively route incoming calls directed to a nurse control station, to selected patient stations and/or staff stations so that when the staff members attending the nurse control station are required to leave the area, incoming calls to that station can be routed to locations where appropriate staff members can respond to the call. Another operational example is a voice paging operation which allows staff members to communicate with selected patient stations 2416 and/or staff stations 2418 from the nurse control station 2414. The interaction between the stations when performing these exemplary operations or tasks, as well as other operations, is conducted via a communication link which will be described in more detail below.

Figure 26:
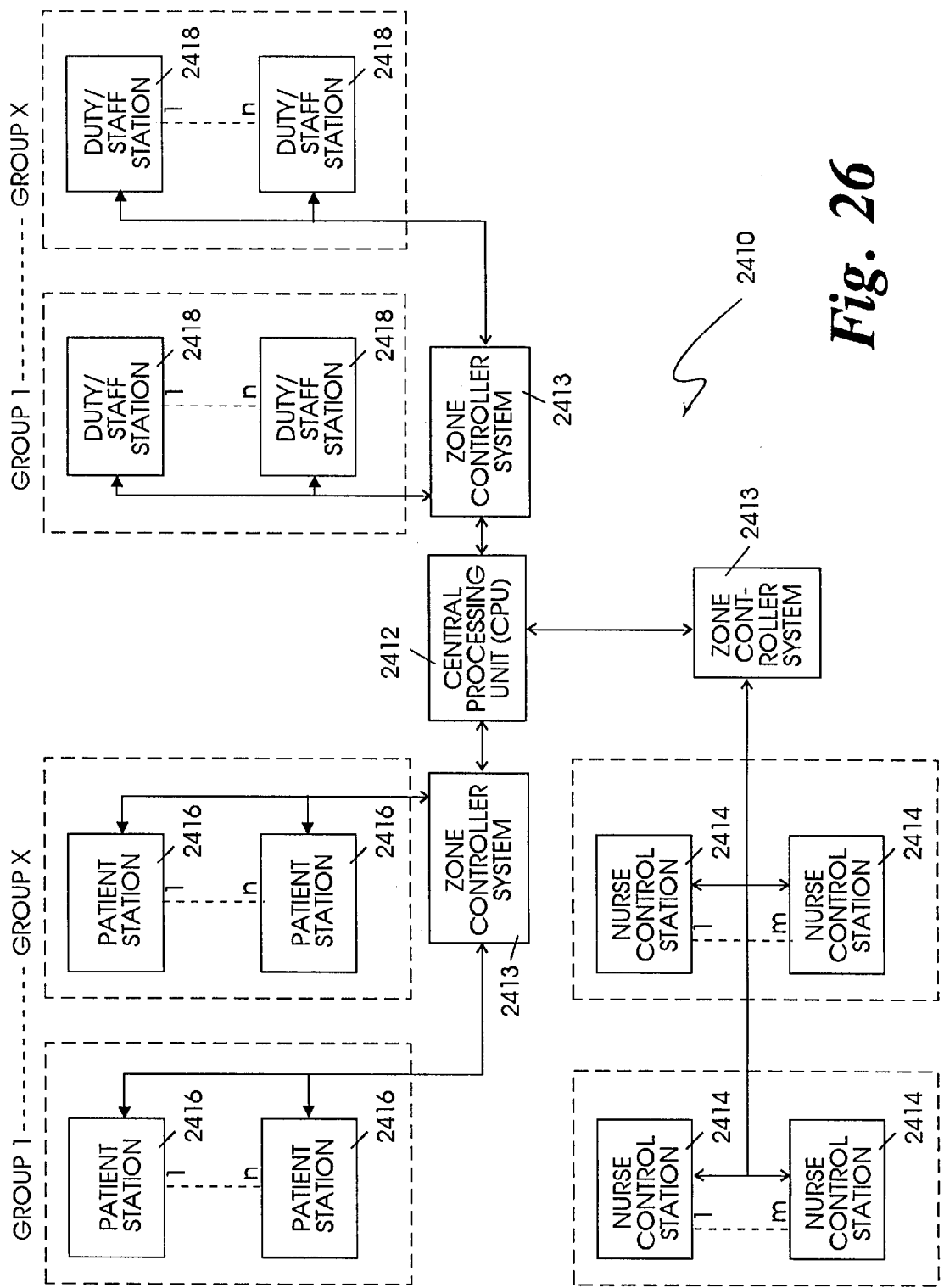
FIG. 26 is a functional block diagram of an another alternative embodiment of a system configuration of the present invention, illustrating grouping arrangements for the stations.

FIG. 26 illustrates the major components of system 2410 arranged in groups. As shown, CPU 2412 of the system of the present invention is configured, dimensioned and adapted to interface through zone controller systems 2413 with a predetermined number of station groups of patient stations 2416, staff stations 2418, and/or any combination thereof (e.g., the number of groups ranging between 1 and x, where "x" is preferably 8). Each station group includes between 1 and "n" stations, where "n" is preferably 35, and a predetermined number of station groups can be assigned to between 1 and "m" nurse control stations 2414, where "m" is preferably 8. For example, if a ward in a hospital has one hundred patient rooms (numbered from 100 to 200) which are single occupancy rooms, a staff locker room (Room 201) and a staff kitchen (Room 202), one patient station 2416 would be installed in each patient room and one staff station 2418 would be installed in the staff locker room and the staff kitchen. An exemplary array of station groupings (or the call assignment configuration) is shown in Table I below:

TABLE I

|  | RM1 | RM2 | RM3 ... RM32 | RM33 | RM34 | RM35 |
|---|---|---|---|---|---|---|
| GROUP 1 | 100 | 101 | 102 ... 132 | 133 | 201 | 202 |
| GROUP 2 | 120 | 121 | 122 ... 152 | 153 | 201 | 202 |
| . | | | | | | |
| . | | | | | | |
| . | | | | | | |
| GROUP 8 | 154 | 155 | 156 ... 186 | 187 | 201 | 202 |

As shown in this exemplary call assignment configuration, rooms 100 through 133, 201 and 202 are assigned to station group 1. Rooms 120 through 153, 201 and 202 are assigned to station group 2 and rooms 154 through 187, 201 and 202 are assigned to station group 8. The station groupings can overlap in room coverage, thus, as illustrated in table I above, station groups 1 and 2 both include rooms 120 through 133.

In addition to the station groupings, the system of the present invention is configured so that each station group is assigned to a predetermined number of nurse control stations 2414. Table II below, illustrates an exemplary call assignment configuration for station groupings and their assignment to the nurse control stations 2414:

TABLE II

|  | Group 1 | Group 2 ... Group 8 |
|---|---|---|
| NCS1 | YES | YES ... YES |
| NCS2 | YES | NO ... NO |
| . | | |
| . | | |
| . | | |
| NCS8 | NO | YES ... NO |

In this exemplary configuration, communication transmitted by any of the stations assigned to station group one (rooms 100–133, 201 and 202) will be directed to nurse control station one (NCS1) and to NCS2 so that staff members attending either nurse control station 2414 can respond to the call. Communications transmitted by any of the stations assigned to station group two (rooms 120–153, 201 and 202) will be directed to NCS1 and NCS8 so that staff members attending either nurse control station 2414 can respond to the call. Communications transmitted by any of the stations assigned to station group eight (rooms 154–187, 201 and 202) will be directed to NCS1 so that staff members attending NCS1 can respond to the call.

In the preferred embodiment, the patient care and communication system of the present invention can include four call assignment configurations. To illustrate, the call assignment configurations can be utilized to automatically (or manually) assign stations (2416 or 2418) to station groups and station groups to nurse control stations 2414 for day operation, for evening operation, for weekend operation and/or for holiday operation.

Figure 27:
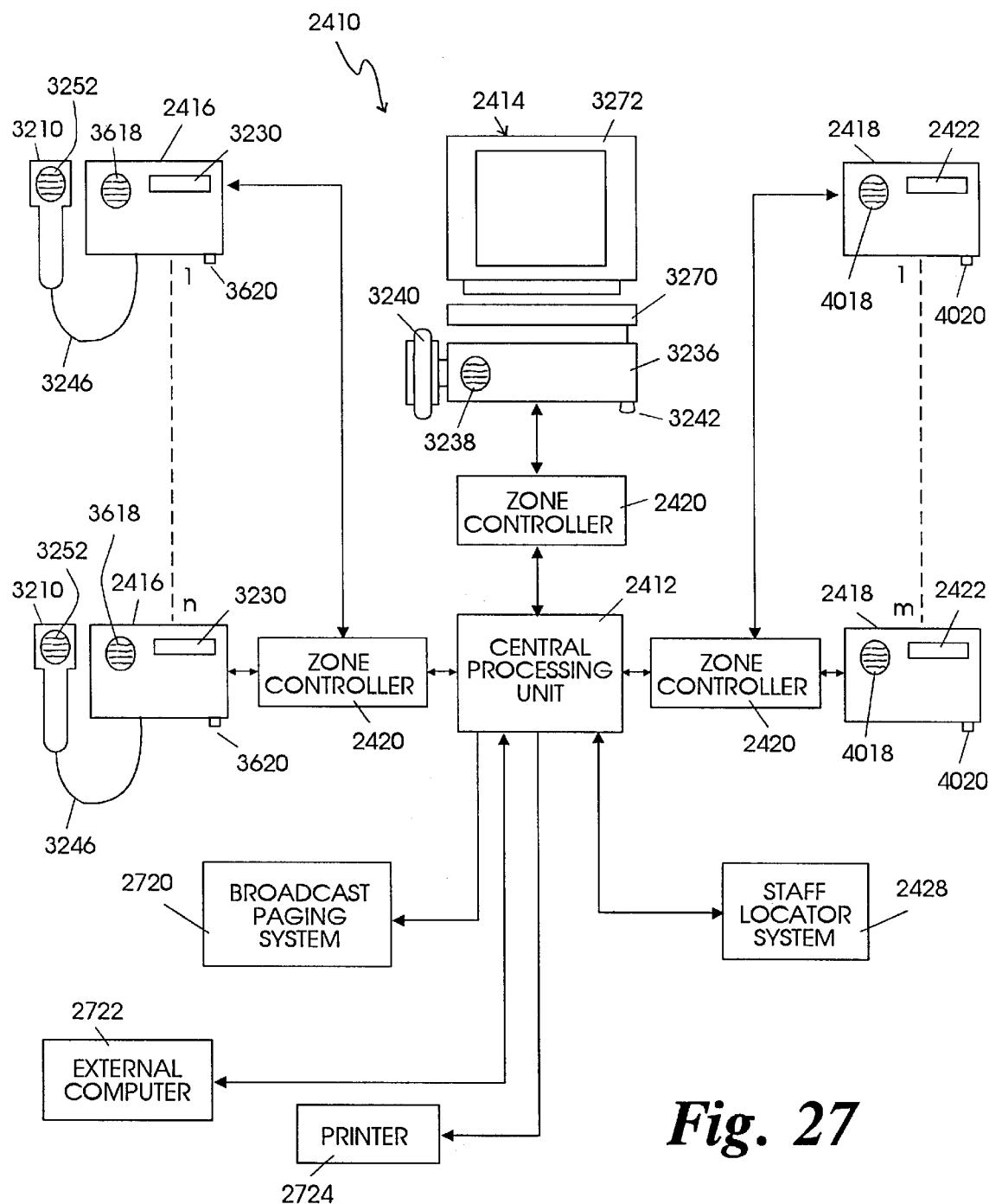
FIG. 27 is a functional block diagram of an another alternative embodiment of a system configuration of the present invention.

Referring now to FIG. 27 which illustrates an alternative system configuration in which, central processing unit 2412 is connected to external communication equipment such as broadcast paging system 2720, external computer 2722, printer 2724, and/or staff locator system 2428. Broadcast paging system 2720 may be utilized by the system of the present invention to locate staff members or other personnel who are not within the hospital or other health care facility. The broadcast paging system may be any known type capable of interfacing with a computer. Preferably, broadcast paging system 2720 and CPU 2412 communicate via serial communication ports connected to each device. Staff locator system 2428 may be provided to locate staff members anywhere in the hospital or other health care facility as described above with reference to FIGS. 1–23. In addition to locating staff members, staff locator system 2428 may be utilized to track or locate patients in the hospital. To utilize the staff locator system to locate patients, each patient is provided with an identification badge or bracelet 140 (shown in FIG. 1d) which includes the components as disclosed for identification badge 1111 worn by staff members and described above. The identification badge 1111 or bracelet 140 continually transmits the identification signal of the patient and central computer system 432 continually monitors the identification signal to update the location of the bracelet and the patient. The location information of the staff member or patient is transferred to CPU 2412 via data link 2726 (shown in FIG. 27) which may be any known type of communication link utilized to facilitate communication between computer systems. External computer 2722 interfaces to CPU 2412 and performs computing functions including extracting or inputting data stored or otherwise processed within CPU 2412. Printer 2724 may be utilized to extract hard copies of data stored or otherwise processed within CPU 2412 including problem reports generated by the system, as will be described in more detail below.

Figure 25:
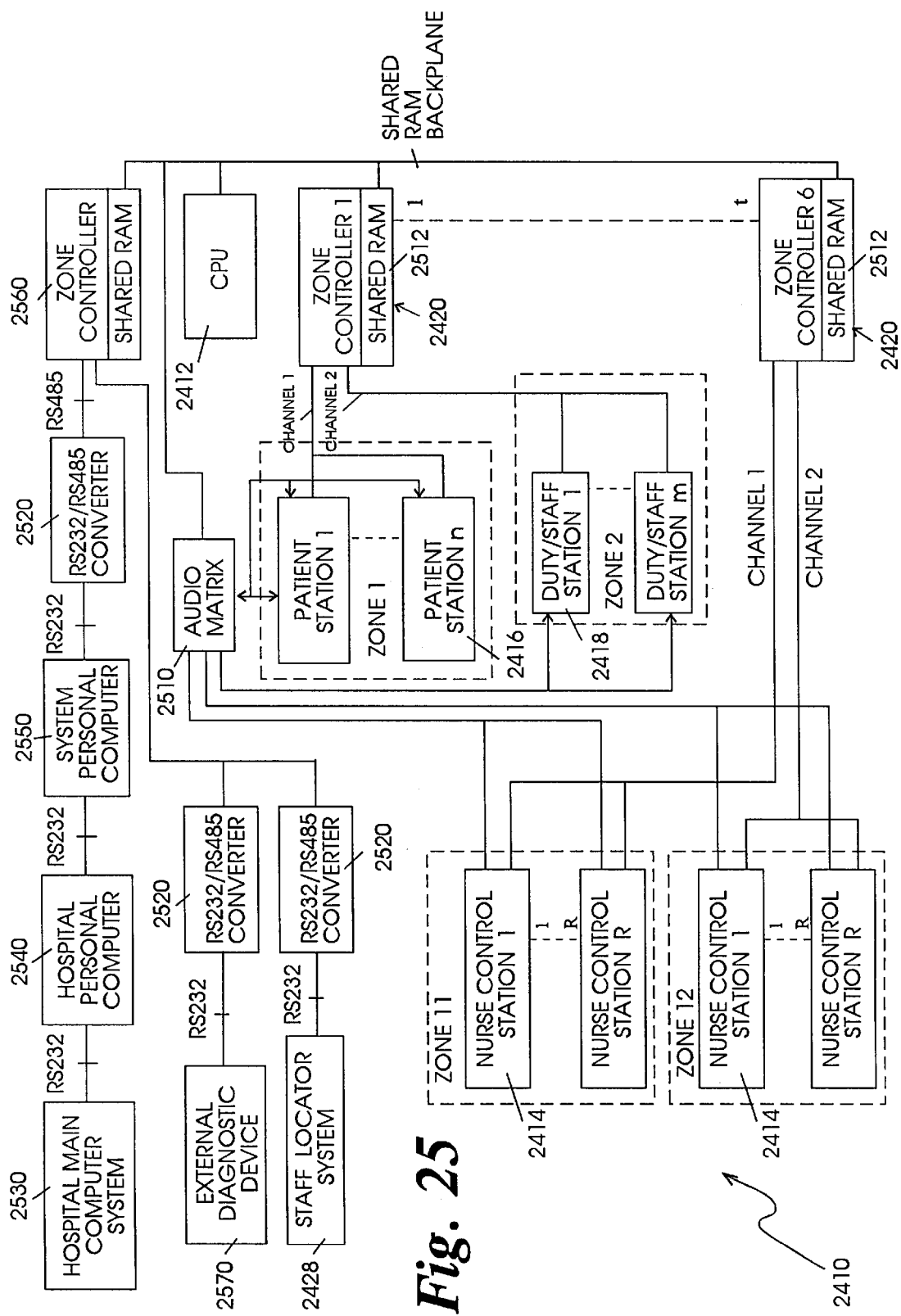
FIG. 25 is a functional block diagram of an alternative embodiment of a system configuration of the present invention.

FIG. 25 illustrates a functional block diagram of an alternative system configuration, which includes main hospital computer 2530 configured to interface with CPU 2412 to provide staff members with additional patient information, or to transfer from CPU 2412 to the main hospital computer patient information which may be utilized for billing purposes. For example, information pertaining to the types and quantities of prescription or intravenous drugs taken by the patient and the types of treatments received by the patient (e.g., X-rays or CT-scans), as well as the physician time spent with the patient, may be transferred to the main hospital computer to provide the hospital with more accurate billing information. Preferably, main hospital computer 2530 is interfaced with CPU 2412 via hospital personal computer 2540, system personal computer 2550, RS-232/RS-484 converter 2520 and zone controller 2560. In this configuration, the integrity of the main hospital computer is maintained and the serial conversion from RS-232 protocol to RS-484 protocol is accomplished.

Figure 28:
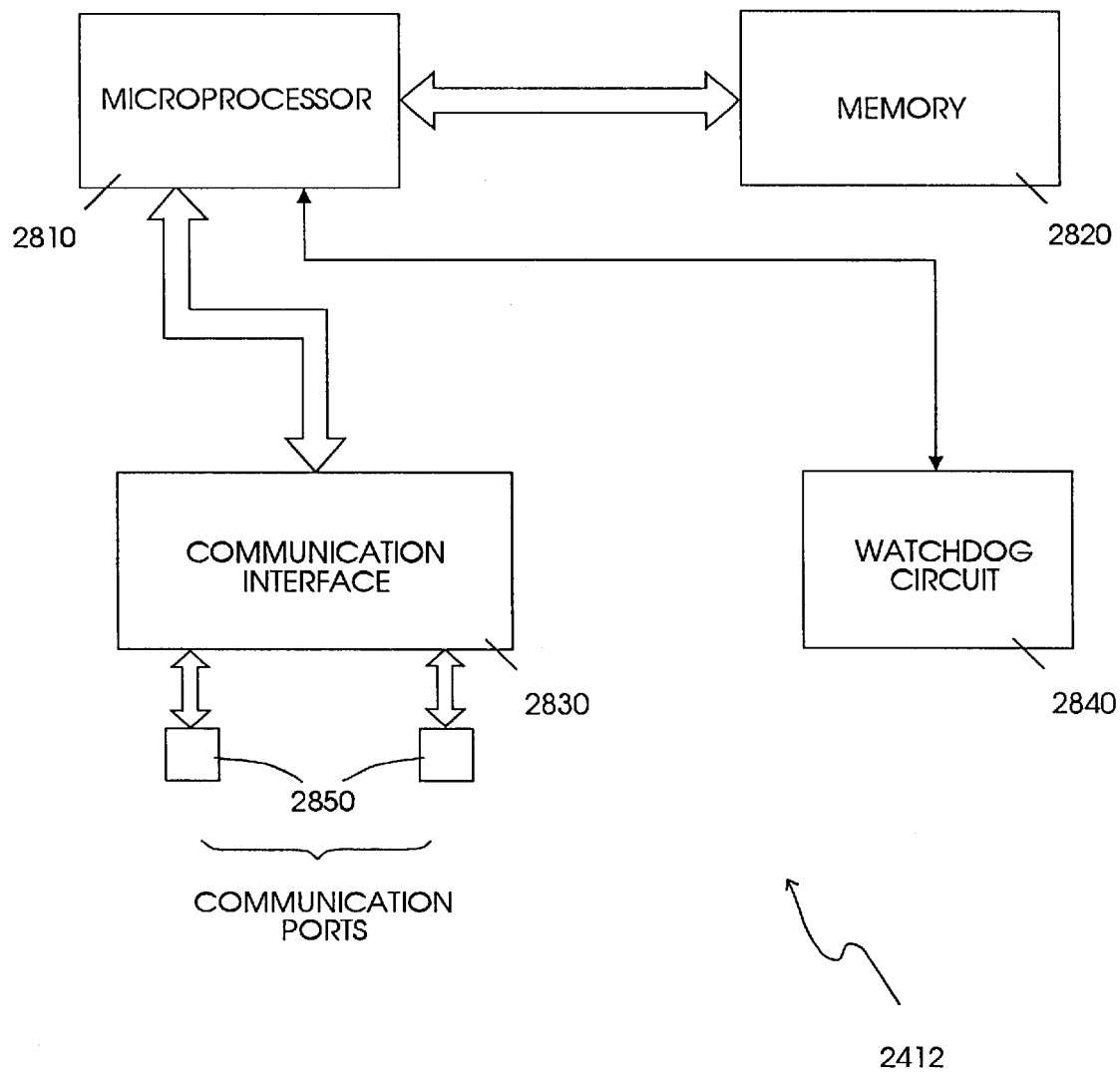
FIG. 28 is a circuit block diagram for the central processing unit illustrated in FIG. 24.

FIG. 28 illustrates the hardware components of central processing unit (CPU) 2412. The CPU 2412 includes microprocessor 2810, three Mbytes of memory 2820 (2 Mbytes of flash ROM and 1 Mbyte of RAM) having stored programs (e.g., operating system and application programs), and communication interface 2830. Preferably, microprocessor 2810 is an MC68000 16-bit microprocessor manufactured by Motorola Inc. In addition to the above circuits, CPU 2412 includes watchdog circuit 2840 which receives a one shot trigger from microprocessor 2810, at a predetermined time interval, preferably 300 msec., to ensure that the microprocessor is functioning. If, however, microprocessor 2810 fails to timely trigger watchdog circuit 2840, then the watchdog circuit will initiate an automatic reset of the microprocessor, thus preventing the microprocessor from locking-up for extended periods of time.

Communication interface 2830 and communication ports 2850 are provided to facilitate communication between CPU 2412 and zone controllers 2420 and between CPU 2412 and the external communication equipment. As noted above, the preferred communication protocol includes the RS-485 serial communication protocol. Accordingly, communication interface 2830 is configured to accommodate RS-485 communication utilizing RS-485 drivers/receivers which are known in the art.

Figure 29:
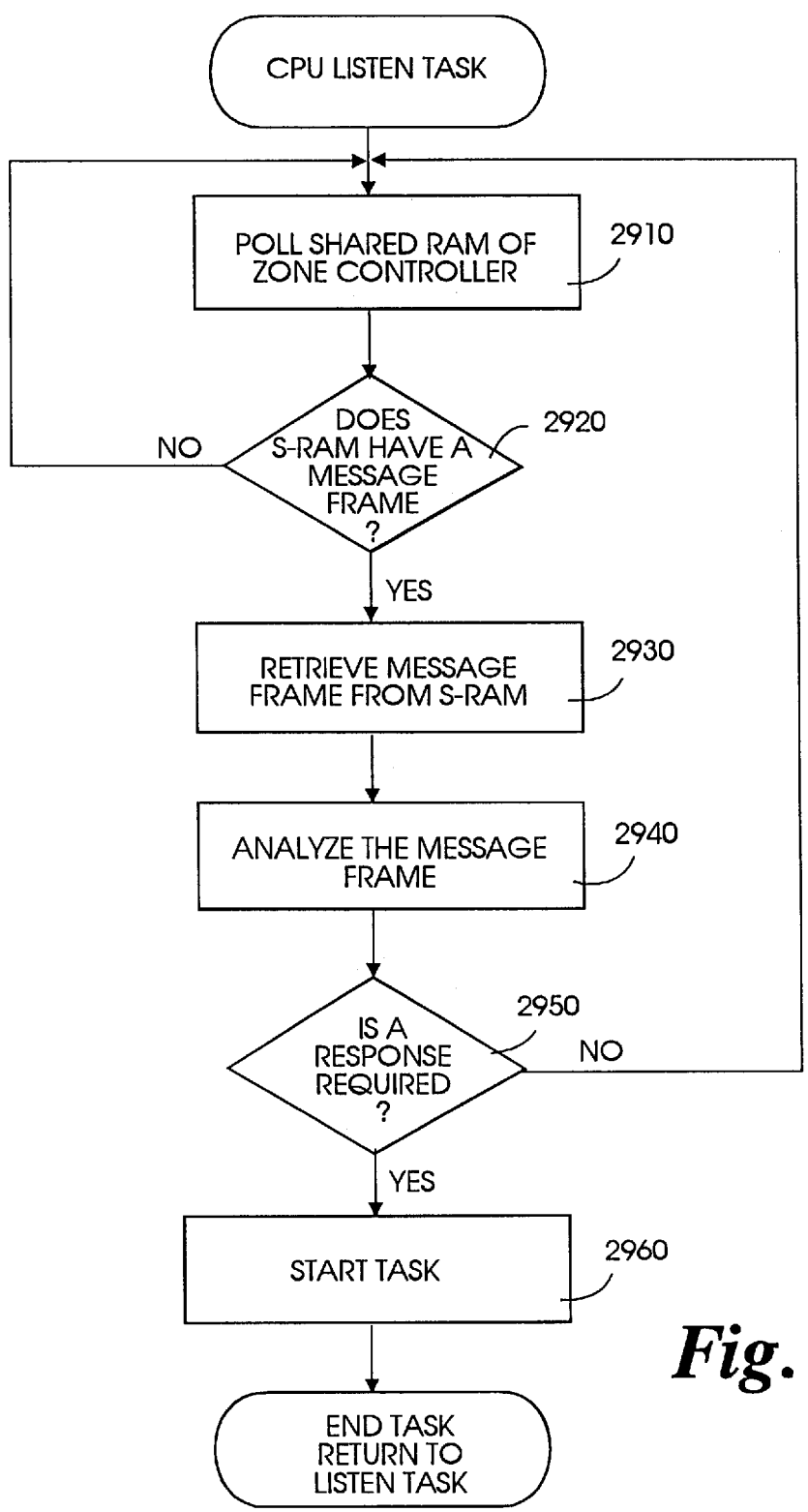
FIG. 29 is flow-chart diagram for the central processing unit illustrated in FIG. 24.

An exemplary operational flow of CPU 2412 is shown in FIG. 29. Initially, the CPU is in a listen mode. In the listen mode the CPU continuously polls or otherwise interrogates the different components attached thereto. For example, as shown in FIG. 29, the CPU will periodically poll each shared-RAM (S-RAM) 2512 (shown in FIG. 25) of each zone controller (step 2910) in a manner described hereinbelow. If the S-RAM does not have a message frame received from a station within the zone controller grouping, CPU 2412 returns and polls the next zone controller (step 2920). Preferably, as will be described in more detail below data transmitted between the CPU 2412 and the zone controller 2420 or between the zone controller 2420 and the stations (either 2414, 2416 or 2418) are in the form of message frames which include station identity information as well as the message data relating to a particular function.

If, however, the S-RAM does have a message frame stored therein, CPU 2412 will retrieve the message frame (step 2930) and analyze the received message frame by determining what patient station, staff station or nurse control station the message frame was received from and if the frame was received from a patient station, by organizing or obtaining any patient information associated with that particular patient station (step 2940). The DATA field within the INFORMATION field of the received message frame is then interpreted by the CPU, which determines whether a response to the associated patient station, staff station or nurse control station message frame is necessary (step 2950). If a response is not required, CPU 2412 returns to poll the next zone controller.

However, if a response is due, the CPU then starts the task associated with the information included in the message frame (step 2960). Upon completion of the task, CPU 2412 returns to the listen mode and begins polling the next zone controller connected thereto as described above.

The components of zone controller 2420 include a microcontroller, memory having stored programs (e.g., system or application programs) and a communication interface connected to communication ports. The connection of the zone controller 2420 components is the same as equivalent components of CPU 2412, as shown in FIG. 28. The zone controller 2420 also includes the shared-RAM (S-RAM) 2512, shown in FIG. 25, which is connected to the microcontroller. Preferably, the microcontroller is the 64180 microcontroller, manufactured by Motorola and the S-RAM includes 2 kilobytes of memory.

A communication interface and communication ports are provided to facilitate communication between zone controller 2420, CPU 2412 and slave devices, such as patient station 2416, staff station 2418 and/or nurse control station 2414. The communication protocol may be any known serial communication protocol, such as RS-232 or RS-485. The RS-485 protocol is preferred in the embodiment according to the present invention. Accordingly, the communication interface is configured to accommodate RS-485 communication utilizing RS-485 drivers/receivers which are known in the art. Each zone controller 2420 also includes a watchdog circuit which operates similarly to the watchdog circuit in CPU 2412. Thus, the watchdog circuit prevents the microcontroller from locking-up if the watchdog circuit is not polled at the predetermined time interval, preferably 300 msec., by the microcontroller.

The communication link between the zone controllers and stations or between the stations and peripheral equipment connected to the station is in a master-slave relationship. In the communication link between the zone controllers 2420 and the stations, the zone controllers are the master stations and the nurse control stations, patient stations or staff stations are the slave stations. Whereas, in the communication link between the stations and the peripheral equipment, the stations (e.g., the patient stations) are the master stations and the peripheral equipment is the slave. The master station is in control of the data link and transmits command frames to the slave stations. The master station maintains separate sessions (i.e., communication links) with each slave station attached to the link. To illustrate and again referring to FIG. 25, if zone controller 2420 is connected to a group of patient stations (1 to n) and/or connected to a group of staff stations (1 to n), the zone controller (master) will periodically poll each patient station (slave) to retrieve message frames. The slave station responds to the commands from the master station and can send one message to the master station per poll from the master station.

The master station may communicate with the slave stations in one of two logical states. One state is the INITIALIZATION state which is used to initialize the master/slave station (e.g., identify for each communication link which device connected thereto is the master and which is the slave). A second state is the INFORMATION TRANSFER state which permits the master and slave stations to transmit and receive control or application information transmitted across the data link between the master station and the slave stations in the form of message frames or blocks of data.

In the preferred embodiment, the message frames may be one of three types. The first type of message frame is the INFORMATION FORMAT frame (I-frame) which is used to transmit application information (e.g., message information associated with a particular function or station status data) between the master and slave stations. The I-frame may also acknowledge receipt of a frame from a transmitting station. The second type of message frame is the SUPERVISORY FORMAT frame (S-frame) which performs control functions, such as acknowledging the receipt of a poll from the master station or requesting the temporary suspension of the transmission of I-frames. The third type of message frame is the UNNUMBERED FORMAT frame (U-frame) which is also used for control purposes, such as performing data link initialization or tests.

As noted, the data (or information) transmitted between master and slave stations is preferably configured in the form of a message frame. The preferred message frame includes five fields, similar to the frame shown below:

ADDRESS/LENGTH/CONTROL/INFORMATION/FCS

Where, the ADDRESS field is one byte in length and identifies the patient station involved in the particular frame transaction (each station has a unique address which allows the CPU and zone controller to identify which station sent the frame); the LENGTH field is one byte in length and contains the size of the frame, in bytes, excluding the address and length fields; the CONTROL field includes the command and response information used to maintain dataflow accountability of the communication link between the zone controller (master) and the patient station (slave); and the INFORMATION field retains a predetermined number of bytes of data, preferably between 1 and 145 bytes, relating to the application data, such as, the data associated with the activation of the nurse call button (hereinafter "the nurse call data"). The frame-check-sequence (FCS) field, typically one byte in length, is used to check for transmission errors between the master and slave stations or devices.

The system of the present invention may transmit a predetermined number of message frames, preferably between 1 and 8 frames, before an acknowledgement or response to a transmitted frame is received. As a result, the CONTROL field is utilized to maintain data-flow accountability of the communication link, as noted above.

Shown in table III below is the CONTROL field bit encoding for the master and slave stations.

TABLE III

CONTROL field bit encoding (master station):

I-frame format:
:7:6:5:4:3:2:1:0:
: x x : x x : 0
: : : : : : : :-> Normally set to binary 0
: : : : : : : :
: : : : :-:-:----> N(S)
: : : :
: :-:-:---------> N(R)
:
:---------------> P CONTROL field bit encoding (slave station):

I-frame format:
:7:6:5:4:3:2:1:0:
: x x : x x : 0
: : : : : : : :-> Normally set to binary 0
: : : : : : : :
: : : : :-:-:----> N(S)
: : : :
: :-:-:---------> N(R)
:
:---------------> F The send sequence number N(S) (bits 1, 2 and 3) indicates the sequence number associated with a transmitted frame. Basically, the sequence number is a message counter which counts the number of message frames sent to a receiving station. The receive sequence number N(R) (bits 1, 2 and 3) indicates the next sequence number that is expected at the receiving station. The receive sequence number may also serve as an acknowledgement of the previous frame. In addition, the transmitting station maintains a send state variable V(S) which is the sequence number of the next message frame to be transmitted, and the receiving station maintains a receive state variable V(R), which contains the number that is expected to be in the sequence number of the next frame. The send state variable is incremented with each message frame transmitted and placed in the send sequence number N(s) field in the frame.

Upon receiving a frame, a receiving station checks for a transmission error by comparing the send sequence number with the receive state variable. If the frame is acceptable (i.e., the send sequence number and the receive state variable are equal), the receiving station increments the receive state variable V(R) and interpolates the variable into the receive sequence number field N(R) in the next outbound message frame. If, on the other hand, the send state variable V(S) does not match the receive sequence number N(R) in the message frame, the receiving station decrements the send state variable V(S) and retransmits the last message frame when the next frame has to be transmitted.

To establish an interactive communication link between stations, the master station uses the poll bit (P) to solicit a status response (e.g., an S-frame) or an I-frame from a slave station. Generally, the slave station does not transmit a frame to a master station until a message frame with an active poll bit (i.e., P is set to logic 1) is received from the master frame. In the preferred embodiment, the polling rate of the master station is aperiodic or not fixed. The polling rate is dependent upon a number of factors such as the baud rate and the type of message frame being sent by the slave station. For example, if the baud rate is 9600 and if all the slave stations respond to a poll by the master station with an S-frame, the polling rate is approximately 20 msec. However, if a slave station responds with an I-frame which includes 64 bytes of display data the rate (or time) before the master station will poll the next slave station is approximately 64 msec. Generally, at 9600 baud, one byte of data is transferred in one millisecond.

The slave station responds to an active poll bit with an I-frame or S-frame format message frame. In the preferred embodiment, the slave station has 15 msec. to start transmitting the responding message frame and 150 msec. to complete transmission of the frame which is identified by activating the Final bit (F) (i.e., F is set to a logic 1).

If the slave station fails to successfully respond to the polling frame of the master station with either an S-frame or I-frame, for a predetermined number of polls, preferably 10, that particular station will be marked as disconnected and will be polled at slower rate (preferably, about every 10 sec.) until the master station receives at least one message frame from that particular slave station. When a station or other equipment connected to the system of the present invention are determined to be disconnected, the identity of the station or other equipment and the room location of the equipment are stored in a problem report which can be printed on hard or soft copy via printer 2724 and/or external computer 2722, shown in FIG. 27. Alternatively, the problem report can be displayed on nurse control station display 3272 shown in FIG. 32 upon the proper keying of direct select keys 3374 of nurse control station display 3272 pursuant to menu prompts.

Referring now to Table IV below, the CONTROL field encoding for the commands and responses used by an S-frame are shown:

TABLE IV

CONTROL field bit encoding (master station):

S-frame format:
:7:6:5:4:3:2:1:0:
: x x : : : 0 1
: : : : : : : :-> Normally set to binary 1
: : : : : : : :
: : : : :-:-----> Commands:
: : : : :-:----->     Binary 0 - Receive Ready (RR)
: : : : :-:----->     Binary 1 - Receive Not Ready (RNR)
: : : :
: :-:-:---------> N(R)
:
:---------------> Poll bit (P)

CONTROL field bit encoding (slave station):

S-format:
:7:6:5:4:3:2:1:0:
: : : : : : 0 1
: : : : : : : :-> Normally set to binary 1
: : : : : : : :
: : : : :-:-----> Commands:
: : : : :-:----->     Binary 0 - Receive Ready (RR)
: : : : :-:----->     Binary 1 - Receive Not Ready (RNR)
: : : :
: :-:-:---------> N(R)
:
:---------------> Final bit (F)

The receive ready (RR) command is used by either the master or the slave station to indicate that it is ready to receive an I-frame and/or acknowledge previously received frames by using the receive sequence number. If a station had previously indicated that it was busy by using the receive not ready (RNR) command, the station then uses the RR command to indicate that it is now free to receive data (e.g., an I-frame).

As noted, receive not ready (RNR) is used by a receiving station to indicate a busy condition in response to polling by a master station. This notifies the transmitting station that the receiving station is unable to accept I-frames. The RNR command may also be utilized to acknowledge a previously transmitted frame by using the receive sequence number.

The commands and responses used by a U-frame are shown below in Table V:

TABLE V

CONTROL field encoding (master station)

```
U-frame format:
:7:6:5:4:3:2:1:0:
 : : : : : : 1 1
 : : : : : : :-:-> Normally set to binary 3
 : : : : : : : :
 : :-:-:-:-:-----> Commands:
 : :-:-:-:-:----->   0 - Set Init. Mode (SIM)
 : :-:-:-:-:----->   1 - Reset Init. Mode (RIM)
 : :-:-:-:-:----->   2 - Test Message (TM)
 : :-:-:-:-:----->   3 - Loop Back (LB)
 : :-:-:-:-:----->   4 - Broadcast (BC)
 :
 :---------------> Poll bit (P)
```

CONTROL field encoding (slave station)

```
U-format:
:7:6:5:4:3:2:1:0:
 1 : : : : : 1 1
 : : : : : : :-:-> Normally set to binary 3
 : : : : : : : :
 : :-:-:-:-:-----> Commands:
 : :-:-:-:-:----->   0 - Set Init. Mode (SIM)
 : :-:-:-:-:----->   1 - Reset Init. Mode (RIM)
 : :-:-:-:-:----->   2 - Test Message (TM)
 : :-:-:-:-:----->   3 - Loop Back (LB)
 :
 :---------------> Final bit (F)
```

The set initialization mode (SIM) is used by a master or slave station to initialize the master/slave session (or communication link). The SIM command puts the master and slave stations in the initialization state. Upon receiving the SIM command, the receiving station clears the send state variable number V(S) and the receive state variable V(R), thus clearing a retransmit buffer (not shown). The SIM command is used by a station on power-up or to clear a lock-up condition of the station. The reset initialization mode (RIM) is used by a master or slave station to set an information transfer state. This command also serves as an acknowledgement of the SIM command.

The test message (TM) command is used to test data lines. The receiving station responds with a LB command which carries (or echoes back) the same data received from the message frame where the TM command was active. Failure of a slave station to echo back the same data received in the message frame causes the master station to identify the station as disconnected and the station identity and location are added to the problem report.

The broadcast (BC) command (bits 2–6) is used by a master station to transmit data to all slave stations. The master station sends this command while the P bit is set to a logic zero and the address field of the message frame, noted above, contains "FF" hex.

The bit encoding for the INFORMATION field of the message frame noted above will now be described.

Preferably, the INFORMATION field consists of four fields which identify the priority level of the message frame, the station ID, the type of message and data to augment the message type:

PATH/RSP_ID:REQ_ID/DATA/O

The PATH field, shown below in Table VI, may be four bytes in length and contains routing information and frame transition priority data. The transition priority data identifies to the CPU the priority level associated with the received I-frame. As a result, the system of the present invention can prioritize incoming message frames so as to organize staff responses thereto in order of priority, as will be described in more detail below. The last byte of this field preferably includes an address expansion bit which when set to logic one identifies that the next byte of data is the station address field which identifies which slave station is sending the message frame.

TABLE VI

PATH field bit encoding:

```
:7:6:5:4:3:2:1:0:
 : : : : : : : :
 : : : :-:-:-:-:-> Station Address
 : : :
 : :-:-----------> Priority: binary 2 - alarm,
                            binary 1 - event/control,
 : :-:----------->          binary 0 - data type
 :
 :---------------> Address expansion set to logic 1 = next byte
                                                     is station
                                                     address
```

The RSP_ID:REQ_ID field, shown below in Table VII, contains response/request tag (ID) data. Upon receiving a request message (type bit is set to logic 1), the slave station sends a specific response message (e.g., an I-frame). If there is no specific response, the slave station sends generic acknowledgement typically in the form of an S-frame.

TABLE VII

RSP_ID:REQ_ID field bit encoding:

```
:7:6:5:4:3:2:1:0:
 : : : : : : : :
 : : : :-:-:-:-:-> response/request ID
 : :
 : :-------------> local master: binary 1 = local master
                                             request/response
 :
 :---------------> type: logic 1 = request, logic 0 = response
```

Generally, the DATA field may be 128 bytes in length and contain application specific data and preferably, consists of three fields:

LENGTH/DTYPE/TEXT

Where, the LENGTH field, typically 1 byte in length, contains the size in bytes of the DTYPE and TEXT fields; the DTYPE field, typically one byte in length, contains data codes such as the type of message being sent, e.g., code blue; and the TEXT field which may be 126 bytes in length, contains application specific data, e.g., message data associated with a particular function or station status data, which is utilized to augment the DTYPE field by identifying a textual message associated with the particular function identified in the DTYPE field. For example, if the DTYPE field identifies a "code blue" code, the TEXT field will include the text which should be displayed on other stations, such as the staff station.

Figure 30:
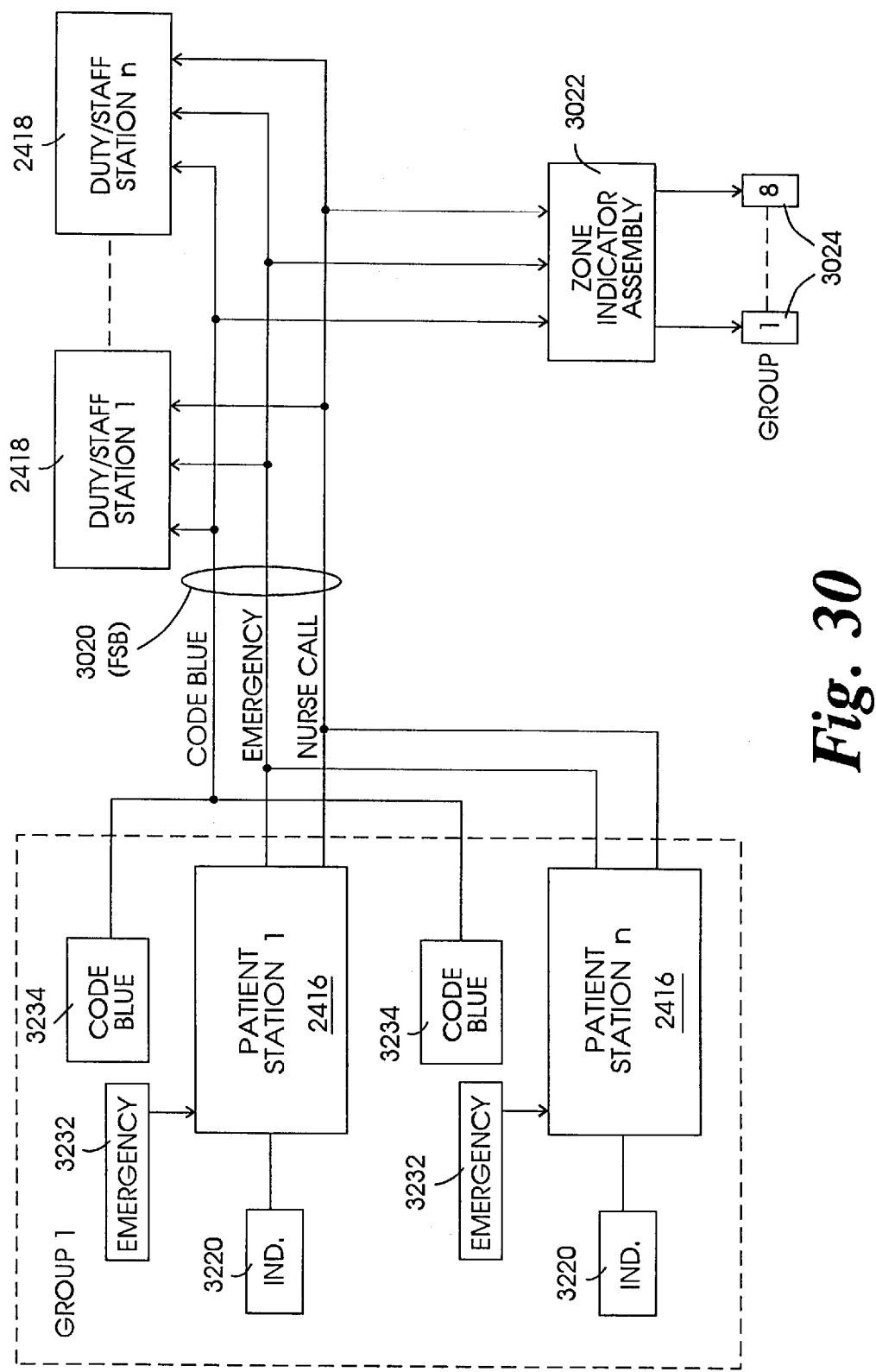
FIG. 30 is a block diagram for the fail safe feature associated with the system of the present invention.

In the event of a failure within the CPU 2412, the system of the present invention also provides a fail safe feature which is activated upon detection by the nurse control stations 2414, the patient stations 2416 and/or staff stations 2418. An exemplary embodiment of the configuration for fail safe operation is shown in FIG. 30. In this configuration, fail safe bus (FSB) 3020 is connected between each patient station 2416, each corresponding staff station 2418 and zone indicator assembly 3022. If a failure occurs in the CPU 2412, each patient station 2416 and corresponding staff station 2418 will fail to receive a polling signal from their corresponding zone controllers. As a result, each station will operate in a local mode utilizing the fail safe bus. When in the local mode, activation of any of the functions which have access to the fail safe bus will cause a response at a particular patient station, the staff stations and at the zone indicator assembly connected to the group, to allow staff members in the vicinity of the station utilizing the fail safe bus to respond.

Figure 31:
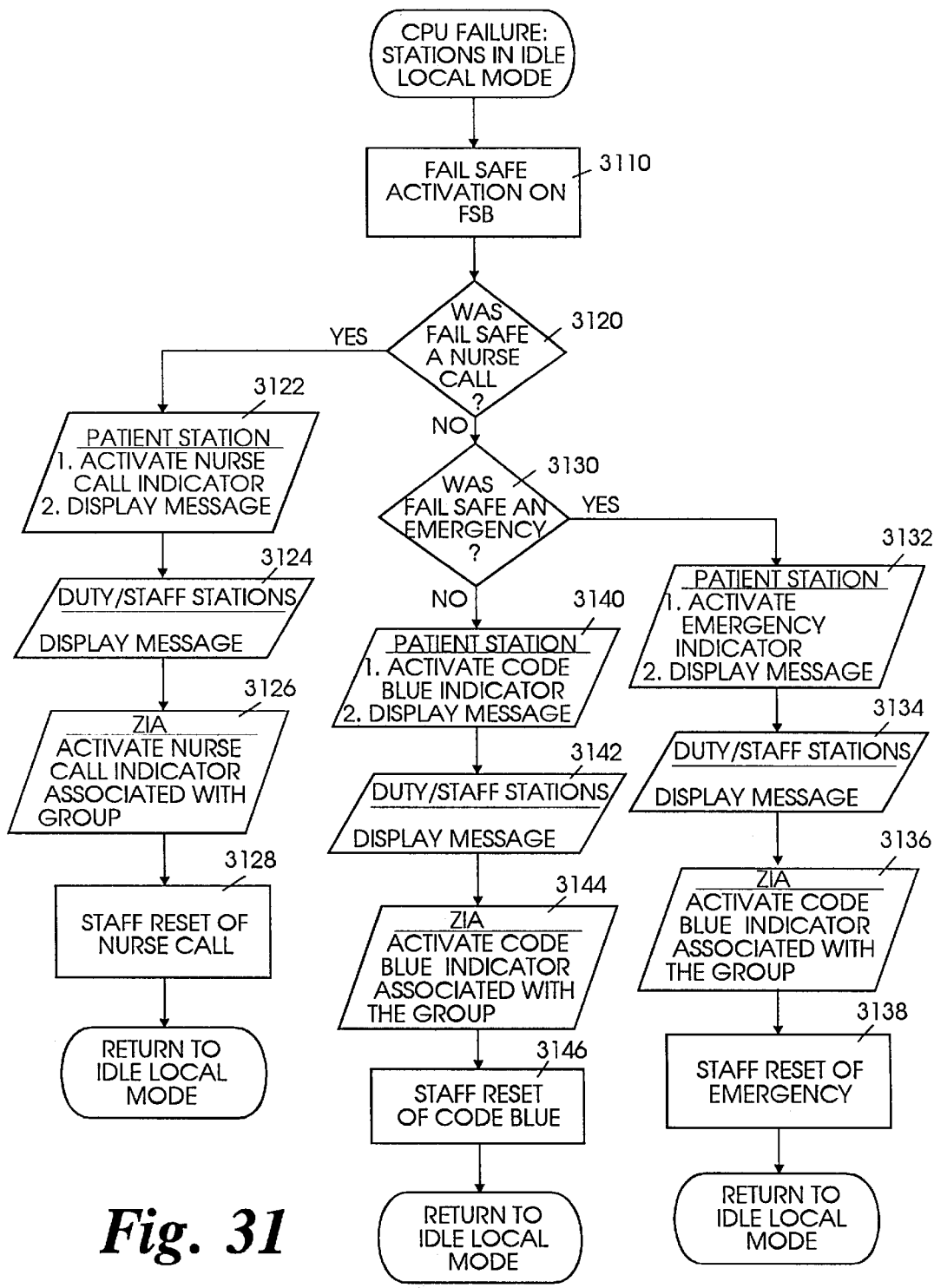
FIG. 31 is a flow-chart diagram of the fail safe feature illustrated in FIG. 31.

An operational flow associated with the above described exemplary fail safe feature will be described with reference to FIGS. 30–32. As noted, upon failure of the CPU 2412, the stations associated with the system of the present invention operate in the local mode. In response to activation of a fail safe device (e.g., the nurse call button 3250, the code blue switch 3234 or the emergency switch 3232) the system first determines whether the cause of the fail safe was from the activation of nurse call button 3250 of patient control unit 3210 (shown in FIG. 32) (steps 3110 and 3120). Nurse call button 3250, code blue switch 3234 and/or emergency switch 3232 are connected to patient station 2416 and provide either a general indication to staff members that the patient needs assistance or an emergency indication relating to the patients immediate health condition. Nurse call button 3250 allows the patient to indicate the need for general assistance, whereas, code blue switch 3234 and emergency switch 3232 allow staff members to activate the appropriate staff response to the patient's health condition. For example, if the patient is experiencing a heart attack a staff member would activate the code blue switch.

If the cause of the fail safe was due to the activation of nurse call button 3250, the patient station responds by activating nurse call indicator 3222 of indicator assembly 3220 associated with that particular patient station and by displaying a "nurse call" message on patient station display 3230 (step 3122). Next, the staff stations 2418 (shown in FIG. 24) associated with the group of patient stations 2416 respond by displaying a "nurse call" message on staff station display 2422 (step 3124). Zone indicator assembly (ZIA) 3022 activates the nurse call indicator of zone indicator 3024 (e.g., indicators 1 through 8, shown in FIG. 30) associated with the particular group of patient stations (step 3126). For example, if the nurse call button is activated by a patient station associated with group 1, the nurse call indicator of the group 1 zone indicator 3024 associated with zone indicator assembly 3022 will be activated. Manual reset of the patient station by a staff member responding to the call returns the FSB and the patient stations to the idle local mode (step 3128).

If the cause of the fail safe was not from the activation of the nurse call button, the fail safe system then determines if the fail safe was caused by the activation of emergency switch 3232 (step 3130). If fail safe operation was caused by the activation of emergency switch 3232, patient station 2416 responds by activating the emergency indicator associated with that patient station and by displaying an "emergency" message on patient station display 3230 (step 3132). Preferably, the emergency indicator is the same indicator as nurse call indicator 3222. However, activation of indicator 3222 in the emergency mode results in a blink light at a predetermined rate in pulses per minutes (PPM) as illustrated in the table of FIG. 42. Whereas, activation of indicator 3222 in the nurse call mode results in a steady lamp intensity. Second, staff station or stations 2418 associated with the subject patient station, displays an "emergency" message on staff station display 2422, shown in FIG. 24 (step 3134). Next, zone indicator assembly 3022 activates the emergency indicator of zone indicator 3024 associated with the group with which the particular patient station belongs (step 3136). Staff members responding to the emergency call, manually reset emergency switch 3232 (step 3138), thus returning the fail safe system to the idle local mode.

If, on the other hand, the cause of the fail safe was not from the activation of an emergency switch, then, according to this exemplary embodiment, the fail safe operation was activated by code blue switch 3234. The patient station responds to the code blue call by activating code blue indicator 3228 associated with patient station 2416 to which the code blue switch is operatively connected, and by displaying a "code blue" message on patient station display 3230 (step 3140). Secondly, staff station or stations 2418 associated with the group of patient stations 2416, displays a "code blue" message on station display 2422 (step 3142). Zone indicator assembly 3022 also activates the code blue indicator associated with the subject patient station group number (step 3144). Manual reset of code blue switch 3234 by the responding staff members returns the fail safe bus to the idle local mode (step 3146).

Nurse Control Station

The nurse control portion of the present invention will now be described with reference to FIGS. 32 and 33. FIG. 32 illustrates a system configuration in which peripheral equipment is connected to patient station 2416 and in which nurse control station 2414 includes main processor 3270, keyboard 3236 and nurse control station display 3272. Nurse control station display 3272 can be user programmed to perform functions, such as initiating a code blue operational sequence, either through keyboard 3236 or direct select keys 3274. The direct select keys 3274 allow staff members to select specific functions in response to menu driven prompts.

Figure 33:
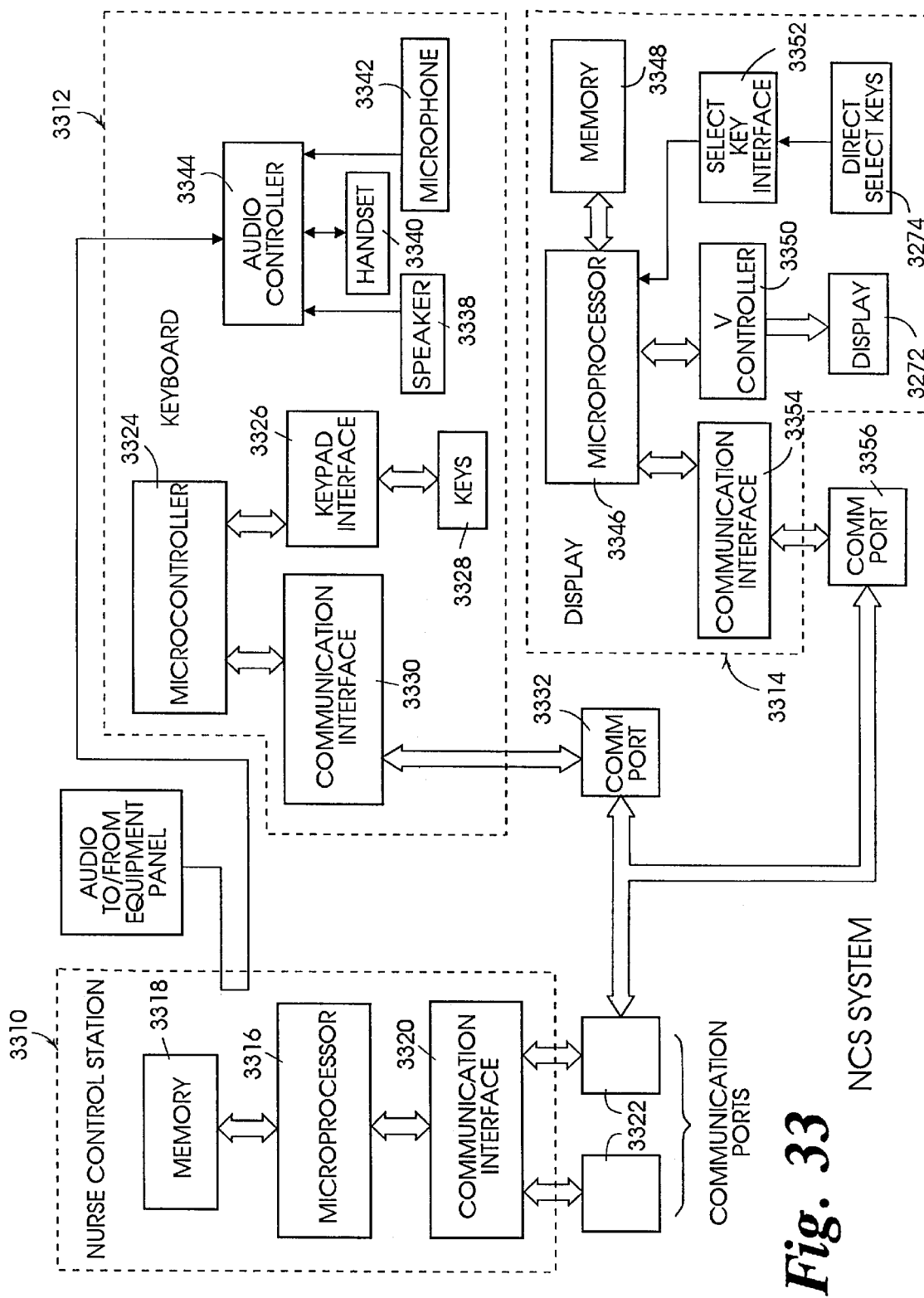
FIG. 33 is a block diagram for the nurse control station illustrated in FIG. 24.

FIG. 33 is a block diagram which illustrates hardware components for nurse control station 2414. Nurse control station 2414 includes main processor circuitry 3310, keyboard circuitry 3312 and display circuitry 3314. Main processor circuitry 3310 includes microprocessor 3316, such as the 16 bit model 286 microprocessor manufactured by Chips & Technology, Inc., 2 Mbytes of memory 3318 having stored programs (e.g., system and application programs) and communication interface 3320 connected to communication ports 3322.

Preferably, communication interface 3320 and communication ports 3322 are provided to facilitate data communication between zone controller 2420, CPU 2412 and the nurse control station 2414. As noted above, the preferred communication protocol includes the RS-485 serial communication protocol. Accordingly, communication interface 3320 is configured to accommodate RS-485 communication utilizing RS-485 drivers/receivers which are known in the art.

Keyboard circuitry 3312 includes microcontroller 3324, such as model 8052 manufactured by Intel, which includes internal memory having, preferably, 4 Kbytes of ROM and 256 bytes of RAM, keypad interface 3326 which is connected to keys 3328 and facilitates communication between a staff member and the nurse control station. Communication interface 3330 and communication port 3332 are provided as a data communication link to main processor circuitry 3310. As noted, the preferred communication protocol includes the RS-485 serial communication protocol. Accordingly, communication interface 3330 is configured to accommodate RS-485 communication utilizing RS-485 drivers/receivers which are known in the art.

Figure 34:
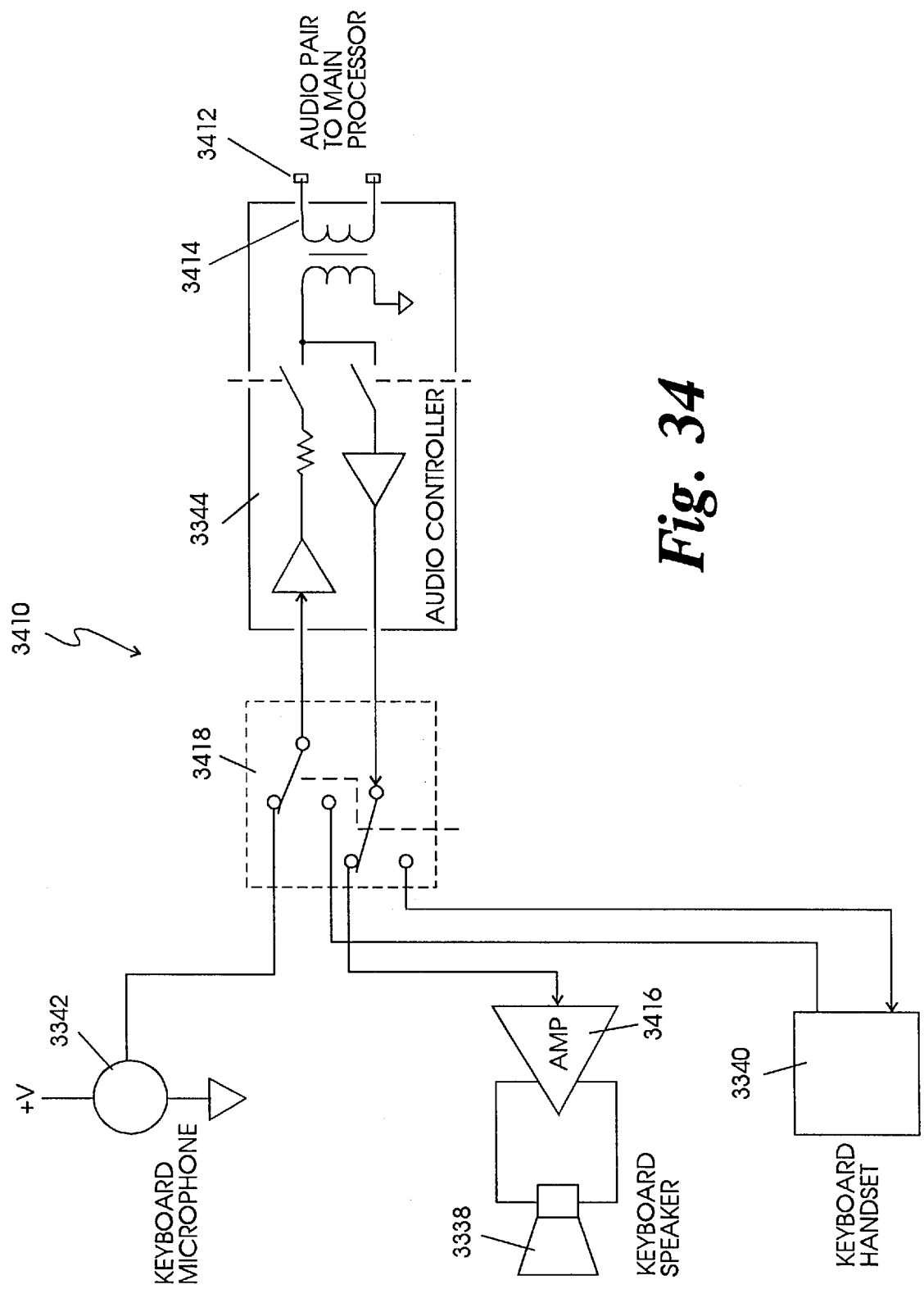
FIG. 34 is a circuit block diagram for the audio circuitry of the keyboard of the nurse control station illustrated in FIG. 24.

Keyboard 3236 (shown in FIG. 32) includes speaker 3338, handset 3340 and microphone 3342 which facilitate audio communication between nurse control station 2414, patient stations 2416 and/or staff stations 2418, via audio controller 3344. The audio circuit portion 3410 of nurse control station 2414 will now be described with reference to FIG. 34, which illustrates the hardware configuration for the audio portion of the keyboard. As shown, audio pair 3412 from main processor 3270 of nurse control station 2414 (shown in FIG. 32) is connected to the front end of audio controller 3344. Preferably, the front end of audio controller 3344 includes a coupled 600 ohm balanced transformer 3414 which isolates the internal audio circuitry of nurse control station 2414 from the external audio circuits. Depending upon whether the audio signal is being received or transmitted, the back end of audio controller 3344 either directs the audio signal to keyboard speaker 3338 or to handset 3340, or directs the audio signal from microphone 3342 to transformer 3414.

Preferably, audio controller 3344 is a 34118 audio controller manufactured by Motorola. Audio input signals from main processor 3270 of nurse control station 2414, which pass through the audio controller are directed to keyboard speaker 3338 via amplifier 3416 or to handset 3340 via relay controller 3418 controlled by microcontroller 3324 (shown in FIG. 33). Audio generated by the nurse control station via microphone 3342 or handset 3340 is transferred through relay controller 3418 to audio controller 3344 and onto the audio pair as shown. The audio pair from keyboard circuitry 3312 is directed to the equipment panel via main processor circuitry 3310, as shown in FIG. 33.

Display circuitry 3314 includes microprocessor 3346, such as model 8051 manufactured by Intel, memory 3348 having stored programs (e.g., system and application programs), video controller 3350 which is connected to nurse control station display 3272 and facilitates the display of the visual communication signals. Select key interface 3352 is connected to direct select keys 3274 and is provided to identify to microprocessor 3346 which direct select key 3274 has been depressed. Communication interface 3354 and communication port 3356 are provided as a data communication link to main processor circuitry 3310. As noted, the preferred communication protocol includes the RS-485 serial communication protocol. Accordingly, communication interface 3354 is configured to accommodate RS-485 communication utilizing RS-485 drivers/receivers which are known in the art.

Patient Station

The patient station portion of the present invention will now be described with reference to FIGS. 27, 32 and 35–37. Turning initially to FIG. 32, patient station 2416 is a microprocessor controlled interface between CPU 2412, the patient bedside equipment and peripheral equipment. The communication link between CPU 2412 and the bedside or peripheral equipment is via the master/slave communication link described above. Examples of the patient bedside equipment include heart monitors, respirators, pulse oxymeters or I.V. pumps which include data communication ports to serially transmit data. Examples of peripheral equipment include patient control unit 3210, staff presence switch 3254, indicator assembly 3220, code blue switch 3234, emergency code switch 3232 and/or a smoke detector (not shown). Staff presence switch 3254 is preferably located by the door of the patient rooms and is provided to activate indicator 3220 and to cause patient station 2416 to send a message frame to CPU 2412 indicating the particular type of staff member who is present in the patient's room, as will be described in more detail below. In addition, patient station 2416 may be operatively connected to a side-rail communication system (not shown) installed in a side-rail of the patient's bed, as well as bed sensors which sense whether the patient is in the bed. Side-rail communication system may be connected to the audio output ports 3624, shown in FIG. 36, to facilitate audio communication at the side-rail.

Figure 35:
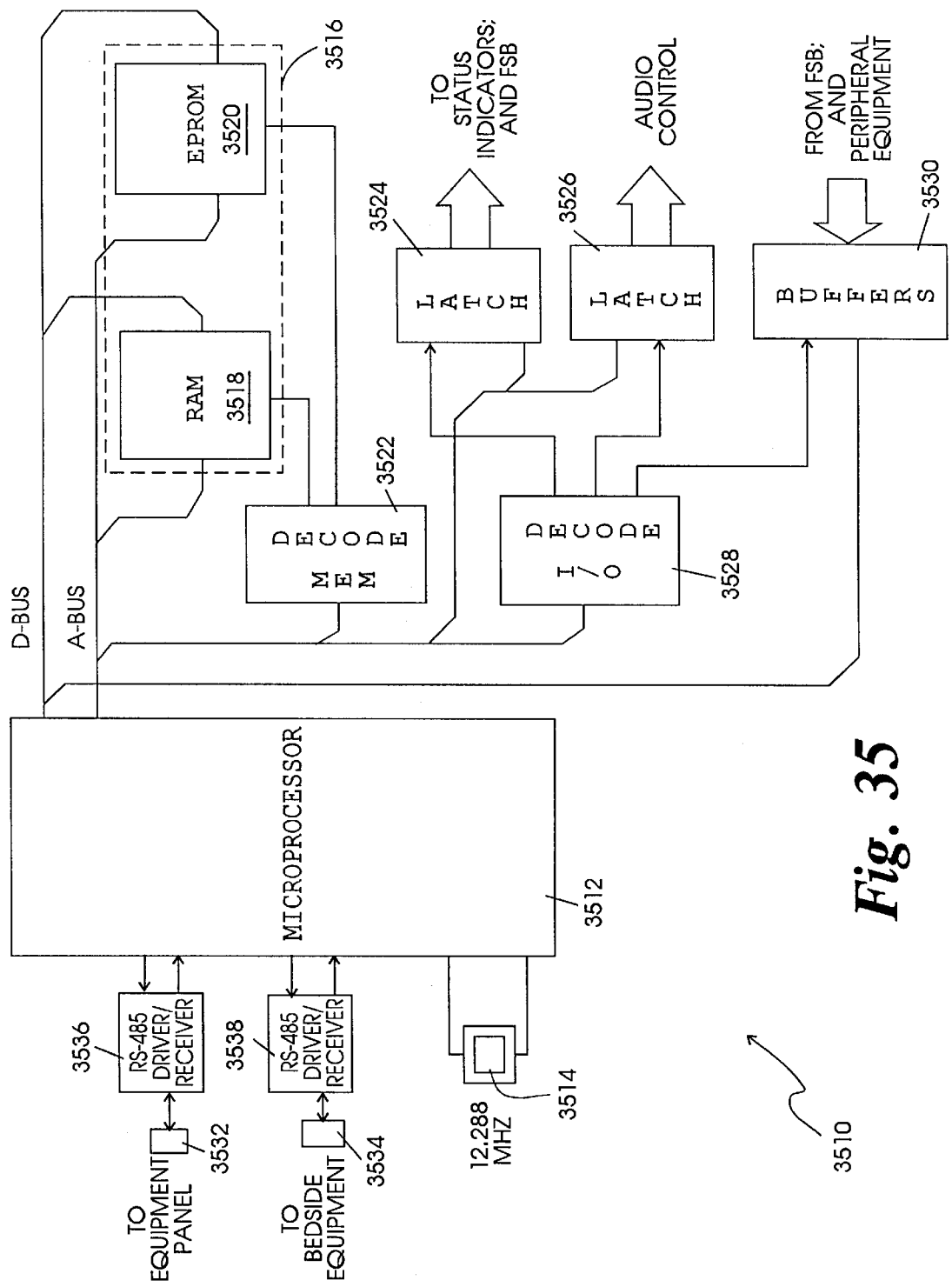
FIGS. 35 and 36 are circuit block diagrams for the internal circuitry for the patient stations illustrated in FIG. 24.

FIG. 35 is a circuit block diagram for the patient station circuitry 3510 installed within patient station 2416. The patient station circuitry 3510 includes microprocessor 3512, such as model 64180 manufactured by Motorola operating at a frequency of 12.888 MHz. via crystal 3514, 96 Kbytes of memory 3516 (e.g., 64 Kbytes of flash ROM and 32 Kbytes of RAM) having stored programs, e.g., system and application programs. In this exemplary configuration, the data and address buses of the microprocessor are connected to memory, e.g., RAM 3518 and an EPROM 3520. Memory decoder 3522 is utilized to select between RAM 3518 and EPROM 3520 in response to a particular address on the address bus. The address bus is also connected to a pair of latches 3524 and 3526 which interface the microprocessor to status indicators, the fail safe bus (FSB), the audio control circuitry, and to switches and other peripheral equipment connected to the patient station, as shown. In addition, I/O decoder 3528 is utilized to select between either latch in response to a particular address on the address bus. Incoming signals from the above noted peripheral equipment are received by buffer 3530 and then transferred to the data-bus upon being enabled by I/O decoder 3528.

Utilizing the preferred microprocessor 3512 (i.e., the Motorola 64180), serial communication between the zone controller 2420 and microprocessor 3512 or between the bedside equipment and microprocessor 3512, may be accomplished through either one of two asynchronous serial communication ports 3532 and 3534 which are, preferably, configured to RS-485 protocol utilizing RS-485 driver/ receivers (RS-485 D/R) 3536 and 3538 as shown.

Figure 36:
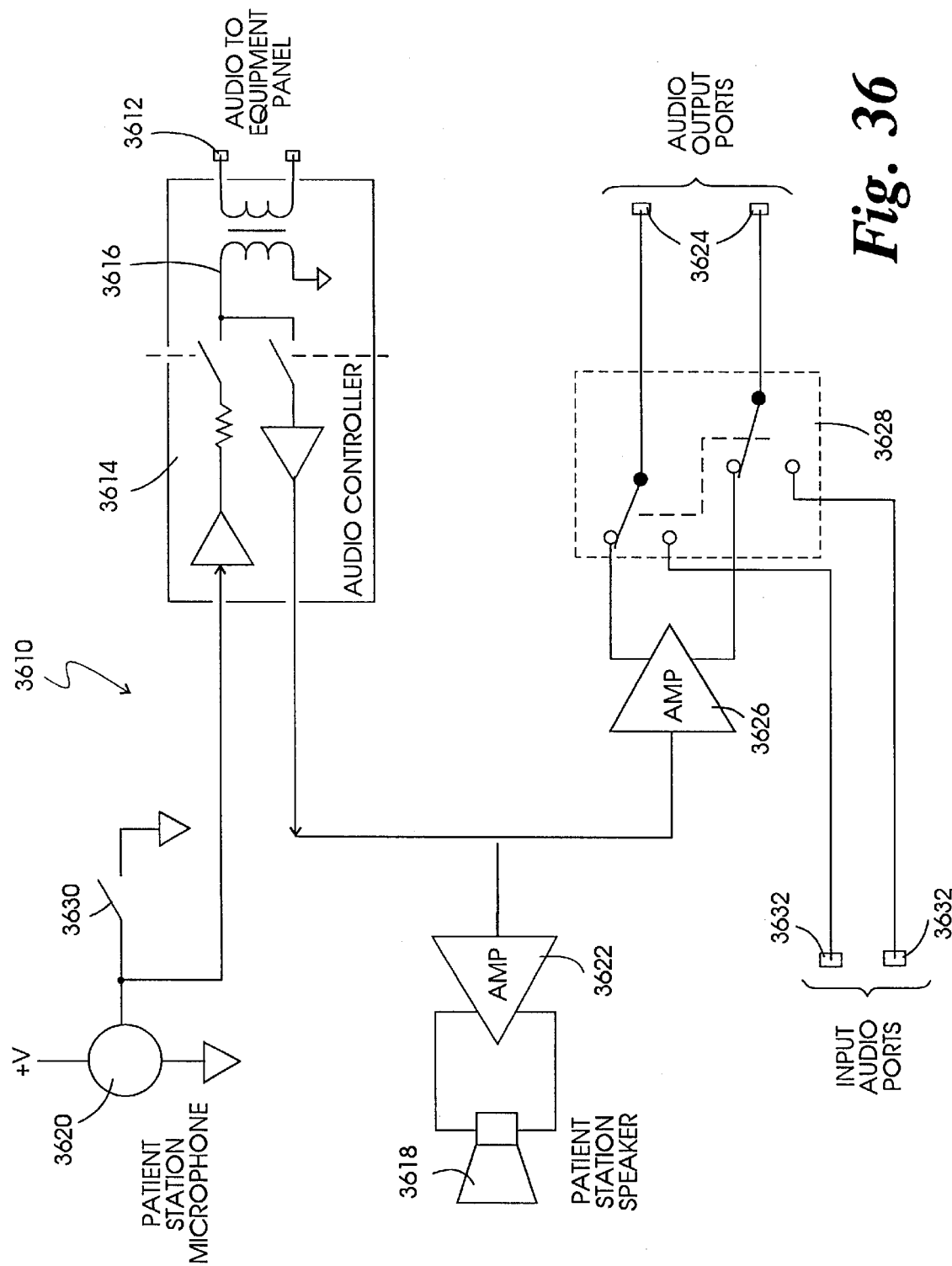

FIG. 36 is a circuit block diagram for the audio portion 3610 of patient station 2416. As shown, audio pair 3612 from an equipment panel (e.g., audio matrix 2510 shown in FIG. 25) is connected to the front end of audio controller 3614. Preferably, the front end of audio controller 3614 includes a coupled 600 ohm balanced transformer 3616 which isolates the internal audio circuitry of patient station 2416 from the external audio circuits. Depending upon whether the audio signal is being received or transmitted, the back end of audio controller 3614 either directs the audio signal to patient station speaker 3618 or to an external audio speaker, such as speaker 3252 of patient control unit 3210, shown in FIG. 32, or directs the audio signal from microphone 3620 to transformer 3616.

Preferably, audio controller 3614 is a 34118 audio controller manufactured by Motorola. Audio input signals from audio matrix 2510 which pass through the audio controller are directed to patient station speaker 3618 via amplifier 3622 and/or to audio output ports 3624 via amplifier 3626 and relay controller 3628. Audio signals generated by the patient station via microphone 3620 are electively transferred through audio controller 3614 onto he audio pair as shown. Mute switch 3630 may be provided to allow a staff member to manually short out the microphone so as to prevent audio signals from being generated at the patient station. In addition, the audio circuitry for the patient station may include input audio ports 3632 which facilitate a connection between external entertainment equipment, such as a television or a radio, and audio output ports 3624 via relay switch 3628. To illustrate, audio signals from a television in the patient's room can be directed from patient station 2416 to speaker 3252 in patient control unit 3210 (shown in FIG. 32) to bring the audio from the television closer to the patient.

Figure 37A:
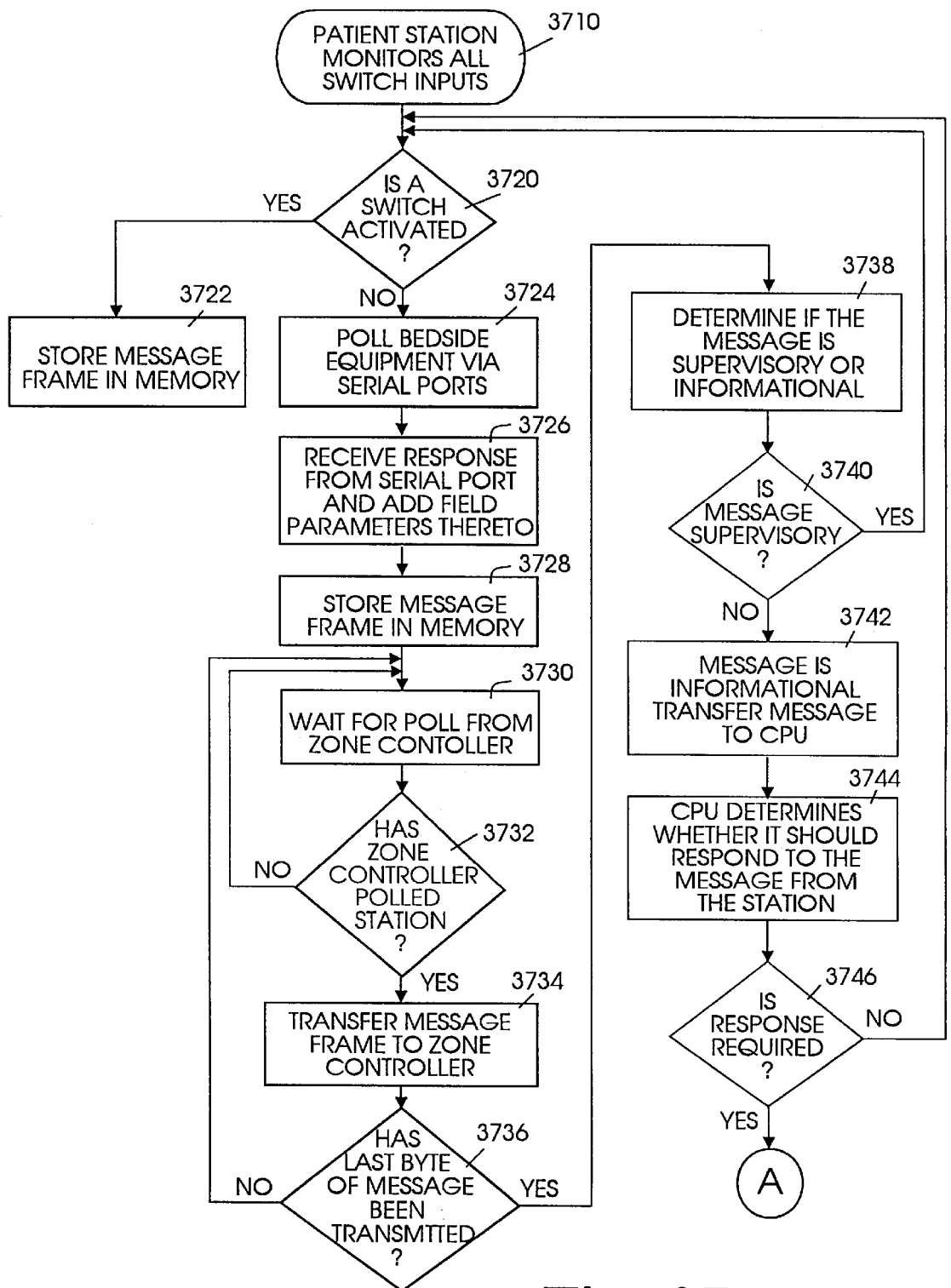
FIGS. 37a and 37b illustrate an exemplary flow-chart diagram of an operation of the patient station of FIG. 24.
Figure 37B:
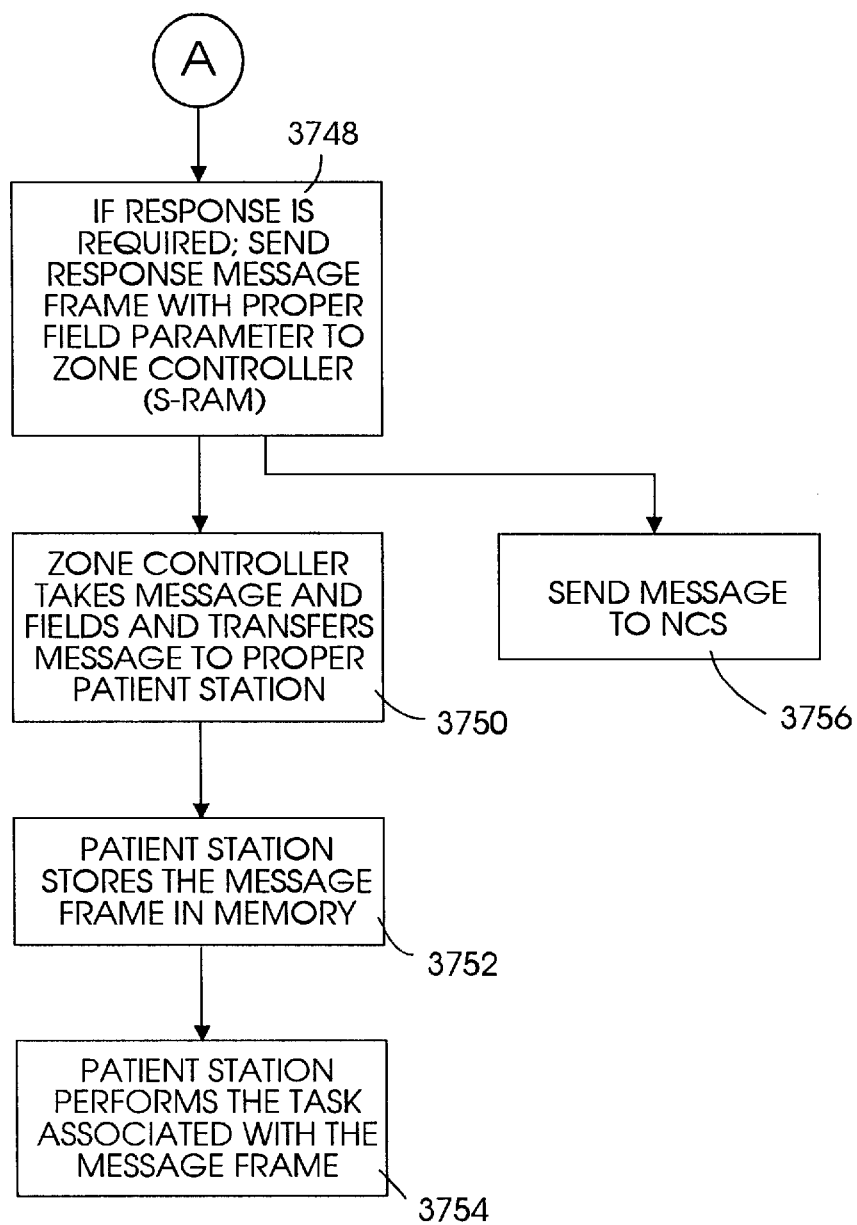

Referring again to FIG. 32, each patient station 2416 may be coupled to external peripheral equipment, such as controllers, indicators and/or switches, which provide medical instrument data and/or patient status data to staff members and which facilitate patient control of environmental facilities within the patient's room, as will be described below. FIGS. 37a and 37b represent an exemplary operational flow-chart of the interaction between the patient station and the bedside equipment and between the patient station and the CPU so as to facilitate communication between the bedside equipment and the CPU. Initially, the patient station monitors the inputs from the external peripheral equipment (e.g., switches) to determine if the equipment has been activated (steps 3710 and 3720). If a switch or other peripheral equipment is activated, a message frame associated with the activated switch will be stored in the memory of patient station circuitry 3510, shown in FIG. 35 (step 3722) and transferred to zone controller 2420. If, on the other hand, a switch has not been activated then the patient station will poll the bedside equipment via serial port 3534 (shown in FIG. 35) for status or message information and interpolate field parameters onto the received message (step 3724 and 3726). The message frame is then stored in patient station memory 3516 (shown in FIG. 35) and remains therein until the patient station 2416 is polled by the zone controller 2420 corresponding to the patient station (steps 3728, 3730 and 3732).

Once polled, the patient station transfers the message frame to the S-RAM 2512 (shown in FIG. 25) of the zone controller until the last byte of the frame has been transferred (i.e., the F bit is set to logic 1) (steps 3734 and 3736). The zone controller then determines if the message frame, received is an S-frame or an I-frame, and if the message frame is an S-frame the zone controller acknowledges the message frame and the patient station returns to monitor the switch inputs (steps 3738 and 3740). If the received message frame is an I-frame the frame is transferred to the CPU which determines whether a response to the transmitting station is required (steps 3742, 3744 and 3746). If no response is required the CPU stores the received data and the patient station returns to monitor the switch inputs, as shown. If, however, a response is required a response message frame is sent to the zone controller and stored in the S-RAM (step 3748). The zone controller polls the patient station and if a received ready (RR) command is received in return, the response message frame is transferred to and stored in the patient station (steps 3750 and 3752).

Once the response message frame is received the patient station performs the task associated with the information in the frame (step 3754). In addition to sending a response message to the patient station, the CPU may also be required to send a message frame to the nurse control station to alert staff members of potential faults either through tone and visual indications similar to those illustrated in FIG. 41 or by adding the information to the problem report described above (step 3756).

Referring again to FIG. 32, in the preferred embodiment, patient station 2416 is connected to patient control unit 3210 via data link 3246. Patient control unit 3210 includes control buttons 3248 which facilitate patient control of the environmental facilities within the patient's room, via patient station 2416 and CPU 2412. Such environmental facilities include, for example, the television, radio, draperies and the room lighting.

Nurse call button 3250 is provided to enable the patient to call the nurse control station or stations within the group. As noted above, the communication between stations is facilitated by CPU 2412 utilizing the master/slave communication link described above.

Figure 38:
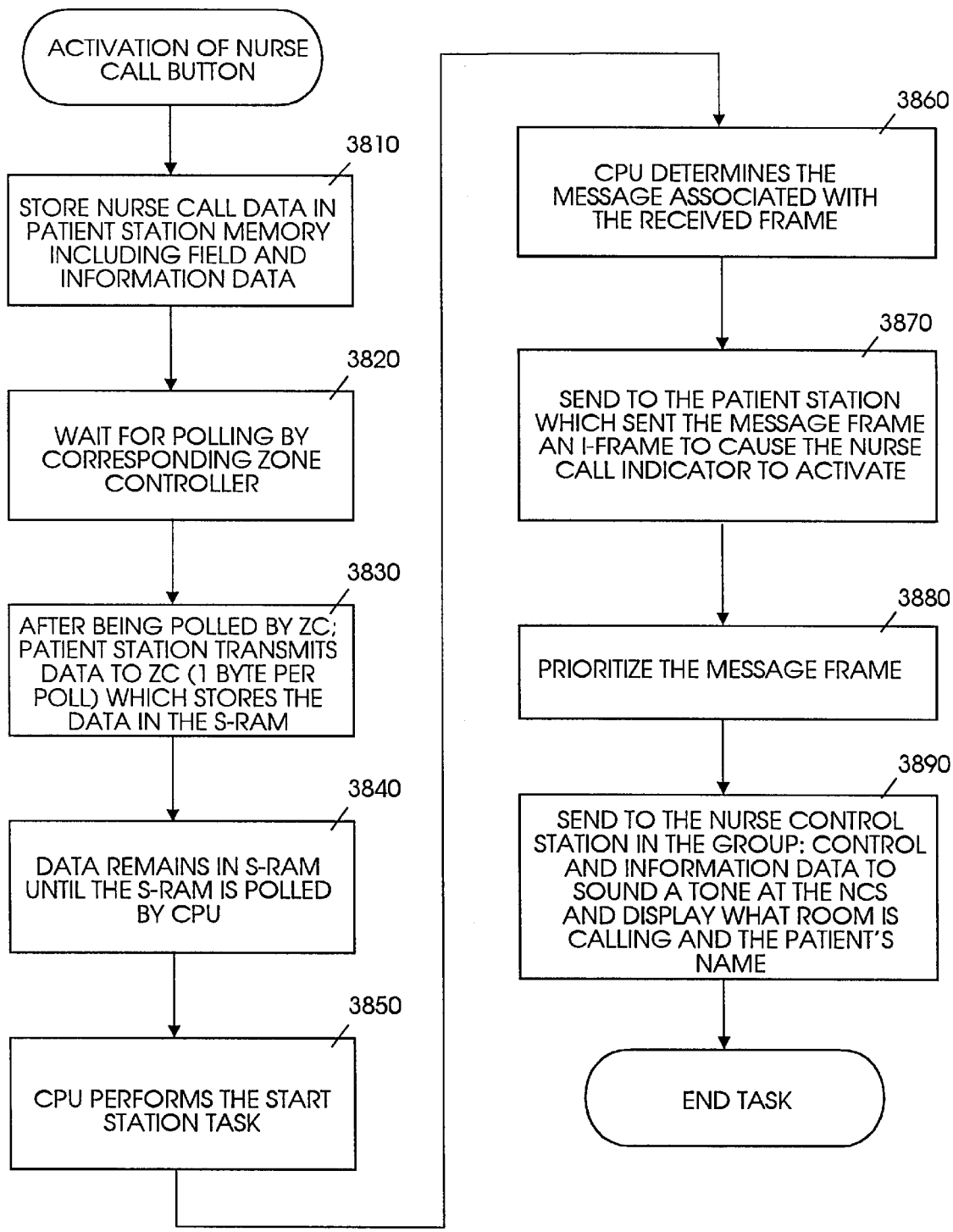
FIG. 38 is a flow-chart diagram associated with the internal circuitry for the patient stations illustrated in FIG. 24.

FIG. 38 illustrates an exemplary operational flow for the patient control unit 3210 in combination with patient station 2416. Upon activation of nurse call button 3250 of patient control unit 3210 (shown in FIG. 32), patient station 2416 receives the switch activation data via data link 3246 and buffers 3530 (shown in FIG. 35). Microprocessor 3512 then interpolates field data onto the received message to form a message frame, as described above, and stores the message frame in RAM 3518 (step 3810).

Once stored in memory, the nurse call data remains therein until the patient station is polled by the zone controller (step 3820). Once polled, the message frame is then transferred to the zone controller and stored in the S-RAM (step 3830). The data remains in the S-RAM until the S-RAM is polled by CPU 2412, upon which, the message frame is then transferred to the CPU (step 3840).

Reception of the message frame in the CPU causes the CPU to begin the station task identified in the INFORMATION field of the I-frame (step 3850), to determine the message received from the patient station and provide an appropriate response thereto (steps 3860 and 3870). For this example, CPU 2412 is responding to the activation of nurse call button 3250 of patient control unit 3210. The initial response to the activation of the nurse control button is to return a message frame to the patient station to activate nurse call indicator 3222 of indicator assembly 3220 (shown in FIG. 32). In addition, the CPU prioritizes the message frame utilizing the transition priority data of the PATH field and then sends to the nurse control station or stations connected in the group associated with the patient station, a message frame including tone and display data identifying the patient and the associated room number (steps 3880 and 3890). At this point, the station task is completed and the CPU returns to the listen task. Manual reset of the patient station by a responding staff member deactivates indicator 3222 and clears the message from the nurse control station display.

Referring once again to FIG. 32, patient station 2416 may also be connected to staff presence switch 3254, indicator assembly 3220, code blue switch 3234 and/or emergency code switch 3232. In the configuration shown, staff presence switch 3254 is connected to patient station 2416 via data link 3256 and when properly activated provides patient station 2416 with a signal indicative of the type of staff member present in the patient's room. Once activated, a message frame (e.g., an I-frame) is transferred to the CPU and an appropriate response is returned to that particular patient station, in a manner described above.

The responding frame from the CPU 2412 includes information to cause the activation of an indicator in indicator assembly 3220 which corresponds with the type of staff member in the patient's room. To illustrate, if the staff member entering the patient room is a registered nurse (RN), that person would activate switch 3258 which in turn would activate indicator 3224 of indicator assembly 3220 via patient station 2416 and CPU 2412. If the staff member entering the room is a licensed practical nurse (LPN), that person would activate switch 3260 of staff presence switch 3254, which in turn would activate indicator 3226 of indicator assembly 3220 via patient station 2416 and CPU 2412. If, on the other hand, the staff member entering the room is an aide, then that person would activate switch 3262 of staff presence switch 3254, which in turn would activate indicator 3228 of indicator assembly 3220. When the staff member leaves the patient's room, the particular staff member switch is deactivated so as to deactivate indicator assembly 3220.

In the preferred embodiment, indicator assembly 3220 is a four lamp light fixture (e.g., a dome lamp) having colored lenses associated with each lamp. The fixture is secured or otherwise positioned on the wall outside the patient's room, preferably above the doorway, to allow staff members in the hallway to simply look at each indicator assembly and determine the type of staff member in a particular patient's room, if any. Alternatively, the indicator assembly may be any known type sufficient to provide staff members with an indication as to the type of staff member in a patient's room, for example, the indicator may be a LCD display which identifies the type and the name of the staff member in the patient's room in response to information provided to the system by the above described staff locator system, described in more detail in commonly assigned U.S. application entitled "An Apparatus For Automating Routine Communication in a Facility", naming John Chaco as the inventor and filed Aug. 3, 1992, which is a continuation-in-part of copending U.S. patent application Ser. No. 07/559,196, filed on Jul. 27, 1990, the disclosure of which is incorporated herein by reference.

Figure 32:
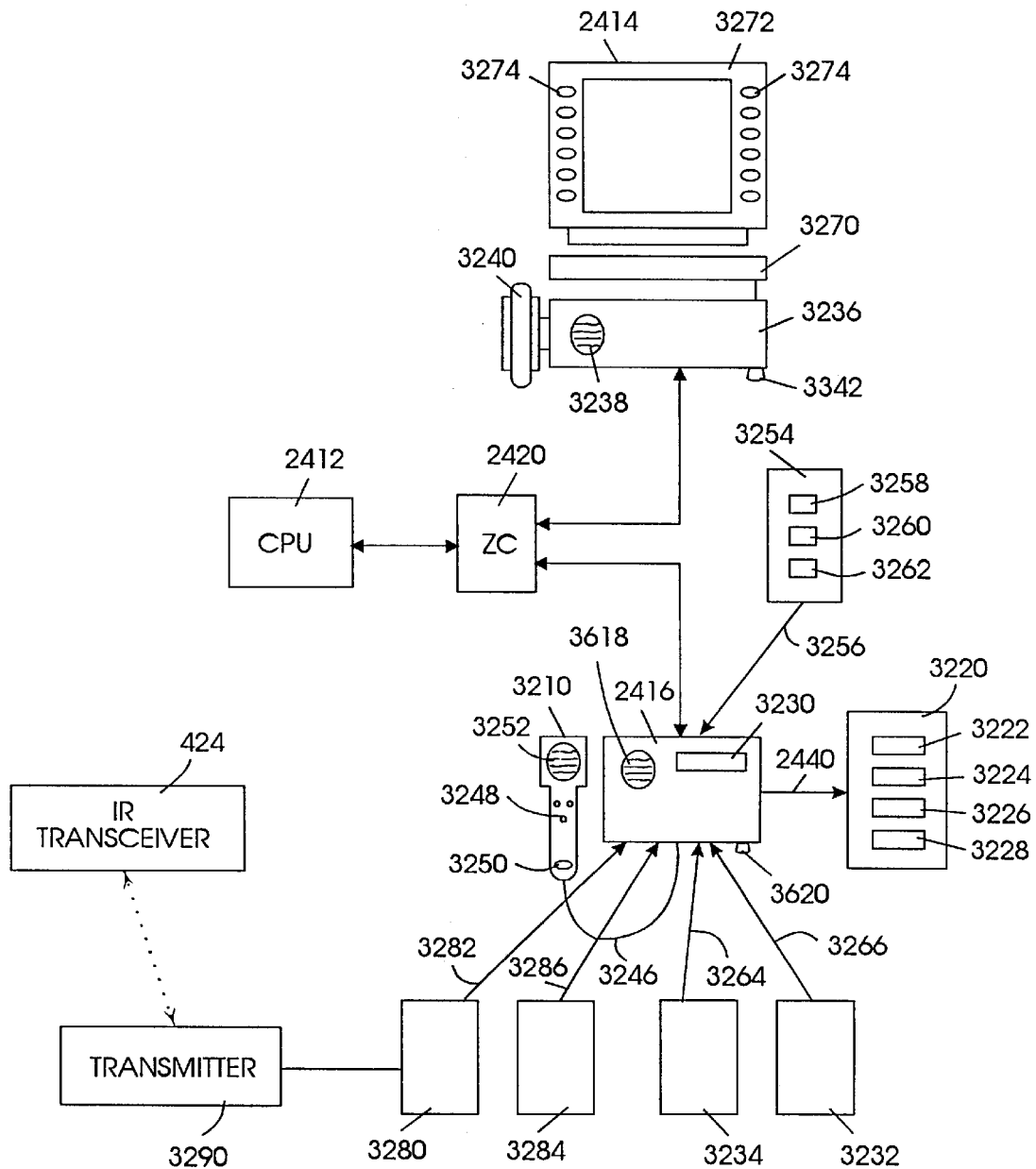
FIG. 32 is a functional block diagram of a system configuration similar to FIG. 24, illustrating a patient station having peripheral equipment connected thereto.

Code blue switch 3234 and emergency code switch 3232 are connected to patient station 2416 via data links 3264 and 3266, respectively, as shown in FIG. 32, and are provided to allow staff members to initiate code blue or emergency responses directly from the patient's room. As noted above, code blue and/or emergency code procedures may also be initiated from nurse control station 2414. Initiation of the code blue response procedure at a patient station 2416 will result in the following occurrences. Initially the code blue data signal received from the code blue switch is stored in the patient station memory as a message frame, in a manner described above. The microprocessor 3512 (shown in FIG. 35) in the patient station 2416 then waits to be polled from the zone controller 2420 before transferring the data to the zone controller. Once polled by zone controller 2420 the message frame is transmitted to the zone controller and stored in the S-RAM 2512 until the S-RAM is polled by CPU 2412. Once the message frame is received within the CPU the message frame is prioritized and the station task associated with the data within the INFORMATION field of the message frame is initiated.

An example of a station task performed by the CPU in response to the activation of a code blue switch will be described below. Initially CPU 2412 determines the message type received from zone controller 2420. Next the CPU performs whatever function is associated with the message, in this example the message relates to the code blue function. In response to the code blue function, the CPU 2412 sends to the particular patient station an I-frame which includes data to cause activation of particular peripheral equipment as well as devices within the patient station 2416, e.g., a tone code and an indicator assembly activation code. Next CPU 2412 determines which staff station or stations 2418 and which nurse control station or stations 2414 are grouped with the subject patient station 2416. Thereafter, CPU 2412 sends to each associated staff station an I-frame including message data to display "code blue" on staff station display 2422 of staff station 2418. Next CPU 2412 sends a message to the ZIA 3022, shown in FIG. 30, to activate the proper indicator associated with the patient station group in a manner similar to that described above with reference to fail safe bus 3020.

The CPU 2412 then sends an I-frame to each nurse control station grouped with the patient station to display the room number and identity of the patient subject to the code blue function, on the display of the nurse control station. The CPU 2412 then sends to the nurse control station an I-frame including appropriate control signals associated with the patient station message. Once the above steps are accomplished the station task is completed and the CPU 2412 returns to the listen task.

The system of the present invention may also be configured to monitor medical equipment being used to treat the patient (i.e., bedside equipment). Such bedside equipment may be connected to communication port 3534 (shown in FIG. 35) of patient station 2416. In instances where the serial data from the bedside equipment is not configured for RS-485 protocol, serial data converter 2520 (shown in FIG. 25) may be interconnected between serial port 3854 of patient station 2416 and the serial port of the bedside equipment. Typically, the serial port of the bedside equipment is configured to operate with RS-232 protocol, thus, serial data converter 2520 would be an RS-485 to RS-232 converter which is known in the art.

Examples of the above described bedside equipment are shown in FIGS. 32. As shown, a heart rate monitor 3280 is connected to patient station 2416 via data link 3282, which as noted above is operatively connected to nurse control station 2414 via zone controller 2420 and CPU 2412. The patient station (acting as a master station) polls heart rate monitor 3280 (operating as a slave station) to verify that the patients heart rate falls within the proper range as determined by the monitor. The zone controller periodically polls patient station 2416, as described above for an S-frame or an I-frame message frame. Typically with respect to this example, if no fault is detected the patient station will respond to the polling of the zone controller with an S-frame indicating proper operation of heart rate monitor 3280. However, a fault detected in monitor 3280 will be stored in RAM 3518 of patient station circuitry 3510 (shown in FIG. 35) along with the appropriate field data in the form of an I-frame, and the I-frame is transferred to zone controller 2420 and CPU 2412 in a manner described above. The CPU then analyzes the I-frame and an appropriate alarm sequence is initiated to notify staff members at nurse control station 2414 of the detected fault.

As another example, an intravenous (IV) pump 3284 is connected to patient station 2416 via data link 3286, which as noted above is operatively connected to nurse control station 2414, via zone controller 2420 and CPU 2412. In this example, the IV pump is periodically monitored by patient station 2416 to ensure the flow rate of the pump is appropriate. If a failure is detected, a message frame including the error message is transferred to CPU 2412 in a manner set forth above. The CPU the initiates an appropriate alarm sequence, such as displaying a message on the monitor of nurse control station 2414, that the IV container is empty and needs to be changed. It should be noted, that numerous other types of bedside equipment may be monitored by the system of the present invention, including respirators and heart monitors.

Transmitter 3290 is hardwired to the bedside equipment, e.g., heart rate monitor 3280, and is provided to enable central computer system 432 (shown in FIG. 4) to determine what room or other area of the health care facility the bedside equipment is located and to transmit operation data generated by the bedside equipment, such as status data or other data associated with the operation of the equipment. In this configuration, transmitter 3290 transmits an identification signal and the operation data to IR transceiver 424 which is in communication with central computer 432 through network server 430, as shown in FIG. 4 and described above. Central computer 432 determines which transceiver received the identification signal of the bedside equipment and transfers the location data of the equipment and the operation data to CPU 2412 via data link 2728 (shown in FIG. 27). Transmitter 3290 may be a radio frequency transmitter operating at a frequency of approximately 300 MHz, which are available from Dallas Semiconductor, Inc.

Staff Station

Referring again to FIG. 24, staff station 2418 is similar in design to patient station 2416. In the preferred embodiment, staff station 2418 may be configured, in the initial system configuration setup, to operate in a "duty" mode or a "staff" mode. In the "duty" mode staff station 2418 provides patient call indications on staff station display 2422, as well as facilitating communication with nurse control station 2414. In the "staff" mode staff station 2418 facilitates communication with nurse control station 2414.

Figure 39:
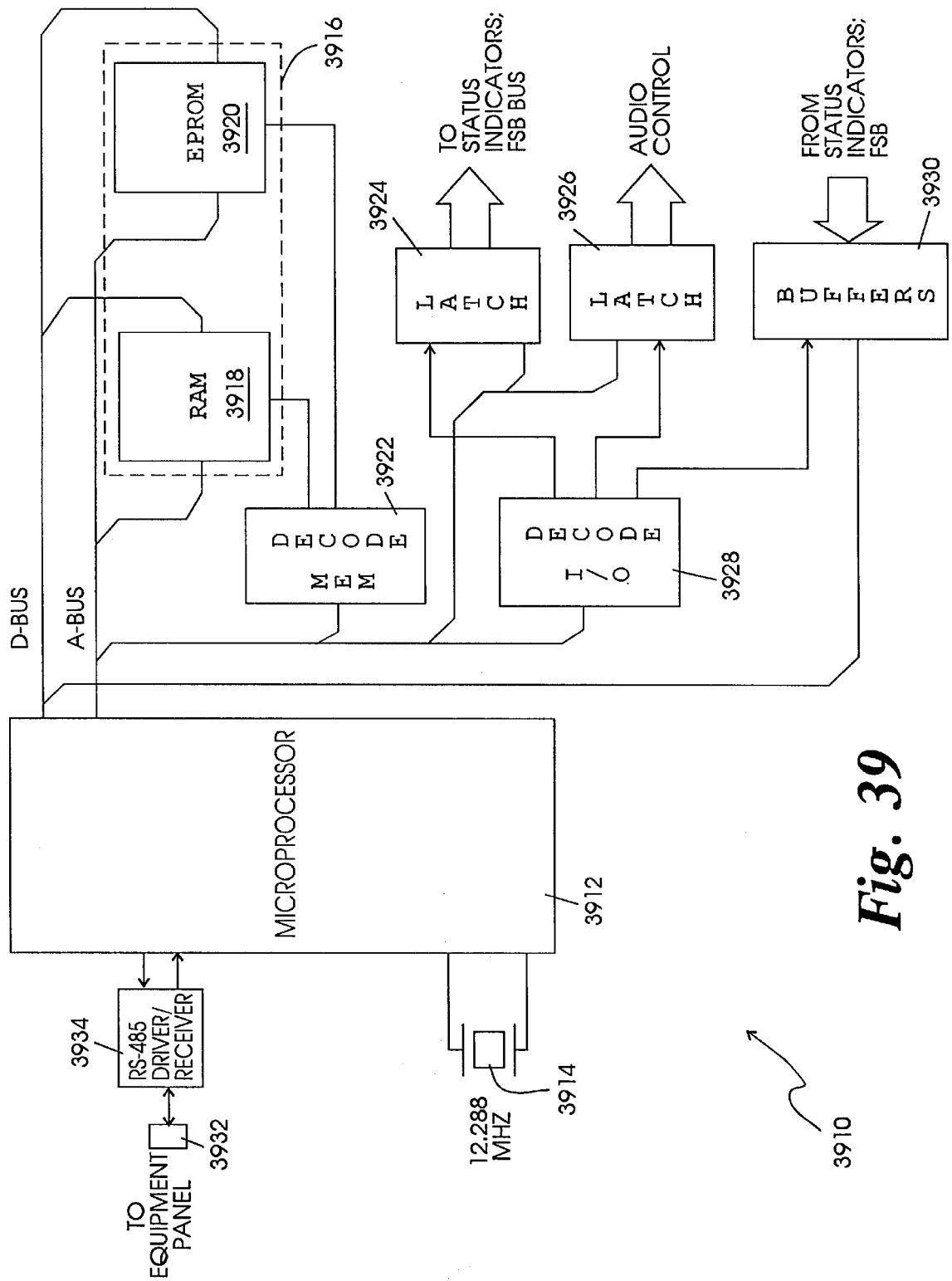
FIGS. 39 and 40 are circuit block diagrams for the internal circuitry for the staff stations illustrated in FIG. 24.

FIG. 39 illustrates hardware configurations for the staff station circuitry 3910 installed within staff station 2418. The staff station circuitry 3910 includes microprocessor 3912, such as model 64180 manufactured by Motorola operating at a frequency of 12.888 MHz. via crystal 3914, 96 Kbytes of memory 3916 (e.g., 64 Kbytes of flash ROM and 32 Kbytes of RAM) having stored programs, e.g., system and application programs. In this exemplary configuration, the data and address buses of the microprocessor are connected to the memory, e.g., RAM 3918 and an EPROM 3920. Memory decoder 3922 is utilized to select between RAM 3918 and EPROM 3920 in response to a particular address on the address bus. The address bus is also connected to a pair of latches 3924 and 3926 which interface the microprocessor to status indicators, the fail safe bus (FSB), the audio control circuitry, and to switches and other peripheral equipment connected to the staff station, as shown. In addition, I/O decoder 3928 is utilized to select between either latch in response to a particular address on the address bus. Incoming signals from the above noted peripheral equipment are received by buffer 3930 and then transferred to the data-bus upon being enabled by I/O decoder 3928.

Utilizing the preferred microprocessor (i.e., the Motorola 64180), serial communication between the zone controller and the microprocessor may be accomplished through asynchronous serial communication port 3932 which is, preferably, configured to RS-485 protocol utilizing RS-485 driver/receiver (RS-485 D/R) 3934 as shown.

Figure 40:
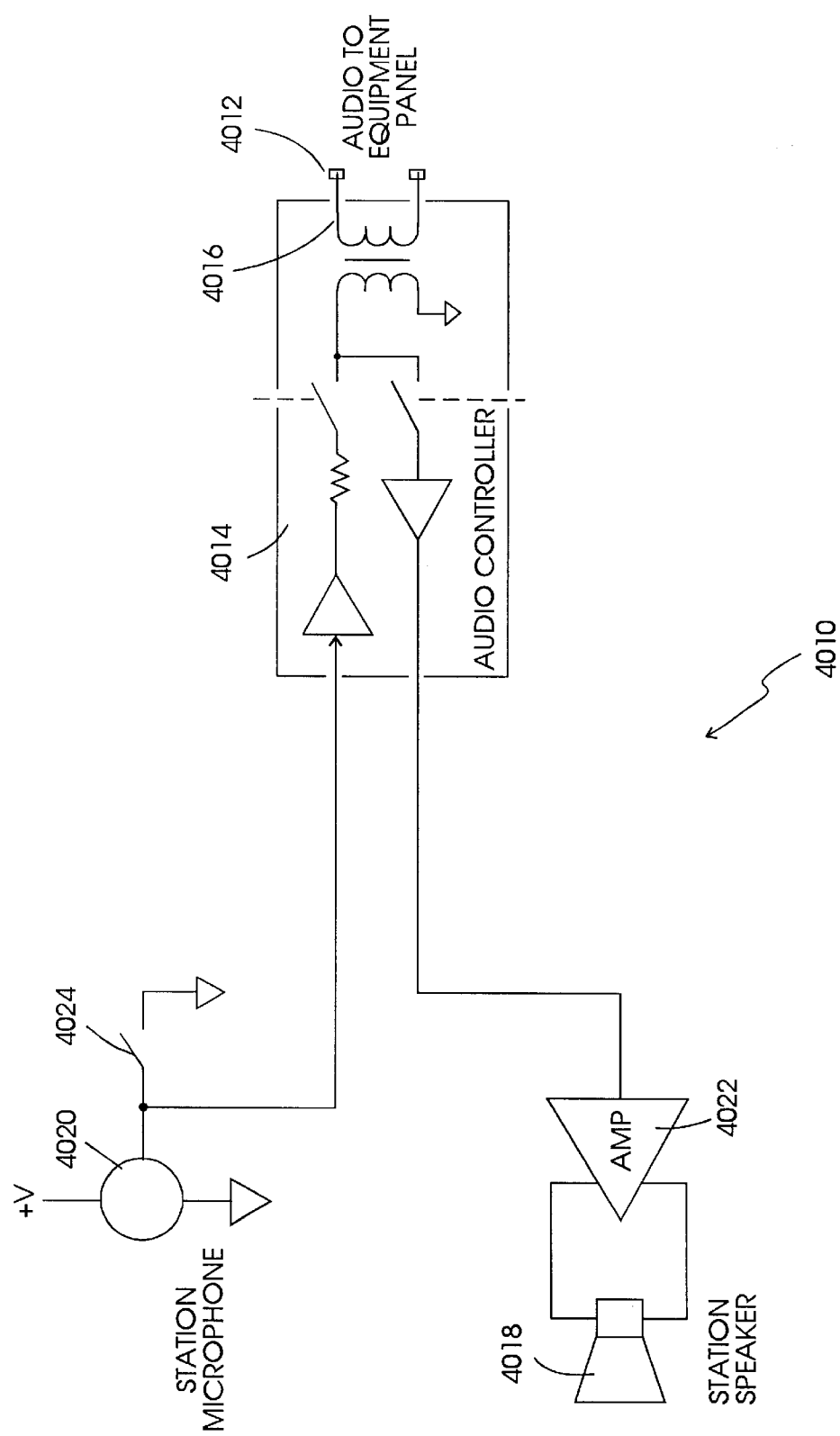

FIG. 40 illustrates hardware configurations for the audio portion 4010 of staff station 2418. As shown, audio pair 4012 from an equipment panel (e.g., audio matrix 2510 shown in FIG. 25) is connected to the front end of audio controller 4014. Preferably, the front end of audio controller 4014 includes a coupled 600 ohm balanced transformer 4016 which isolates the internal audio circuitry of staff station 2418 from the external audio circuits. Depending upon whether the audio signal is being received or transmitted, the back end of audio controller 4014 directs the audio signal to staff station speaker 4018 or directs the audio signal from microphone 4020 to audio matrix 2510 via audio controller 4014.

Preferably, audio controller 4014 is a 34118 audio controller manufactured by Motorola. Audio input signals from audio matrix 2510 which pass through the audio controller are directed to staff station speaker 4018 via amplifier 4022. Audio generated by the staff station via microphone 4020 is selectively transferred through audio controller 4014 onto the audio pair as shown. Mute switch 4024 may be provided to allow a staff member to manually short out the microphone so as to prevent audio signals from being generated at the patient station.

System Functions

The patient care and communication system of the present invention may be programmed to perform numerous operations associated with patient care and communications within a hospital or other health care facility. The following functions are exemplary of the numerous types of features and the functional flow (or data exchange) between the different stations, the CPU and the zone controller utilize the above described preferred master/slave communication link.
a. Call priority Message frames usually in the form of an I-frame originated by a nurse control station, a patient station and/or a staff station are interpreted by CPU 2412 and assigned a priority level based upon the type of message frame received (i.e., the DTYPE field of the INFORMATION field contains the message type which corresponds to the priority level that will be assigned to the frame). In addition, the message associated with the TEXT field of the message frame is displayed on nurse control station display 3272 of a nurse control station 2414 in order of priority level. The priority levels are preprogrammed during the initial set-up of the system configuration, but may be altered by staff members at nurse control station 2414 via keyboard 3236 or direct select keys 3274 (shown in FIG. 32). The highest priority call will be displayed first and other calls will follow in descending order according to the priority level.

Preferably, each call originated has specific audible and visual signaling based on the call priority level which are distributed to the necessary nurse control stations, zone indicator assembly, patient stations and/or staff stations via CPU 2412 and their respective zone controller. FIGS. 41–43 represent tables illustrating exemplary embodiments of call priority levels, their associated visual and tone indications which are generated at either the nurse control station, the patient station and/or the staff station. FIG. 41 illustrates the preferred visual display which appear on nurse control station display 3272 and the tones generated at speaker 3238 (shown in FIG. 32) in response to the various priority levels. For example, in response to the activation of code blue switch 3234 (shown in FIG. 32) CPU 2412 will transmit to nurse control station 2414 a message frame instructing the nurse control station to display on the nurse control station display 3272 a flashing arrow directed at a direct select key 3274 to indicate which key will enable the staff member to connect the audio of the nurse control station to the audio of the patient station and respond to the call. The arrow will flash at a rate of approximately 120 pulses per minute (PPM). In addition, the room number and bed number associated with the patient station to which the code blue switch is connected and the "CODE BLUE" message will be displayed on nurse control station display 3272. An audible tone at the rate of 120 PPM will also be generated at speaker 3238 of nurse control station 2414.

The preferred response at patient station 2416, shown in FIG. 42, to the activation of the code blue switch will be to pulse a station call and bed call placement LED indicators (not shown), which may be positioned on the front panel of patient station 2416, at a rate of 120 PPM, and to pulse a code blue indicator of the corresponding group indicator assembly 3024 via ZIA 3022 (shown in FIG. 30) at a rate of 120 PPM.

The preferred response at staff station 2418, shown in FIG. 43, to the activation of the code blue switch will be to pulse an incoming call LED indicator which may be positioned on the front panel of staff station 2418, at a rate of 120 PPM, to display on staff station display 2422 (shown in FIG. 24) the room and bed number associated with the patient station to which code blue switch 3234 is connected and to display the "CODE BLUE" message; to pulse a blue indicator of the corresponding group indicator assembly 3024 via ZIA 3022, at a rate of 120 PPM; and to generate an audible tone at the rate of 120 PPM at speaker 4018 of staff station 2418 (shown in FIG. 24).

b. Nurse Follow

The nurse follow feature allows a staff member to selectively direct incoming calls to a particular nurse control station to selected patient stations and/or staff stations. To illustrate, this feature may allow the staff member to program the nurse control station to distribute incoming calls to a single patient station, to patient stations where particular staff members have activated respective staff presence switches (e.g., switch 3254, shown in FIG. 32) and/or to all patient or staff stations assigned to the group associated with the particular nurse control station. Thus, when a staff member is required to leave the area of a nurse control station, incoming calls to the nurse control station can be routed to locations where appropriate staff members can respond to the call.

In operation, a staff member attending nurse control station 2414 may utilize direct select keys 3274 (show in FIG. 32) in response to menu driven prompts to configure the system to operate in the nurse follow mode. In the nurse follow mode, calls which are directed to the nurse control station 2414 via CPU 2412 and corresponding zone controllers 2420 will automatically be routed to the station or stations selected by the staff members or to stations in locations where that staff member or other staff members are determined to be present by staff locator system 2428 (shown in FIG. 27 and described above with reference to FIGS. 1 through 23).

For example, if the staff member selects the nurse follow feature which routes incoming calls to patient stations where the RN switch 3258 of staff presence switch 3254 (shown in FIG. 32) has been activated, CPU 2412 will direct the incoming call to the nurse control station to any room in the group where switch 3258 of staff presence switch 3254 has been activated.

As another example, CPU 2412 of the patient care and communication system interacts with central computer system 432 of staff locator system 2428, shown in FIGS. 4 and 27. In this configuration, the identification badges 1111 are in communication with central computer system 432 in a manner described above with particular reference to FIGS. 4 and 17c. The identification badge 1111, which is worn by the staff member, continually transmits the identification signal (of the staff member) and central computer system 432 continually monitors the identification signal to update the location of the badge (and the staff member). The location information of the staff member is transferred to CPU 2412 via data link 2726 (shown in FIG. 27) which may be any known type of communication link utilized to facilitate communication between computer systems. Therefore, when a call is directed to a nurse control station 2414 programmed to operate in the nurse follow mode, CPU 2412 will route the incoming call to a station (either 2416 or 2418) positioned nearest the detected location of the staff member. In an alternative embodiment, a staff member attending the nurse control station may want to route incoming calls to locations of other staff members. In this embodiment, the nurse control station can be programmed in the nurse follow mode to route the incoming calls intended for nurse control station 2414, to stations where the other staff members have been detected by the staff locator system.

c. Voice Paging

Figure 44:
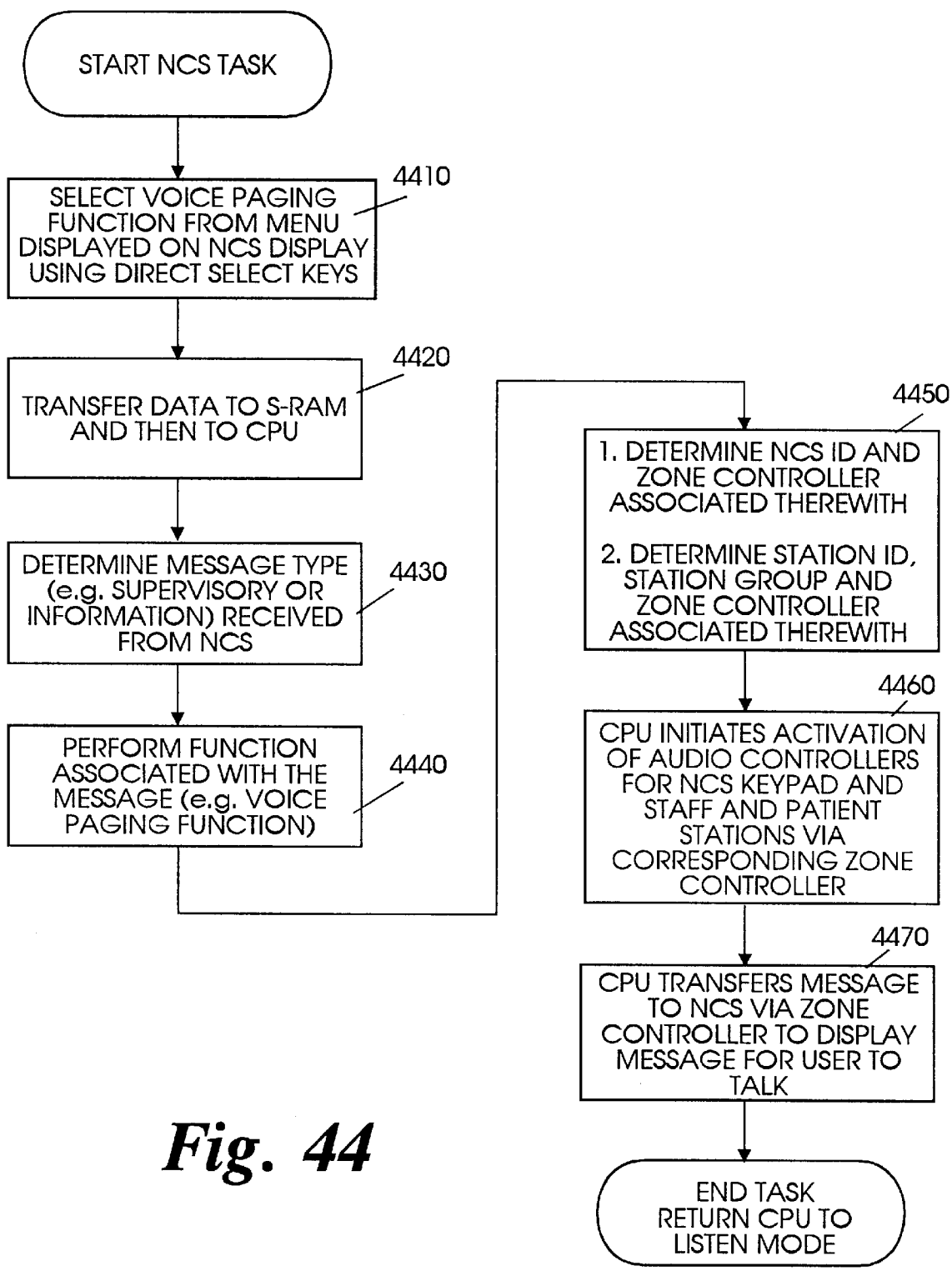
FIG. 44 is flow-chart diagram for the central processing unit illustrated in FIG. 35.

The voice page feature allows staff members to communicate to selected patient and/or staff stations from the nurse control station. To illustrate, this feature allows a staff member to communicate to all staff members 10 who have activated staff presence switches associated with the nurse control station (i.e., within the same group) and all staff members in areas where staff stations are located. FIG. 44 illustrates an exemplary operational flow for the voice paging feature of the present invention. Initially, the staff member desiring to page all staff members within the assigned group, programs nurse control station 2414 via direct select keys 3274 (shown in FIG. 32) which activate menu driven functions (step 4410). The menu driven instructions from the nurse control station are then transferred to the CPU via zone controller 2420 in a manner described above (step 4420). The CPU analyzes the instructions, e.g., determines the identification of the patient and/or staff stations and their associated zone controllers and the CPU performs the function associated with the received message frame (step 4430, 4440 and 4450). Thereafter, the CPU causes the audio connection between each station and the nurse control station and notifies the paging staff member to begin talking (steps 4460 and 4470).

Alternatively, the voice paging feature may utilize staff locator system 2428, shown in FIGS. 4 and 27 to determine the location of a staff member or members so that the staff member attending nurse control station 2414 may communicate with the patient and/or staff stations nearest to each staff member or members being paged.

d. Room Monitoring

The room monitoring feature allows staff members attending a nurse control station 2414 to activate the audio system of either a selected number of patient stations 2416 or to manually step or automatically scan through each patient station 2416 in each room associated with the station grouping, described above, in a predetermined order for a predetermined period of time so as to activate microphone 3520 of patient station 2416, enabling staff members to listen for sounds of distress or other uncharacteristic noises so as to check on the well being of a patient or patients. Preferably, the predetermined order for monitoring rooms is from the lowest room number to the highest and the predetermined period of time is approximately ten seconds. In operation, the staff member attending nurse control station 2414 configures the system for automatic room monitoring by depressing direct select keys 3274 of nurse control station display 3272 in response to menu driven prompts. Once configured for automatic monitoring, CPU 2412 sends a message frame to each patient station in the above noted order to activate microphone 3620 (shown in FIG. 36) of audio circuitry 3610, via audio controller 3614, for a period of ten seconds to allow the attending staff member to listen for distress noises and other uncharacteristic noises.

Diagnostics

The system of the present invention also provides diagnostic features which continuously monitor system components. As noted above, system faults are communicated to the nurse control station and/or to the staff station and added to the problem report. Hard and/or soft copies of the problem report may be obtained from printer 2724 and/or external computer 2722 (shown in FIG. 27) or the problem report may be displayed on nurse control station display 3272 when the "problem reports" feature is selected by direct select keys 3274 shown in FIG. 32.

In addition, the operation of selected periphery devices in the patient's room are continuously monitored and 1o any failures are brought to the attention of the staff member at a nurse control station within the group. For example, the wiring to code blue switch 3234, the smoke alarm and/or the nurse call button 3250 on patient control unit 3210 may be monitored for damaged to the wires between such periphery devices and patient station 2416.

Figure 45:
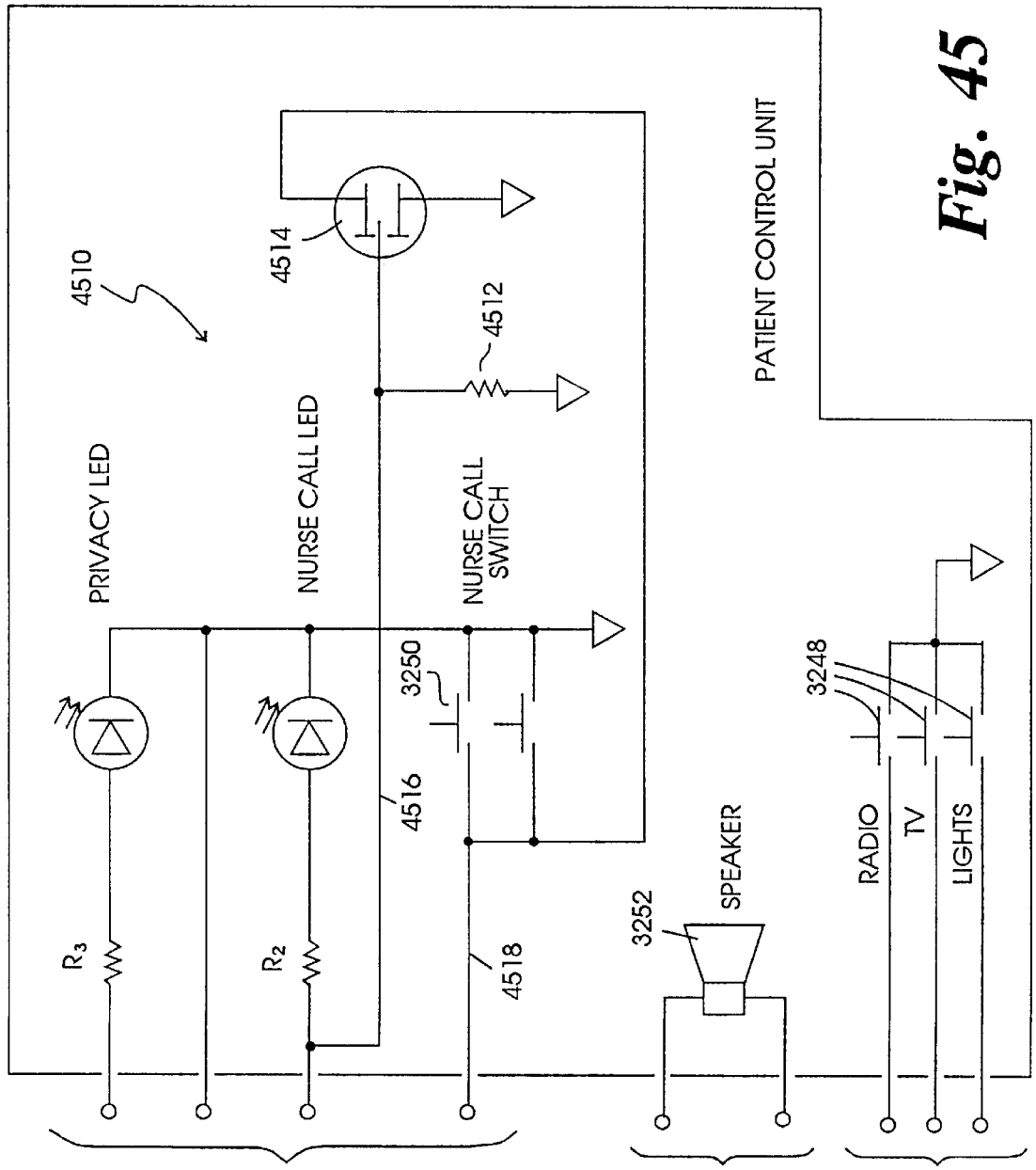
FIG. 45 is a circuit diagram for the patient control unit illustrated in FIG. 33 and showing self-test circuitry for performing automatic continuity tests of interconnecting wires.

FIG. 45 shows the hardware components for patient control unit 3210 which is connected to patient station 2416. Preferably, the wiring is tested by microprocessor 3512 (shown in FIG. 35) activated signals in combination with the wire test circuitry 4510. Wire test circuit 4510 includes resistor 4512 and field effect transistor (FET) 4514 which are connected between call wire 4516 and nurse call wire 4518, as shown. In this configuration, microprocessor circuitry 3510 of patient station 2416, shown in FIG. 35, periodically turns on FET 4514 via call wire 4516 therefore completing the ground path connecting call wire 4516 and nurse call wire 4518. Microprocessor 3512 then interrogates nurse call wire 4518 via buffer 3530 (shown in FIG. 35) in response to microprocessor driven instructions, so as to perform a continuity check of the nurse call feature of patient control unit 3210. Preferably, the period between each wire test is two seconds. Wire test circuit 4510 may be utilized to perform wire tests between any periphery equipment and the processor associated with the station to which the peripheral equipment is connected. In the event the continuity check fails, a failure alarm sequence is initiated to notify staff members of the wire failure and which wire in which periphery device has failed.

The patient care and communication system of the present invention also includes external diagnostic device 2570 connected to serial data converter 2520, as shown in FIG. 25. Preferably, external diagnostic device 2570 is a modem provided to facilitate external diagnostics of the patient care and communication system of the present invention, via converter 2520 and zone controller 2560. External diagnostic device 2570 allows a technician or other service personnel to remotely verify and update the configuration of the system in a manner similar to that performed by staff members attending a nurse control station. In addition, the external diagnostic device 2570 allows the technician or other service personnel to view the system problem report which, as noted above, includes information as to which stations or equipment are not operational.

It will be understood that various modifications can be made to the embodiments of the present invention herein disclosed without departing from the spirit and scope thereof. For example, various system configurations are contemplated, as well as various types of protocols utilized to communicate between the numerous stations utilized within the system of the present invention. In addition, numerous functions aside from those described herein may be programmed and performed in the system of the present invention. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. A patient communication system, which comprises:
   a central station having means for storing patient data and for determining the location of personnel within a health care facility;
   a plurality of portable badges, each configured for attachment to individual personnel and having a database for storing information including identity information about the individual personnel to which said respective badge is attached, and configured to transmit at least a portion of said information to one of a plurality of receivers, said plurality of receivers being coupled to said central station to transfer signals representing information received from said badges to permit said central station to determine the location of each individual personnel;
   at least one patient station, positioned in one of a plurality of patient rooms, said patient station being coupled to said central station and having a processor which facilitates data signal communications with said central station; and
   at least one indicator assembly for signaling the presence of the individual personnel in said one of a plurality of patient rooms, coupled to said at least one patient station such that when said central station determines the location of personnel in said one of a plurality of patient rooms, said central station transfers to said at least one patient station actuation signals to actuate said indicator assembly.

2. The system according to claim 1, wherein said indicator assembly is deactuated by said at least one patient station when said central station determines that the personnel has left said predetermined location.

3. The system according to claim 1, wherein said indicator assembly includes a plurality of indicators for indicating different status conditions and said actuation signals from said central station includes signals to activate a selected at least one of said plurality of indicators.

4. The system according to claim 1, wherein said indicator assembly includes a plurality of indicators each representing a predefined personnel group, and said central station determines from said identity information the location and personnel group of personnel, such that when said central station determines the presence of personnel in said predetermined location said central station transfers to said at least one patient station actuation signals to actuate one of said plurality of indicators associated with said personnel.

5. The system according to claim 1, wherein each of said badges includes switch means for transmitting a predefined signal to said central station.

6. The system according to claim 1, wherein said patient station includes display means for displaying information including information received from said central station.

7. The system according to claim 1, further including patient monitoring means for monitoring patient status conditions, said patient monitoring means being connected to said patient station for forwarding said patient status conditions to said central station through said patient stated.

8. The system according to claim 1, further including a patient condition monitoring device for monitoring patient physiological conditions, said patient monitoring device being connected to one of said badges for communicating at least a portion of said monitored conditions to said one of said badges, wherein said one of said badges in turn forwards said portion of monitored conditions through a respective receiver to said central station.

\* \* \* \* \*